US012559719B2

(12) United States Patent
Posey et al.

(10) Patent No.: US 12,559,719 B2
(45) Date of Patent: Feb. 24, 2026

(54) ENGINEERED EXPRESSION OF CELL SURFACE AND SECRETED SIALIDASE BY CAR T CELLS FOR INCREASED EFFICACY IN SOLID TUMORS

(71) Applicants: The Trustees of the University of Pennsylvania, Philadelphia, PA (US); The United States of America as represented by the Department of Veterans Affairs, Washington, DC (US)

(72) Inventors: Avery D. Posey, Philadelphia, PA (US); Tiffany King, Philadelphia, PA (US)

(73) Assignees: The Trustees of the Unviersity of Pennsylvania, Philadelphia, PA (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 18/622,066

(22) Filed: Mar. 29, 2024

(65) Prior Publication Data

US 2024/0368546 A1  Nov. 7, 2024

Related U.S. Application Data

(62) Division of application No. 16/879,636, filed on May 20, 2020, now abandoned.

(60) Provisional application No. 62/850,014, filed on May 20, 2019.

(51) Int. Cl.
| | |
|---|---|
| *C12N 5/0783* | (2010.01) |
| *A61K 35/17* | (2025.01) |
| *A61K 40/11* | (2025.01) |
| *A61K 40/30* | (2025.01) |
| *A61K 40/31* | (2025.01) |
| *A61K 40/42* | (2025.01) |
| *A61P 35/00* | (2006.01) |
| *C07K 14/705* | (2006.01) |
| *C07K 14/715* | (2006.01) |
| *C07K 14/725* | (2006.01) |
| *C07K 16/28* | (2006.01) |
| *C07K 16/30* | (2006.01) |
| *C12N 7/00* | (2006.01) |
| *C12N 9/24* | (2006.01) |
| *C12N 15/86* | (2006.01) |

(52) U.S. Cl.
CPC ............ *C12N 5/0636* (2013.01); *A61K 35/17* (2013.01); *A61K 40/11* (2025.01); *A61K 40/30* (2025.01); *A61K 40/31* (2025.01); *A61K 40/4205* (2025.01); *A61K 40/4276* (2025.01); *A61P 35/00* (2018.01); *C07K 14/70507* (2013.01); *C07K 14/7051* (2013.01); *C07K 14/70517* (2013.01); *C07K 14/7151* (2013.01); *C07K 16/2803* (2013.01); *C07K 16/3069* (2013.01); *C12N 5/0646* (2013.01); *C12N 7/00* (2013.01); *C12N 9/2402* (2013.01); *C12N 15/86* (2013.01); *C12Y 302/01018* (2013.01); *A61K 2239/22* (2023.05); *A61K 2239/48* (2023.05); *A61K 2239/58* (2023.05); *C07K 2317/24* (2013.01); *C07K 2317/524* (2013.01); *C07K 2317/526* (2013.01); *C07K 2317/53* (2013.01); *C07K 2317/55* (2013.01); *C07K 2317/622* (2013.01); *C07K 2317/73* (2013.01); *C07K 2319/02* (2013.01); *C07K 2319/03* (2013.01); *C07K 2319/33* (2013.01); *C12N 2740/15043* (2013.01)

(58) Field of Classification Search
None
See application file for complete search history.

(56) References Cited

U.S. PATENT DOCUMENTS

| | | | | |
|---|---|---|---|---|
| 7,368,531 | B2 | 5/2008 | Rosen | |
| 8,716,445 | B2 | 5/2014 | Lal | |
| 2008/0311098 | A1* | 12/2008 | Lapointe | C07K 14/4748 |
| | | | | 435/375 |
| 2013/0116165 | A1 | 5/2013 | Schmidt | |
| 2016/0106817 | A1 | 4/2016 | Moss | |
| 2016/0184407 | A1 | 6/2016 | Fang | |
| 2016/0297884 | A1* | 10/2016 | Kuo | A61P 35/00 |
| 2017/0119859 | A1 | 5/2017 | Moss | |
| 2017/0334968 | A1* | 11/2017 | Cooper | C07K 16/32 |
| 2018/0118834 | A1 | 5/2018 | Brogdon | |
| 2019/0330306 | A1* | 10/2019 | Noonan | C07K 14/70521 |

FOREIGN PATENT DOCUMENTS

| | | |
|---|---|---|
| WO | 2020142727 A1 | 7/2020 |
| WO | 2021087356 A1 | 5/2021 |

OTHER PUBLICATIONS

Zabel et al., The making and function of CAR cells, Immunology Letters, 212 (2019) 53-69, Publication Date: Jun. 7, 2019 (Year: 2019).*
Ajina et al., Strategies to Address Chimeric Antigen Receptor Tonic Signaling, Molecular Cancer Therapeutics, 17(9), Publication Date: Sep. 2018 (Year: 2018).*
Büll et al., Sweet escape: Sialic acids in tumor immune evasion, Biochimica et Biophysica Act, 1846, (2014) 238-246, Publication Date: Jul. 12, 2014 (Year: 2014).*
Xu et al., Proc Mach Learn Res., Nov. 2022; 165 (Year: 2022).*

(Continued)

*Primary Examiner* — Peter J Reddig
*Assistant Examiner* — Cheng Lu
(74) *Attorney, Agent, or Firm* — Saul Ewing LLP; Alireza Behrooz; Kathryn Doyle

(57) ABSTRACT

The present disclosure provides modified immune cells or precursors thereof (e.g. modified T cells) comprising a chimeric cell surface sialidase or a variant sialidase precursor protein. Compositions and methods of treatment are also provided.

20 Claims, 23 Drawing Sheets

Specification includes a Sequence Listing.

(56)           References Cited

OTHER PUBLICATIONS

Geudan et al., Engineering and Design of Chimeric Antigen Receptors, Molecular Therapy: Methods & Clinical Development vol. 12, 145-156, Publication Date: Mar. 2019 (Year: 2019).

International Search Report and Written Opinion issued in PCT/US2020/033852, mailed Sep. 4, 2020.

Monti etal. Expression ofa novel human sialidase encoded by the NEU2 gene, Glycobiology vol. 9, No. 12, pp. 1313-1321, Publication Year: 1999 (Year: 2010).

* cited by examiner

Key
scFv w/ linker
Transmembrane domain
CD3z
4-1BB co-stimulatory domain
Cancer-specific epitope
Carbohydrate residue w/ terminal sialic acids
Neuraminidase
Hinge
Sialylated NKG2D ligand

PC3

DU145 pTRPE-Neu2-BBz nucleotide sequence (SEQ ID NO: 1)

CD8α Leader (SEQ ID NO: 2) -
ATGGCCTTACCAGTGACCGCCTTGCTCCTGCCGGTCCTTGCTCCTGCCGGCCTTGCTCCTGCGCCGCCAGGCCG

Spacer -
GGATCC

Neu2 (SEQ ID NO: 4) -
ATGGCTTCCTTGCCGGTGCTGCAAAAAGAGAGAGGCGTATTCCAGTCAGGCGCCCATGCGTATAGAATCCGGCACTTCTCTATTTGCCGGGCCAACAAAGTCTCTTGGCGTTCG
CGGAACAGCGGGGCGTCCAAAAAGAGAGCGAACACGCCGAGTTGATTGTGCTCCGCGGGGATTATGATGCCCCAACGCATCAGGTTCAGTGGCAGGCACAAGAGGTAGTC
GCTCAGGCGCGACTGGATGGACATCGGTCAATGAACCCATGTCAGACAGCAGGTACGTTGTTTCTGTTCTTCATCGTATCCTGGCAAGTAACAGAAC
AACACAACTGCAAACCAGAGCCAATGTAACAAGACTCTGCCAGTAACTAGCACTAGCACCACGACGAACGTGGCTTCCCCTGCAAGATCTTACTGACGCGCAATCGGGC
CTGCATATCGCGAATGGAGCACTTCGCAGTAGGCCCTGCAACTCATTGCTGCAACGCGGCGACCATCCATGATCGCCGATCACTGGTGCCAGCGGATACGTTGGGTGTCAGGTAGCGGAA
AATACAACGCCCCATCCCGTCCGCTTTTGTTTCCTCTCCCATGACCACGCGCAGTCATCTTCGCCGCCGCAGTCACTCTTCGCGGGCGTACAGGGCCAGAGCACTAATGACGGCTTGATTTTCAAGAAAGTCAACT
GTAGAAACCGGGGAGCAGAGAGTGGTCACTCAGGGCTGTCAAGGTTCAGTTATAAGTTTCAAGCTCACGTCCGGTCCAGGATCACCAGCACAGTGGCTTCTCTACACCAT
CCCACCCACAGCTGGCAGCGGGGCAGATCTTGGTGCTTACTTGAATCCCAGGCACCGGACGAGCCTGGAGCGAGCCTGTACTGCTTGGTGCTGTGCGTAC
TCTGATCTCCAGTCAATGGGTACTGGACCAGATGGGAGTCCATTGTTGGTTGTCTCTACGAGGCGAACGATTATGAGGAAATCGTTTTCTTATGTTTACTTTGAAACAGGC
GTTCCCAGCCGAATATTTGCCTCAG

Spacer -
TCCGGA

CD8α Hinge (SEQ ID NO: 6) -
ACCACGACGCCAGCGCGCGACCACCAACACCGGCGCCACCATCGCGTCGCAGCCCCGTCCCTGCGCCGCCAGAGGGCGTGCCGGCCAGCGGCGGGGGCGCAGTGCACAC
GAGGGGGCTGGACTTCGCCTGT

Transmembrane Domain (SEQ ID NO: 7) -
GATATCTACATCTGGGCGCCCTTGGCCGGGCGGGACTTGTGGGGGTCCTTCTCTGTCACTGGTTATCACCCTTTACTGC

4-1BB ICD (SEQ ID NO: 8) -
AAACGGGGCAGAAGAAGAAACTCCTGTATATATTCAAACAACCATTTATGAGACGACCAGTACAAACTACTCAAGAGGAAGATGGCTGTGAGCTGCCGATTTCCAGAAGAAGAAGAA
GGAGGATGTGAACTG

CD3 zeta (SEQ ID NO: 9) -
AGAGTGAAGTTCAGCAGGAGCGCAGGAGGCGCAGACGCCCCCGCGTACAAGCAGGGCCAGAACCAGCTCTATAACGAGCTCAATCTAGGACGAAGAGAGGAGTACGATGTTTTGGACA
AGAGACGTGGCCGGGACCCTGAGATGGGCGGGAAAGCCGGAGAAGAAACCCTACAAGGCCTGTACAATGAACTGCAGAAAAGATAAGATGGCGGAGGCCTACAGTG
AGATTGGGATGAAAGGCGAGCGCCGGAGGGGCAAGGGCCACGATGGCCTTTACCAGGGTCTCAGTACAGCCACCAAGGACACCTACGACGCCCTTCACATGCAGGCCCT
GCCCCCTCGC

FIG. 13A pTRPE-Neu2-BBz AA sequence (SEQ ID NO: 10)

CD8α Leader (SEQ ID NO: 11) -
MALPVTALLLPLALLLHAARP

Spacer -
GS

Neu2 (SEQ ID NO: 13) -
MASLPVLQKESVFQSGAHAYRIPALLYLPGQQSLLAFAEQRASKKDEHAELIVLRRGDYDAPTHQVQWQAQEVVAQARLDGHRSMNPCPLYDAQ
TGTLFLFFIAIPGQVTEQQLQTRANVTRLCQVTSTDHGRTWSSPRDLTDAAIGPAYREWSTFAVGPGHCLQLHDRARSLVVPAYAYRKLHPIQRPI
PSAFCFLSHDHGRTWARGHFVAQDTLECQVAEVETGEQRVVTLNARSHLRARVQAQSTNDGLDFQESQLVKKLVEPPPQGCQGSVISFPSPRSGP
GSPAQWLLYTHPTHSWQRADLGAYLNPRPPAPEAWSEPVLLAKGSCAYSDLQSMGTGPDGSPLFGCLYEANDYEEIVFLMFTLKQAFPAEYLPQ

Spacer -
SG

CD8α Hinge (SEQ ID NO: 15) -
TTTPAPRPPTPAPTIASQPLSLRPEACRPAAGGAVHTRGLD

Transmembrane Domain (SEQ ID NO: 16) -
FACDIYIWAPLAGTCGVLLLSLVITLYC 4-1BB ICD (SEQ ID NO: 17)-
KRGRKKLLYIFKQPFMRPVQTTQEEDGCSCRFPEEEEGGCEL CD3 zeta (SEQ ID NO: 18) -
RVKFSRSADAPAYKQGQNQLYNELNLGRREEYDVLDKRRGRDPEMGGKPRRKNPQEGLYNELQKDKMAEAYSEIGMKGERRRGKGHDGLYQGL
STATKDTYDALHMQALPPR

FIG. 13B pTRPE-Neu2-Δz nucleotide sequence (SEQ ID NO: 19)

CD8α Leader (SEQ ID NO: 2) -
ATGGCCTTACCAGTGACCGCCTTGCTCCTGCCGCTGGCCTTGCTGCTCCACGCGCCGCCAGGCCG Spacer -
GGATCC Neu2 (SEQ ID NO: 4) -
ATGGCTTCCTTGCCGGTGCTGCAAAAAGAGAGAGCGTATTCCAGTCAGGCGCCCATGCGTATAGAATCCGGCACTTCTCTATTGCCGGGCCAACAAAGTCTC
TTGGCGTTCGCGGAACAGCAGGGGCGTCCAAAAAGACGAACACGCGAGTTGATTGTGCTCCGCGCGGGGGATTATGATGCCCCAACGCATCAGGTTCAGT
GGCAGGCACAAGAGAGGTAGTCGCTCAGGCGCGACTGGACATCGGTGGCACATCGGTGACATGCTAACCCATGTCAATGACCCATGTACGGTTCTGTTC
TTCATCGCTATCCCTGGGCAAGTAACAGAACAACAACAACTGCAAACCAGAGCCAATGTAACAGACTCTGCCAGGTAACTAGCACTGACCACGGACGAAC
GTGGTCTTCCCCTAGAGATCTTACTGACGCCGCAATCGGGCCGTGCATATCGGCCGGAAGCTCCATCCAATACAACGCCCATCCGTCCGCTTTTGTTTCCTCTCCCATGCACTCCATGACCACGGGG
TCGCGCCCGATCACTTGTGGTGCCAGCGTACGCATACCGGAAGCTCGTTGGAGTGTCAGGTATCGTTGGAGTGTCAGGTGTCAGTGGGGAGCAGAGAGTGGTCACTCTCAACGCG
CGCAGTCATCTTCGCGCCCGTACAGGCGCAGAGCACTAATGACGGGCTTGATTTCAAGAAAGTCAACTGTCAAAAAGTTGGTTGAACCGCCCCGCA
GGGCTGTCAAGGTTCAGTTATAAGTTTCAAGTCCACCGCTCCGGTCCAGGATCACCAGCACAGTGGCTTCTCTACACCCATCCACCCACAGCTGGCAGCG
GGCAGATCTTGGTGCTTACTTGAATCCAGGCCACCGGCCCCCAAGCTGGAGCGGGAGCCTGTACTGTTGGAGCCTGTACTCTGATCTCC
AGTCAATGGGTACTGGACCAGATGGGAGTCCATTGTTGGTTGGTCTCTACGAGAGGCGAACGATTATGAGGAAATCGTTTTTCTTATGTTTACTTGAAACAGG
CGTTCCCCAGCCGAATATTTGCCTCAG Spacer -
TCCGGA CD8α Hinge (SEQ ID NO: 6) -
ACCACGACGCCAGCGCCGCGACCACCAACACCGGCGCCCACCATCGCGGTCGCAGCCCCTGTCCCTGCGCCCGCCCAGAGGCGGTGCCGGCCAGCGGCGGGGGGC
GCAGTGCACACGAGGGGGCTGGACTTCGCCTGT Transmembrane Domain (SEQ ID NO: 7) -
GATATCTACATCTGGGCGCCCTTGGCCGGGGACTTGTGGGGTCCTTCTCCTGTCACTGGTTATCACCCTTTACTGC Δ zeta (SEQ ID NO: 20) -
AGAGTGAAGTTCAGCAGGAGCGCCAGAGCGCCAGACGCCCCCGCGTAA

FIG. 13C pTRPE-Neu2-Δz AA sequence (SEQ ID NO: 21)

CD8α Leader (SEQ ID NO: 11) -
MALPVTALLLPLALLLHAARP

Spacer -
GS

Neu2 (SEQ ID NO: 13) -
MASLPVLQKESVFQSGAHAYRIPALLYLPGQQSLLAFAEQRASKKDEHAELIVLRRGDYDAPTHQVQWQAQEVVAQARLDGHRSMNPCPLYDAQ
TGTLFLFFIAIPGQVTEQQQLQTRANVTRLCQVTSTDHGRTWSSPRDLTDAAIGPAYREWSTFAVGPGHCLQLHDRARSLVVPAYAYRKLHPIQRPI
PSAFCFLSHDHGRTWARGHFVAQDTLECQVAEVETGEQRVVTLNARSHLRARVQAQSTNDGLDFQESQLVKKLVEPPPQGCQGSVISFPSPRSGP
GSPAQWLLYTHPTHSWQRADLGAYLNPRPPAPEAWSEPVLLAKGSCAYSDLQSMGTGPDGSPLFGCLYEANDYEEIVFLMFTLKQAFFPAEYLPQ

Spacer -
SG

CD8α Hinge (SEQ ID NO: 15) -
TTTPAPRPPTPAPTIASQPLSLRPEACRPAAGGAVHTRGLD

Transmembrane Domain (SEQ ID NO: 16) -
FACDIYIWAPLAGTCGVLLLSLVITLYC

Δ zeta (SEQ ID NO: 22) -
RVKFSRSADAPA

FIG. 13D pTRPE-Myc-Neu2-BBz nucleotide sequence (SEQ ID NO: 23)

CD8α Leader (SEQ ID NO: 2) -
ATGGCCTTACCAGTGACCGCCTTGCTCCTGCCGCTGGCCTTGCTGCTCCACGCCGCCAGGCCG Myc-Tag (SEQ ID NO: 24) -
GAACAGAAACTTATCTCCGAGGAAGACCTG Spacer -
GGATCC Neu2 (SEQ ID NO: 4) -
ATGGCTTCCTTGCCGGTGCTGCAAAAAGAGAGCGTATTCCAGTCAGGCGCCCATGCTATTCAGGCGCCCATGCTATAGAAATCCGGCACTTCTCTATTGCCGGCCAACAAAGTCTCTTGGCGTTCGCGGAA
CAGCGGGCGTCCAAAAAAGACGAACACGCCGAGTTGATTGTGCTCCGCGCGGGGATTATGATGCCCCAACGCATCAGGTTCAGTGCAGGCACAAGAGGTAGTCGCTCAGGCG
CGACTGGATGGACATCGGTCAATGAACCCATGTCCACTGTACGATGCTCAGACAGGTACGTTGTTTCTGTTCTTCATCGTATCCCTGGCAAGTAACAGAACAACAACTGCAA
ACCAGAGCCAATGTAACAAGACTCTGCCAGTAACTAGCACTGACCACGACGAACGTGGTCTTCCCCTAGAGATCTTACTGACGCGAAGCTCCATCCAATACAACGCCCCGTCGC
CACTTTCGCAGTAGCCCTGGTCATTGCCTGCAACTCCATGATCGCCGGCCGATCGTTGTGGTGCCACCAGGATACGTTGGAGTTGCAGGATAGAAACCGGGAGCAGAGAGTGGTC
TTTTGTTTCCTCTCCCATGACCACGGCGGACTTGGGCGCCGGGGTCATTCGTCGCACAGGATCAATGACGGGCTTGATTTTCAAGAAAGTCAACTGCAAAAAGTTGGTTGAACGCGCCCCGCAGGG
CTGTCAAGGTTCAGTTATAAGTTTTCACGTCCGGTCCAGGATCACCAGCACAGTGGCTTCTCTACACCCATCGACTCTGATCTCAGTCAATGGGTACTGGACGATGGGGAGTCCA
CTTGAATCCCAGGCCACCGGCCCCGAAGCCTGGAGCGAGCCTGTACTGCTTGCAAAGGGGGAGCGTGTGCAGACCGGTGTCCAGTCAATGGGTACTGGACGATGGGGAGTCCA
TTGTTTGGTTGTCTCTACGAGGCGAACGATTATGAGGAAAATCGTTTTTCTTATGTTTACTTTGAAACAGGCGTTCCCAGCCGAATATTTGCCTCAG Spacer -
TCCGGA CD8α Hinge (SEQ ID NO: 6) -
ACCACGACGCCAGCGCCGCGACCACCAACACCGGCGCCACCATCGCGTCGCAGCCCCTGTCCCTGCGCCCCAGAGGCGTGCCGGCCAGCGGCGGGGGGCGCAGTGCACACGAGG
GGGCTGGACTTCGCCTGT Transmembrane Domain (SEQ ID NO: 7) -
GATATCTACATCTGGGCGCCCTTGGCCGGGACTTGTGGGGTCCTTCTCCTGTCACTGGTTATCACCCTTTACTGC 4-1BB ICD (SEQ ID NO: 8) -
AAACGGGGCAGAAAGAAAACTCCTGTATATATTCAAACAACCATTTATGAGACCAGTACAAAACTACTCAAGAGGAAGATGGCTGTAGCGCCGATTTCCAGAAGAAGAAGAAGGAG
GATGTGAACTG CD3 zeta (SEQ ID NO: 9) -
AGAGTGAAGTTCAGCAGGAGCGCAGAGCCGCAGAACAGCTCTATAAGCAGGGCCAGAACCAGCTCTATAACGAGCTCAATCTAGGACGAAGAGAGAGGAGTACGATGTTTGGACAAGAGA
CGTGGCCGGGACCCTGAGATGGGGGGAAAGCCGAGAAGGAGAAACCCTGCAGAAGGCCTGTACAATGAACTGCAGAAAGATAAGATGGCGGAGGCCTACAGTGAGATTGGGAT
GAAAGGCCGAGCGCCGAGGGACGCGGGCAAGGGGCACGATGGCCTTTACCAGGGTCTCAGTACAGCCACCAAGGACACCTACGACGCCCTTCACATGCAGGCCCTGCCCCCTCGC

FIG. 13E pTRPE-Myc-Neu2-BBz AA sequence (SEQ ID NO: 25)

CD8α (SEQ ID NO: 11) -
MALPVTALLLPLALLLHAARP

Myc-Tag (SEQ ID NO: 26) -
EQKLISEEDL

Spacer -
GS

Neu2 (SEQ ID NO: 13) -
MASLPVLQKESVFQSGAHAYRIPALLYLPGQQSLLAFAEQRASKKDEHAELIVLRRGDYDAPTHQVQWQAQEVVAQARLDGHRSMNPCPL
YDAQTGTLFLFFIAIPGQVTEQQQLQTRANVTRLCQVTSTDHGRTWSSPRDLTDAAIGPAYREWSTFAVGPGHCLQLHDRARSLVVPAYAYR
KLHPIQRPIPSAFCFLSHDHGRTWARGHFVAQDTLECQVAEVETGEQRVVTLNARSHLRARVQAQSTNDGLDFQESQLVKKLVEPPPQGCQ
GSVISFPSPRSGPGSPAQWLLYTHPTHSWQRADLGAYLNPRPPAPEAWSEPVLLAKGSCAYSDL
QSMGTGPDGSPLFGCLYEANDYEEIVFLMFTLKQAFPAEYLPQ

Spacer -
SG

CD8α Hinge (SEQ ID NO: 15) -
TTTPAPRPPTPAPTIASQPLSLRPEACRPAAGGAVHTRGLD

Transmembrane Domain (SEQ ID NO: 16) -
FACDIYIWAPLAGTCGVLLLSLVITLYC 4-1BB ICD (SEQ ID NO: 17) -
KRGRKKLLYIFKQPFMRPVQTTQEEDGCSCRFPEEEGGCEL CD3 zeta (SEQ ID NO: 18) -
RVKFSRSADAPAYKQGQNQLYNELNLGRREEYDVLDKRRGRDPEMGGKPRRKNPQEGLYNELQKDKMAEAYSEIGMKGERRRGKGHDGLY
QGLSTATKDTYDALHMQALPPR

FIG. 13F pTRPE-Myc-Neu2-Δz nucleotide sequence (SEQ ID NO: 27)

CD8α Leader (SEQ ID NO: 2) -
ATGGCCTTACCAGTGACCGCCTTGCTCCTGCCGCTGGCCTTGCTGCTCCACGCCGCCAGGCCG Myc-Tag (SEQ ID NO: 24) -
GAACAGAAACTTATCTCCGAGGAAGACCTG Spacer-
GGATCC Neu2 (SEQ ID NO: 4) -
ATGGCTTCCTTGCCGGTGCTGCAAAAAGAGAGAGGCTATTCCAGTCAGGCGCCCATGCGTATAGAATCCCGGCACTTCTCTATTGCCGGCCAACAAAGTCTTGGCGTTCGC
GGAACAGCGGGGCGTCCAAAAAGACGAACACGCGAGTTGATTGTGCTCCGCCGCGGGGATTATGAGCCCAACGCATCAGGTTCAGTGGCAGGCACAAGAGGTAGTCG
CTCAGGCGGCGACTGGACATCGGTCAATGAACCCATGTCCACTGTACGATGTCAGACAGGTACGTTGTTTCGTTCTTCATCGCTATCCTGGGCAAGTAACAGAACAA
CAACAACTGCAAACCAGAGCCAATGTAACAAGACTCTGCCAGTAACTAGCACTAGCACTGACCACGGACGAACGTGGTCTTCCCCTAGAGATCTTACTGACGCGCCAATCGGGCCTG
CATATCGCGAATGGAGCACTTTCGCAGTAGGCCCTGGTCATTGCGTCAACTCACAGGGCGGACTTGGGCGCGGGGTCATTTCGTCGCACAGGATACGTTGGAGTGTCAGGTAGCGGAAGTA
ACAACGCCCCATCCGTCCGCTCTTTGTTTCCTTCTCCCATGACCACGCGCGCAGTCATCTTCGCGCCGCTACAGGCGCAGAGCACTAATGACGGGCTTGATTTCAAGAAAGTCAACTCGTC
AAAAAGTTGGTTGAACCGCCCCGCAGGGCTGTCAAGGTTCAGTTATAAGTTTCCAGGCCCACCGAAGCCTGGAGCGAGCCTGTACTGCTTGCAAAGGGGAGTCGTGCGTACTCTGA
CCACAGCTGGCAGCGGCGCAGATCTTGGTGCTTACTTGGAATCCCAGGCCACCGCACGCTGTCTCTACGAGGCGAACAGATTATGAGGAAATCGTTTTCTTATGTTTACTTTGAAACAGGCGTTCC
TCTCCAGTCAATGGGTACTGGACCAGATGGGAGTCCATTGTTTGGTTGTCTCTACGAGGCGAACAGATTATGAGGAAATCGTTTTCTTATGTTTACTTTGAAACAGGCGTTCC
CAGCCGAATATTTGCCTCAG Spacer-
TCCGGA CD8α Hinge (SEQ ID NO: 6) -
ACCACGACGCCAGCGCCGCGACCACCAACACCGGCGCCCCACCATCGCGTCGACCCCTGTCCCTGCGCGCCAGCCCCCTGCCGCCCAGAGGGCGTGCCGGCCAGCGGGGGGCCAGTGCACAC
GAGGGGGCTGGACTTCGCCTGT Transmembrane Domain (SEQ ID NO: 7) -
GATATCTACATCTGGGCGCCCCTTGGCCGGGACTTGTGGGGTCCTTCTCCGTCACTGGTTATCACCCTTTACTGC Δ Zeta (SEQ ID NO: 20) -
AGAGTGAAGTTCAGCAGGAGCGCAGAGCGCCCCGCGTAA

FIG. 13G pTRPE-Myc-Neu2-Δz AA sequence (SEQ ID NO: 28)

CD8α Leader (SEQ ID NO: 11) -
MALPVTALLLPLALLLHAARP

Myc-Tag (SEQ ID NO: 26) -
EQKLISEEDL

Spacer -
GS

Neu2 (SEQ ID NO: 13) -
MASLPVLQKESVFQSGAHAYRIPALLYLPGQQSLLAFAEQRASKKDEHAELIVLRRGDYDAPTHQVQVWQAQEVVAQARLDGHRSMNPCPL
YDAQTGTLFLFFIAIPGQVTEQQQLQTRANVTRLCQVTSTDHGRTWSSPRDLTDAAIGPAYREWSTFAVGPGHCLQLHDRARSLVVPAYAYR
KLHPIQRPIPSAFCFLSHDHGRTWARGHFVAQDTLECQVAEVETGEQRVVTLNARSHLRARVQAQSTNDGLDFQESQLVKKLVEPPPQGCQ
GSVISFPSPRSGPGSPAQWLLYTHPTHSWQRADLGAYLNPRPPAPEAWSEPVLLAKGSCAYSDL
QSMGTGPDGSPLFGCLYEANDYEEIVFLMFTLKQAFPAEYLPQ

Spacer -
SG

CD8α Hinge (SEQ ID NO: 15) -
TTTPAPRPPTPAPTIASQPLSLRPEACRPAAGGAVHTRGLD

Transmembrane Domain (SEQ ID NO: 16) -
FACDIYIWAPLAGTCGVLLLSLVITLYC

Δ zeta (SEQ ID NO: 22) -
RVKFSRSADAPA

FIG. 13H

Neu1 (SEQ ID NO: 29) -

GGATCCTCCTGGAGTAAAGCCGAAAATGACTTTGGATTGGTGCAGCCTTGGTCACAATGGAACAACTTCTGTGGGTCAGCGGCGGCCAAATCGGATCAG
TTGATACTTTCAGAATCCCCCTTATTACAGCCACGCCGCCGGCGGCACACTTTGCCTTTGCCTTTATAGTAGTTAATGACGGCTAGGAAGATGTCTAGTTCTGACGAAGGCGCTAAAT
TATTGCACTCAGGAGATCCATGGACCAGGGTTCCACTTGGAGCCCTACAGCTTTATTCACTCTGTGCACACAAGGCGGGATGCCAGGTCGCGTCTACGATGCTGGTATGGTCAAA
GTTGTCTCAGATGTAGAAACAGGAGTAGTGTTTCTTTTTATTCACTCTTGATATAGGCACGGAAGTGTTCGCTCCGGGACCGGCTCTGGAATACAAAAGCAAAGA
GGACGATGGGGTATCCTGGTCAACACCAAGAAAATCTTTCACTTGATATAGGCACGGAAGTGTTCGCTCCGGGACCGGCTCTGGAATACAAAAGCAAAGA
GAACCGCGAAAAGGCAGGCTGATAGTTTGTGGACATGGGACCTTGGAGCCTTGGAGCCTTGGAGCGATGGTGTATTTGCTTAGCGATGACCACGGAGCATCATGGCGCT
ATGGCAGTGGGGTGAGCGGGATCCCTATGGCAGCCAAAACAGGAAAATGACTTTAACCCGATGAGTGCCAGCCATACGAACTTCGTGATGGTTCAGT
GGTAATAAATGCGAGGAATCAGAACAACTACCATTGCCATTGTAGGATTGTCCTCCGATCTATGACGCGTGTGACACTTGCGCCCACGCGATGTAACGTT
CGATCCCGAGCTGGTGTAGATCCTGTAGTGGGGCGTGGTGCCGTCGTTACAAGCTCAGGTATCGTTTTTAGTAACCGGCTCACCTGAATTAGAGTCAA
CCTGACCCTGAGGTGGAGCTTCTCAAACGGTACATCTTGGAGAAAGGAGACTGTGCAATTGTGGCCTGGCCTACAGTTCCTGCTACCCTCG
AAGGATCAATGGATGGAGAGAGCAAGCTCCCCAACTTTACGTGCTCACGAGAAGGGCCGAAACCATTATACGAAAGCATTAGCGGTCGCGAAGATCAG
CGTCTATGGAACCCTTTCCGGA

Neu2 (with signal peptide removed) (SEQ ID NO: 30) -

GGATCCGAACAACAGACGTTCAAAAAAAGATGAGCACGCCAGCCGAGCTTATAGTGCTCCGGCGGGGGGGGATTACGATGCGCCACGCATCAGGTGCAGTGGCAG
GCACAGGAGGTCGTAGCGGCAGGCTCGGTTGACGGCCATAGAAGTAGAAGTATGAATCCATGCACAAACTGGCACTCTGTTTTGTTTTTATA
GCAATCCCAGGCAGGTCACAGAGCAGGTCAACAACTCCAGACGACGCAACTAACGTACCGCCTCTGCCAAGTAACTTCCACGGATCACGGTAGGACTTGGT
CATCTCCACGCGCGACCTCACTGATGCGGCCTACCGGCCATTGGGCCTGCTACCGGACGAAGCTGCATCCCATTCAAAGACCCATCCCTTCCGCGTTTTGCTTCCTTAGTCACGATCACGGCAGG
GCAAGGTCCTTGGTGGTGCCAGCCTATGCTACAGGAAGCTGCATCCCATTCAAAGACCCATCCCTTCCGCGTTTTGCTTCCTTAGTCACGATCACGGCAGG
ACTTGGGCTAGAGCGGCCATTGTAGCGCAGGACACTTTGGAATGCCAGGACGACTTGAGGTAAGAAGTCAGCTCGTTAAGAAGCTGGTGGAACCGCCACCCAA
AAGTCACCTTCGCGCTCCGCGTCCAGCCCAAAGTACAAACGATGGACTTGACTTCCAGGAAAGTCAGCTCGTTAAGAAGCTGGTGGAACCGCCACCCAA
GGGTGTCAGGGCAGTGTTATAAGTTTTCCATCTCCCGCACCGCCTGCACCCGAGGCATGGTCAGGCCCGGTGGTTGCTGTACACACCACCACTCTGGCAACG
GGCTGACCTTGGTGCTTATCTCAATCCTGACGCGAAGTCCACTGTTTGGGTGCCTCTATGAGAGGCAAACGATTATGAAGAAATTGTGTTTCTCATGTTCCACCCTTAAACAG
GCATTTCCCGCCGAATATCTCCCGCAGTCCGGA

FIG. 14A

Neu3 (SEQ ID NO: 31)-

GGATCCGAGGTGATGGAAGAAGTAACTACTTGCTCATTTAATTCCCCTCTCTTCAGACACAGGAAGAGACGATCGAGGCATTACTTACCGGATTCCCGCCCTTTGTATATACCACCACACATACGTTTCTTGCATTTGCAGAAAAGCGCTCAACGCGCAGGGATGAGGATGCGCTTCACCGGTGCTCCGGCGAGGGCTCCGAATCGGTCAACTTGTCCAATGGGCCCTCTGAAACCCTCAGGAGGCTACTTTGCCCAGGTCACAGACGATTGTTCAGGTGACGGAGCGCCAGCAGAAGTCAGGATGCGCGTGTTTTGTTTTCATCGTCGTTCGAGGTCATGTGACGGAGCGCCAGCAGATTGTTCAGGTGACGTGAGTTGAAGCATTCATCAAGATGCCGGTTGTTGTTCATGGTCTGAGGTCAGAGATCTGAGAGAGGTCATCTCATATTCAACGGAATACAGCTTCAGTCGTTGGTAGGCTCGTCGTCATCCTGCTATACCTACGGTCATCCTGCTTCCAACTGCCATGCAAGACCAGACCTCACTCTTTGATGATTTACTACGACCACCCGTGTTGTTATTGCTCAGCCGGCGCACCCTAACCGGTGCGAGCACTGTCACCAGATCATGGAGGTTGACGGGGCTCTTTCACGCCAACTCTGCGAACCACCTCATGGTTGCTCAGCTTGCTTGGAAGAAGAAGCTGGTACCCCATCAGAATCATGGCTTCTTTACTCTCACCCAAAGACGACGACCGAGATCCAGCAGATCCAGGATCTTCCTGCTCTGAACCAACCCCCTGAAGCGGCGTGTTGGAGTAGGCCCTGGATTCTCCATTGTGGCCCCAACGTCCAGGAAGCAAGCAAAGATAGATTTGGGGATCTACCTGAACCAAACCCCATCCAGCAGGAGTGTGAACAGATGTGCGTTCAGATGTGGGTACTCTGACCTTGCAGCGTTGGAGGAAGAGGGATTGTTCGGTTGTCTTTTGAATGCGGGACGAAGCAGGAGTGTGAACAGATGTGAACAGCAATTCCGGACTCTTCACTCATCGCGAAATTCTGAGTCACCTTCAAGGGGATTGCACGTCACGTCACCGGGCCGAAACCCATCCCAATTCAAGAGCAATTCCGGA

Neu4 (SEQ ID NO: 32) -

GGATCCCAGCGGATTGTCACCGGATGACTCCCATGCGCATCGGTTGGTTTGCGCAGAGGCACCCTCGCGGGGCGGGGAGTGTGCGCTGGGGGCGCTTTGCATGTGTTGGGTACAGCGCCCTCGCCGGAGCAGCTAGATCAATGAACCCTTGTCCCGTCCGTGCATGACGCGGGGACAGGAACTGTGTTTTGTCTTTATTGCGGTACTGGGTCATACGCCCGAAGCTGTTCAAATTGCAACGGGACGAAACGGGCCAGATCTGTGTTGTTGCTTCCAGGGATGCAGGACTAGCTGGGGCTCCGCGCGGGGATCTCACGGAAGAGGCCATTGGGCCAGTTCAGGACTGGCAACATGGGCCAACCTTGCTGTGTTGGGACCAGGACACATGGAGTGCAGCTTCCGTCAGGTCGGTTGTTGGGTCCCGGCTTACACATATCGGGTCGATGCGGCGAAATGTTCGGAAAAGATATGCCGAAACCTCCGCGCTGTGGACGACACGGCCGGACGTGTGGAGGTGCGGGAGGGTGCGGGGGACAGGCTGGTGGGGAAGGACTTCTTTTTGCCTGCTGAACGAGTTGCGTCCTCCCTGAAACGGTAATGCTCGGGGTTGCCAAGGCAGTATAGTGGGTTTTCCAGCTCCCGCACCCAACCGCCGTTGATCCTGAAGTGGCGATTGGGATAGTTGGTGCCAGTTGCCAGTGGGCCTTTTAGCGACTCCAGCCTCCCCTTTTGGGACCAGGACCGGACACAGCGCGGGGCCTAGACCAGGGGTAGGCGCGTAGGCGCCTAGGCGGGTAAGTGCGCGTAGGCGGTAGTTGGACACTTGCGCTTGCGCCAATGCCTTTGCGCTTCGCCCTCCTCCCAGTCCCAACTGGCTGCTCTATTCTCACCCAGTGGCGCTAGGCGGCGGTTACAGCGACCTGCGAGCGACCTGCTCACAGTCCCGCTTGATCCTAGATCTTGGACAGAACCTTGGGTCTCATATGGAAGGCCCGAGCGACCTGGGTTACAGCGGTGGTTCGCGTGCTTGTGGAGGGGCCCTAGCTGTGGGCTATATGGAAGGCTTTGCACCTTTCTCATTGAGGGAAGTTCTTGAAAATGTACCGGCGATCCCCAACCCCCAAATGGACAGAACCTTGGGTCTCACGGGGGACAAGCCCAGAGGCGCCGCTGGGGGCGCCCAGAGACCCAGAGAGGATGCTGTTGGCCCCTCCTCCGGACTCGGGGGACAAGCCCAGAGAGGATGCTGTTGGCCCCTCCTCCGGA

FIG. 14B

Neu1 (SEQ ID NO: 33) –

MEQLLWVSGRQJGSVDTFRIPLITATPRGTLLAFAEARKMS

SSDEGAKFIALRRSMDQGSTWSPTAFIVNDGDVPDGLNLGAVVSDVETGVVFLFYSLCAHKAGCQVASTMLVWSK

DDGVSWSTPRNLSLDIGTEVFAPGPGSGIQKQ REP RKGRLIVCGH

GTLERDGVFCLLSDDHGASWRYGSGVSGIPYGQPKQENDFNPDECQPYELPDGSVVINARNQNNYHCHCRIVLRSYDACDTLRPRDVTFDPELVDPVV

AAGAVVTSSGIVFFSNPAHPEFRVNLTLRWSFSNGTSWRKETVQL WPGPSGYSSLATLEGSMDGEEEQAPQLYVLYEKGRNHYTESISVAKISVYGTLSG

Neu2 (with signal peptide removed) (SEQ ID NO: 34) –

MNPCPLYDAQTG TLFLFFIAIPGQVTEQQOLQTRANVTRLCQVTSTDHGRTWSSPRDLTDAAIGPAYREWST

FAVGPGHCLQLHDRARSLVVPAYAYRKLHPIQRPIPSAFCFLSHDHGRTWARGHFVAQDT

LECQVAEVETGEQRVVTLNARSHLRARVQAQSTNDGLDFQESQLVKKLVEPPPQGCQGSV

ISFPSPRSGPGSPAQWLLYTHPTHSWQRADLGAYLNPRPPAPEAWSEPVLLAKGSCAYSD

LQSMGTGPDGSPLFGCLYEANDYEEIVFLMFTLKQAFPAEYLPQSG

Neu3 (SEQ ID NO: 35) –

MEEVTTCSFNSPLFRQEDDRGITYRIPALLYIPPTHTFLAFAEKRSTRRDEDALHL

VLRRGLRIGQLVQWGPLKPLMEATLPGHRTMNPCPVWEQKSGCVFLFFICVRGHVTERQQIVSGRNAARLCFIYSQDAGCSWSEVRDLTEEVIGSELKH

WATFAVGPGHGIQLQSGRLVI PAYTYYIPSWFFCFQLPCKTRPHSLMIYSDDLGVTWHHGRLIRPMVTVECEVAEVTGRAG

HPVLYCSARTPNRCRAEALSTDHGEGFQRLALSRQLCEPPHGCQGSVVSFRPLEIPHRCQDSSSKDAPTIQQ

SSPGSSLRLEEEAGTPSESWLLYSHPTSRKQRVDLGIYLNQTPLEAAC

WSRPWILHCGPCGYSDLAALEEEGLFGCLFECGTKQCECEQIAFRLFTHREILSHLQGDCT SPGRNPSQFKSNSG

Neu4 (SEQ ID NO: 36) –

MNPCPVHDAGTGTVF LFFIAVLGHTPEAVQIATGRNAARLCCVASRDAGLSWGSARDLTEEAIGGAVQDWATFAV

GPGHGVQLPSGRLLVPAYTYRVDRRECFGKICRTSPHSFAFYSDDHGRTWRCGGLVPNLR

SGECQLAAVDGGQAGSFLYCNARSPLGSRVQALSTDEGTSFLPAERVASLPETAWGCQGS

IVGFPAPAPNRPRDDSWSVGPGSPLQPPLLGPGVHEPPEEAAVDPRGGQVPGGPFSRLQP

RGDGPRQPGPRPGVSGDVGSWTLALPMPFAAPPQSPTWLLYSHPVGRRARLHMGIRLSQS

PLDPRSWTEPWVIYEGPSGYSDLASIGPAPEGGLVFACLYESGARTSYDEISFCTFSLRE VLENVPASPKPPNLGDKPRGCCWPSSG

FIG. 14C

ENGINEERED EXPRESSION OF CELL SURFACE AND SECRETED SIALIDASE BY CAR T CELLS FOR INCREASED EFFICACY IN SOLID TUMORS

CROSS-REFERENCE TO RELATED APPLICATION

This application is a divisional of U.S. patent application Ser. No. 16/879,636, filed May 20, 2020, which is entitled to priority under 35 U.S.C. § 119(e) to U.S. Provisional Patent Application No. 62/850,014, filed May 20, 2019, the contents of which are hereby incorporated by reference in their entireties herein.

STATEMENT REGARDING FEDERALLY SPONSORED RESEARCH OR DEVELOPMENT

This invention was made with government support under CA214278 awarded by the National Institute of Health and IK2BX004183 awarded by the Department of Veterans Affairs. The government has certain rights in the invention.

SEQUENCE LISTING

The instant application contains a Sequence Listing which has been submitted in XML format via Patent Center and is hereby incorporated by reference in its entirety. Said XML copy, created on Mar. 21, 2024, is named 046483-7257US2.xml and is 98,535 bytes in size.

BACKGROUND OF THE INVENTION

Chimeric antigen receptors (CARs) are antibody-based, artificial T cell receptors that endow synthetic retargeting of patient T cells towards cancer-specific epitopes. CAR T cells targeting CD19 are now FDA approved for the treatment of pediatric acute lymphoblastic leukemia (ALL) and adult diffuse large B cell lymphoma. While these immunotherapy advancements are revolutionary for the treatment of blood cancers, leukemia and lymphomas represent just 8% of all cancer indications and 7% of cancer-related deaths. The greatest unmet burdens for cancer treatments are solid tumors, particularly prostate, breast, colorectal and lung cancers, which account for 45% of all cancer-related deaths. Translating CAR T cell therapy into solid tumors requires overcoming significant tumor-associated challenges, including specific target identification, tumor heterogeneity, and dense immunosuppressive stroma, which are associated with increasing tumor aggressiveness.

There is a need in the art for improving CAR T cell therapies, specifically CAR T anti-tumor efficacy in solid tumors. The present invention addresses this need.

SUMMARY OF THE INVENTION

The present invention is based on the discovery that CAR T therapies may be improved by endowing glycoediting activity to the T cells.

In one aspect, the invention includes a modified immune cell or precursor cell thereof, comprising: (a) a chimeric cell surface sialidase (neuraminidase) enzyme comprising an extracellular portion comprising a sialidase (neuraminidase) or an enzymatically functional portion thereof, and (b) a heterologous transmembrane domain capable of tethering the extracellular portion to a cell surface.

In another aspect, the invention includes a modified immune cell or precursor cell thereof, comprising: (a) a chimeric cell surface sialidase consisting of the amino acid sequence set forth in any one of SEQ ID NOs: 10, 37, or 38; and/or (b) a variant sialidase precursor protein comprising a heterologous secretory sequence operably linked to a sialidase (neuraminidase) or an enzymatically functional portion thereof, wherein the variant sialidase precursor protein lacks a transmembrane domain, and wherein the sialidase or enzymatically functional portion thereof is capable of being secreted from an immune or precursor cell thereof when the variant sialidase precursor protein is expressed in the cell; and/or (c) a variant sialidase precursor protein comprising a heterologous secretory sequence operably linked to a sialidase (neuraminidase) or an enzymatically functional portion thereof, wherein the sialidase comprises the amino acid sequence set forth in SEQ ID NO: 34; and/or (d) a chimeric cell surface sialidase (neuraminidase) enzyme comprising an extracellular portion comprising a sialidase (neuraminidase) or an enzymatically functional portion thereof, and a heterologous transmembrane domain capable of tethering the extracellular portion to a cell surface; and a chimeric antigen receptor (CAR) and/or a T cell receptor (TCR); and/or (e) a variant sialidase precursor protein comprising a heterologous secretory sequence operably linked to a sialidase (neuraminidase) or an enzymatically functional portion thereof, wherein the variant sialidase precursor protein lacks a transmembrane domain, and wherein the sialidase or enzymatically functional portion thereof is capable of being secreted from an immune or precursor cell thereof when the variant sialidase precursor protein is expressed in the cell; and a chimeric antigen receptor (CAR) and/or a T cell receptor (TCR); and/or (f) a chimeric cell surface sialidase (neuraminidase) enzyme comprising an extracellular portion comprising Neu2 or an enzymatically functional portion thereof, and a heterologous transmembrane domain capable of tethering the extracellular portion to a cell surface; and a chimeric antigen receptor (CAR); and/or (g) a chimeric cell surface sialidase (neuraminidase) enzyme comprising an extracellular portion comprising Neu2 or an enzymatically functional portion thereof, and a heterologous transmembrane domain capable of tethering the extracellular portion to a cell surface; and a chimeric antigen receptor (CAR) having specificity for TnMUC1, CD19, or PSMA; and/or (h) a chimeric cell surface sialidase (neuraminidase) enzyme comprising an extracellular portion comprising Neu2 or an enzymatically functional portion thereof, a heterologous transmembrane domain capable of tethering the extracellular portion to a cell surface, a hinge domain, and an intracellular region comprising a costimulatory signaling domain and an intracellular signaling domain; and a chimeric antigen receptor (CAR); and/or (i) a chimeric cell surface sialidase (neuraminidase) enzyme comprising an extracellular portion comprising Neu2 or an enzymatically functional portion thereof, a heterologous transmembrane domain capable of tethering the extracellular portion to a cell surface, a hinge domain, and an intracellular region comprising a costimulatory signaling domain and an intracellular signaling domain; and a chimeric antigen receptor (CAR) having specificity for TnMUC1, CD19, or PSMA; and/or (j) a variant sialidase precursor protein comprising a heterologous secretory sequence operably linked to a sialidase (neuraminidase) or an enzymatically functional portion thereof, wherein the variant sialidase precursor protein lacks a transmembrane domain, and wherein the sialidase or enzymatically functional portion thereof is capable of being secreted from an immune or precursor cell thereof when the variant sialidase precursor protein is expressed in the cell; and a chimeric antigen receptor (CAR) having specificity for TnMUC1, CD19, or PSMA.

In various embodiments of the above aspects or any other aspect of the invention delineated herein, the sialidase is a human or humanized sialidase. In certain embodiments, the sialidase is a human or humanized sialidase wherein the human sialidase is selected from the group consisting of Neu1, Neu2, Neu3, and Neu4. In certain embodiments, the sialidase is a human or humanized sialidase wherein the human sialidase is Neu2.

In certain embodiments, the sialidase comprises the amino acid sequence set forth in SEQ ID NO: 13. In certain embodiments, the sialidase comprises the amino acid sequence set forth in SEQ ID NO: 10. In certain embodiments the sialidase consists of the amino acid sequence set forth in SEQ ID NO: 10. In certain embodiments, the sialidase comprises the amino acid sequence set forth in any one of SEQ ID NOs: 10, 37, or 38. In certain embodiments, the sialidase consists of the amino acid sequence set forth in any one of SEQ ID NOs: 10, 37, or 38. In certain embodiments, the sialidase comprises the amino acid sequence set forth in SEQ ID NO: 34. In certain embodiments, the sialidase consists of the amino acid sequence set forth in SEQ ID NO: 34.

In certain embodiments, the variant sialidase precursor protein comprises the amino acid sequence set forth in SEQ ID NO: 13. In certain embodiments, the variant sialidase precursor protein consists of the amino acid sequence set forth in SEQ ID NO: 13.

In certain embodiments, the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154. In certain embodiments, the transmembrane domain comprises a transmembrane domain of CD8. In certain embodiments, the transmembrane domain comprises a transmembrane domain of CD8 alpha. In certain embodiments, the transmembrane domain comprises the amino acid sequence set forth in SEQ ID NO: 16.

In certain embodiments, the chimeric cell surface sialidase further comprises a hinge domain. In certain embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of CD8, or any combination thereof. In certain embodiments, the hinge domain is a hinge comprising an amino acid sequence of CD8. In certain embodiments, the hinge domain is a hinge comprising an amino acid sequence of CD8 alpha. In certain embodiments, the hinge domain comprises the amino acid sequence set forth in SEQ ID NO: 15.

In certain embodiments, the chimeric cell surface sialidase further comprises intracellular region comprising a costimulatory signaling domain and an intracellular signaling domain. In certain embodiments, the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, and B7-H3 (CD276), or a variant thereof. In certain embodiments, the costimulatory signaling domain comprises a costimulatory domain of 4-1BB. In certain embodiments, the costimulatory signaling domain comprises the amino acid sequence set forth in SEQ ID NO: 17. In certain embodiments, the costimulatory signaling domain comprises a costimulatory domain of CD2.

In certain embodiments, the intracellular signaling domain comprises an intracellular domain selected from the group consisting of cytoplasmic signaling domains of a human CD3 zeta chain (CD3z), FcγRIII, FcεRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In certain embodiments, the intracellular signaling domain comprises an intracellular domain of CD3zeta. In certain embodiments, the intracellular signaling domain comprises the amino acid sequence set forth in SEQ ID NO: 18.

In certain embodiments, the modified immune cell further comprises a chimeric antigen receptor (CAR) and/or a T cell receptor (TCR).

In certain embodiments, the CAR comprises an antigen binding domain, a transmembrane domain, and an intracellular region. In certain embodiments, the CAR comprises an antigen binding domain selected from the group consisting of an antibody, an scFv, and a Fab. In certain embodiments, the CAR comprises an antigen binding domain comprising specificity for a tumor associated antigen (TAA). In certain embodiments, the CAR comprises an antigen binding domain comprising specificity for TnMUC1. In certain embodiments, the CAR comprises an antigen binding domain comprising specificity for CD19. In certain embodiments, the CAR comprises an antigen binding domain comprising specificity for PSMA. In certain embodiments, the CAR further comprises a hinge domain.

In certain embodiments, the TCR is specific for a tumor associated antigen (TAA). In certain embodiments, the TCR is selected from the group consisting of a wild-type TCR, a high affinity TCR, and a chimeric TCR. In certain embodiments, the TCR comprises a TCR alpha chain and a TCR beta chain.

In certain embodiments, the modified cell is a modified immune cell. In certain embodiments, the modified cell is a modified T cell. In certain embodiments, the modified cell is an autologous cell. In certain embodiments, the modified cell is an autologous cell obtained from a human subject.

In another aspect, the invention includes a pharmaceutical composition comprising a therapeutically effective amount of any of the modified cells disclosed herein. In certain embodiments, the composition further comprises a therapeutically effective population of innate immune cells. In certain embodiments, the innate immune cells are NK cells. In certain embodiments, the innate immune cells are NK cells and the NK cells are autologous NK cells. In certain embodiments, the innate immune cells are NK cells and the NK cells are autologous NK cells obtained from a human subject.

In certain embodiments, the pharmaceutical composition comprises a therapeutically effective amount of a modified immune cell or precursor cell thereof, wherein the modified cell comprises a chimeric cell surface sialidase (neuraminidase) enzyme comprising an extracellular portion comprising Neu2 or an enzymatically functional portion thereof, and a heterologous transmembrane domain capable of tethering the extracellular portion to a cell surface, and a chimeric antigen receptor (CAR); and a therapeutically effective amount of an NK cell.

In certain embodiments, the pharmaceutical composition comprises a therapeutically effective amount of a modified immune cell or precursor cell thereof, wherein the modified cell comprises a chimeric cell surface sialidase (neuraminidase) enzyme comprising an extracellular portion comprising Neu2 or an enzymatically functional portion thereof, a heterologous transmembrane domain capable of tethering the extracellular portion to a cell surface, a hinge domain, and an intracellular region comprising a costimulatory signaling domain and an intracellular signaling domain, and a chimeric antigen receptor (CAR); and a therapeutically effective amount of an NK cell.

In certain embodiments, the pharmaceutical composition comprises a therapeutically effective amount of a modified immune cell or precursor cell thereof, wherein the modified cell comprises a variant sialidase precursor protein comprising a heterologous secretory sequence operably linked to a sialidase (neuraminidase) or an enzymatically functional portion thereof, wherein the variant sialidase precursor protein lacks a transmembrane domain, and wherein the sialidase or enzymatically functional portion thereof is capable of being secreted from an immune or precursor cell thereof when the variant sialidase precursor protein is expressed in the cell, and a chimeric antigen receptor (CAR); and a therapeutically effective amount of an NK cell.

In another aspect, the invention includes a chimeric cell surface sialidase (neuraminidase) enzyme comprising an extracellular portion comprising a sialidase (neuraminidase) or an enzymatically functional portion thereof, and a heterologous transmembrane domain capable of tethering the extracellular portion to a cell surface.

In certain embodiments, the sialidase is a human or humanized sialidase. In certain embodiments, the sialidase is a human or humanized sialidase and the human sialidase is selected from the group consisting of Neu1, Neu2, Neu3, and Neu4. In certain embodiments, the sialidase is a human or humanized sialidase and the human sialidase is Neu2. In certain embodiments, the sialidase comprises the amino acid sequence set forth in SEQ ID NO: 13. In certain embodiments, the cell surface sialidase comprises the amino acid sequence set forth in SEQ ID NO: 10. In certain embodiments, the cell surface sialidase comprises the amino acid sequence set forth any one of SEQ ID NOs: 10, 37, or 38.

In certain embodiments, the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154. In certain embodiments, the transmembrane domain comprises a transmembrane domain of CD8. In certain embodiments, the transmembrane domain comprises a transmembrane domain of CD8 alpha. In certain embodiments, the transmembrane domain comprises the amino acid sequence set forth in SEQ ID NO: 16.

In certain embodiments, the cell surface sialidase further comprises a hinge domain; and/or an intracellular region comprising a costimulatory signaling domain and an intracellular signaling domain.

In certain embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of CD8, or any combination thereof. In certain embodiments, the hinge domain is a hinge comprising an amino acid sequence of CD8. In certain embodiments, the hinge domain is a hinge comprising an amino acid sequence of CD8 alpha. In certain embodiments, the hinge domain comprises the amino acid sequence set forth in SEQ ID NO: 15.

In certain embodiments, the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, and B7-H3 (CD276). In certain embodiments, the costimulatory signaling domain comprises a costimulatory domain of 4-1BB. In certain embodiments, the costimulatory signaling domain comprises the amino acid sequence set forth in SEQ ID NO: 17.

In certain embodiments, the intracellular signaling domain comprises an intracellular domain selected from the group consisting of cytoplasmic signaling domains of a human CD3 zeta chain (CD3z), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In certain embodiments, the intracellular signaling domain comprises an intracellular domain of CD3z. In certain embodiments, the intracellular signaling domain comprises the amino acid sequence set forth in SEQ ID NO: 18.

In another aspect, the invention includes a variant sialidase precursor protein, comprising a heterologous secretory sequence operably linked to a sialidase (neuraminidase) or an enzymatically functional portion thereof, wherein the variant sialidase precursor protein lacks a transmembrane domain, and wherein the sialidase or enzymatically functional portion thereof is capable of being secreted from an immune or precursor cell thereof when the variant sialidase precursor protein is expressed in the cell; and/or a heterologous secretory sequence operably linked to a sialidase (neuraminidase) or an enzymatically functional portion thereof, wherein the sialidase comprises the amino acid sequence set forth in SEQ ID NO: 34.

In certain embodiments, the sialidase is a human sialidase. In certain embodiments, the sialidase is a human sialidase and wherein the human sialidase is selected from the group consisting of Neu1, Neu2, Neu3, and Neu4. In certain embodiments, the variant sialidase is a variant Neu2. In certain embodiments, the variant sialidase is a variant Neu2 and the variant Neu2 comprises the amino acid sequence set forth in SEQ ID NO: 13.

In another aspect, the invention includes a nucleic acid comprising (a) a first nucleic acid encoding a chimeric cell surface sialidase (neuraminidase) enzyme comprising an extracellular portion comprising a sialidase (neuraminidase) or an enzymatically functional portion thereof, and a heterologous transmembrane domain capable of tethering the extracellular portion to a cell surface; and/or (b) a first nucleic acid sequence encoding any of the cell surface sialidases or the variant sialidases disclosed herein; and/or (c) a first nucleic acid sequence encoding a variant sialidase precursor protein comprising SEQ ID NO: 30; and/or (d) a first nucleic acid sequence encoding a variant sialidase precursor protein comprising SEQ ID NO: 30; and/or (e) a first nucleic acid sequence encoding a chimeric cell surface sialidase comprising SEQ ID NO: 1 or 40; and/or (f) a first nucleic acid sequence encoding a variant sialidase precursor protein comprising a heterologous secretory sequence operably linked to a sialidase (neuraminidase) or an enzymatically functional portion thereof, wherein the variant sialidase precursor protein lacks a transmembrane domain, and wherein the sialidase or enzymatically functional portion thereof is capable of being secreted from an immune or precursor cell thereof when the variant sialidase precursor protein is expressed in the cell; and/or (g) a first nucleic acid sequence encoding a chimeric cell surface sialidase (neuraminidase) enzyme comprising an extracellular portion comprising a sialidase (neuraminidase) or an enzymatically functional portion thereof, and a heterologous transmembrane domain capable of tethering the extracellular portion to a cell surface, and a second nucleic acid sequence encoding a chimeric antigen receptor (CAR) and/or a T cell receptor (TCR); and/or (h) a first nucleic acid sequence encoding a variant sialidase precursor protein comprising a heterologous secretory sequence operably linked to a sialidase (neuraminidase) or an enzymatically functional portion thereof, wherein the variant sialidase precursor protein lacks a transmembrane domain, and wherein the sialidase or enzymatically functional portion thereof is capable of being secreted from an immune or precursor cell thereof when the variant sialidase precursor protein is expressed in the cell, and a second nucleic acid sequence encoding a chimeric antigen receptor (CAR) and/or a T cell receptor (TCR).

In certain embodiments, (a) the sialidase is a human or humanized sialidase; and/or (b) the sialidase is a human or humanized sialidase and wherein the human sialidase is selected from the group consisting of Neu1, Neu2, Neu3, and Neu4; and/or (c) the sialidase is a human or humanized sialidase and wherein the sialidase is Neu2; and/or (d) the sialidase is encoded by a nucleic acid sequence comprising SEQ ID NO: 4; and/or (e) the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154; and/or (f) the transmembrane domain comprises a transmembrane domain of CD8; and/or (g) the transmembrane domain comprises a transmembrane domain of CD8 alpha; and/or (h) the transmembrane domain is encoded by a nucleic acid sequence comprising SEQ ID NO: 7; and/or (i) the nucleic acid further comprises a leader sequence; and/or (j) the nucleic acid further comprises a leader sequence and wherein the leader sequence is a CD8 alpha leader sequence; and/or (k) the nucleic acid further comprises a leader sequence and wherein the leader sequence is encoded by a nucleic acid sequence comprising SEQ ID NO: 2; and/or (l) the nucleic acid further comprises a hinge domain; and/or (m) the nucleic acid further comprises a hinge domain and wherein the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of CD8, or any combination thereof; and/or (n) the nucleic acid further comprises a hinge domain and wherein the hinge domain is a hinge comprising an amino acid sequence of CD8; and/or (o) the nucleic acid further comprises a hinge domain and wherein the hinge domain is a hinge comprising an amino acid sequence of CD8 alpha; and/or (p) the nucleic acid further comprises a hinge domain and wherein the hinge domain is encoded by a nucleic acid sequence comprising SEQ ID NO: 6; and/or (q) the nucleic acid further comprises an intracellular region comprising a costimulatory signaling domain and an intracellular signaling domain.

In certain embodiments, (i) the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, and B7-H3 (CD276), or a variant thereof; and/or (ii) the costimulatory signaling domain comprises a costimulatory domain of 4-1BB; and/or (iii) the costimulatory signaling domain is encoded by a nucleic acid sequence comprising SEQ ID NO: 8; and/or (iv) the intracellular signaling domain comprises an intracellular domain selected from the group consisting of cytoplasmic signaling domains of a human CD3 zeta chain (CD3z), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof; and/or (v) the intracellular signaling domain comprises an intracellular domain of CD3z; and/or (vi) the intracellular signaling domain is encoded by a nucleic acid sequence comprising SEQ ID NO: 9.

In certain embodiments, the nucleic acid further comprises a second nucleic acid sequence encoding an exogenous T cell receptor (TCR) and/or chimeric antigen receptor (CAR).

In certain embodiments, (a) the CAR comprises an antigen binding domain, a transmembrane domain, and an intracellular region; and/or (b) the CAR comprises an antigen binding domain selected from the group consisting of an antibody, an scFv, and a Fab; and/or (c) the CAR comprises an antigen binding domain comprising specificity for a tumor associated antigen (TAA); and/or (d) the CAR comprises an antigen binding domain comprising specificity for TnMUC1; and/or (e) the CAR comprises an antigen binding domain comprising specificity for CD19; and/or (f) the CAR comprises an antigen binding domain comprising specificity for PSMA; and/or (g) the CAR further comprises a hinge domain, and optionally the hinge domain is a hinge domain selected from the group consisting of an Fc fragment of an antibody, a hinge region of an antibody, a CH2 region of an antibody, a CH3 region of an antibody, an artificial hinge domain, a hinge comprising an amino acid sequence of CD8, or any combination thereof.

In certain embodiments, (i) the transmembrane domain is selected from the group consisting of an artificial hydrophobic sequence and transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, CD134, CD137, and CD154; and/or (ii) the intracellular region comprises a costimulatory signaling domain and an intracellular signaling domain; and/or (iii) the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, and B7-H3 (CD276), or a variant thereof; and/or (iv) the costimulatory signaling domain comprises a costimulatory domain of CD2; and/or (v) the costimulatory signaling domain comprises a costimulatory domain of 4-1BB; and/or (vi) the intracellular signaling domain comprises an intracellular domain selected from the group consisting of cytoplasmic signaling domains of a human CD3 zeta chain (CD3z), FcγRIII, FcεRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof; and/or (vii) the intracellular signaling domain comprises an intracellular domain of CD3z.

In certain embodiments, the TCR is specific for a tumor associated antigen (TAA); and/or the TCR is selected from the group consisting of a wild-type TCR, a high affinity TCR, and a chimeric TCR; and/or the TCR comprises a TCR alpha chain coding sequence and a TCR beta chain coding sequence; and/or the TCR alpha chain coding sequence and the TCR beta chain coding sequence are separated by a first linker.

In certain embodiments, (i) the first linker comprises a nucleic acid sequence encoding an internal ribosome entry site (IRES), a furin cleavage site, a self-cleaving peptide, or any combination thereof; and/or (ii) the first linker comprises a furin cleavage site and a self-cleaving peptide, and optionally wherein the self-cleaving peptide is a 2A peptide selected from the group consisting of porcine teschovirus-1 2A (P2A), Thoseaasigna virus 2A (T2A), equine rhinitis A virus 2A (E2A), and foot-and-mouth disease virus 2A (F2A); and/or In certain embodiments, the first nucleic acid sequence and the second nucleic acid sequence are separated by a second linker, optionally wherein: (i) the second linker comprises a nucleic acid sequence encoding an internal ribosome entry site (IRES); and/or (ii) the second linker comprises a cleavage site and/or a self-cleaving peptide, and optionally wherein the cleavage site is a furin cleavage site and/or wherein the self-cleaving peptide is a 2A peptide, and optionally wherein the 2A peptide (A) is selected from the group consisting of porcine teschovirus-1 2A (P2A), Thoseaasigna virus 2A (T2A), equine rhinitis A virus 2A (E2A), and foot-and-mouth disease virus 2A (F2A); (B) is P2A; and/or (C) is T2A; and/or In certain embodiments, the nucleic acid comprises from 5' to 3': the first nucleic acid sequence, the second linker, and the second nucleic acid sequence. In certain embodiments, the nucleic acid comprises from 5' to 3': the second nucleic acid sequence, the second linker, and the first nucleic acid sequence.

In another aspect, the invention includes an expression vector comprising any of the nucleic acids disclosed herein. In certain embodiments, (a) the expression vector is a viral vector selected from the group consisting of a retroviral vector, a lentiviral vector, an adenoviral vector, and an adeno-associated viral vector; and/or (b) the expression vector is a lentiviral vector, and optionally wherein the lentiviral vector is a self-inactivating lentiviral vector.

In another aspect, the invention includes a method of treating cancer in a subject in need thereof. The method comprises: (a) administering any of the modified cells or any of the pharmaceutical composition disclosed herein to the subject; and/or (b) administering a modified T cell comprising a chimeric cell surface sialidase (neuraminidase) enzyme comprising an extracellular portion comprising a sialidase (neuraminidase) or an enzymatically functional portion thereof, and a heterologous transmembrane domain capable of tethering the extracellular portion to a cell surface, and a chimeric antigen receptor (CAR); and/or (c) administering a modified T cell comprising a variant sialidase precursor protein comprising a heterologous secretory sequence operably linked to a sialidase (neuraminidase) or an enzymatically functional portion thereof, wherein the variant sialidase precursor protein lacks a transmembrane domain, and wherein the sialidase or enzymatically functional portion thereof is capable of being secreted from an immune or precursor cell thereof when the variant sialidase precursor protein is expressed in the cell, and a chimeric antigen receptor (CAR); and/or (d) administering to the subject a therapeutically effective amount of a modified T cell comprising a chimeric cell surface sialidase (neuraminidase) enzyme comprising an extracellular portion comprising a sialidase (neuraminidase) or an enzymatically functional portion thereof, and a heterologous transmembrane domain capable of tethering the extracellular portion to a cell surface, and a chimeric antigen receptor (CAR); and administering to the subject a therapeutically effective amount of a NK cell; and/or (e) administering to the subject a therapeutically effective amount of a modified T cell comprising a variant sialidase precursor protein comprising a heterologous secretory sequence operably linked to a sialidase (neuraminidase) or an enzymatically functional portion thereof, wherein the variant sialidase precursor protein lacks a transmembrane domain, and wherein the sialidase or enzymatically functional portion thereof is capable of being secreted from an immune or precursor cell thereof when the variant sialidase precursor protein is expressed in the cell, and a chimeric antigen receptor (CAR); and administering to the subject a therapeutically effective amount of a NK cell.

In certain embodiments, the CAR comprises specificity for TnMUC1; and/or the CAR comprises specificity for CD19; and/or the CAR comprises specificity for PSMA.

In certain embodiments, the method further comprises administering to the subject a population of innate immune cells, optionally wherein the innate immune cells are NK cells; and/or the innate immune cells are NK cells and the NK cells are autologous NK cells obtained from a human subject; and/or the modified T cell and the NK cell are administered simultaneously; and/or the modified T cell and the NK cell are administered separately; and/or the NK cell is autologous; and/or the modified T cell is autologous; and/or the subject is human.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 1A illustrates an iteration of a chimeric sialidase cell-surface receptor that includes T cell signaling domains from 4-1BB and CD3zeta. FIG. 1B illustrates a chimeric sialidase cell-surface receptor without intracellular T cell signaling domains. FIG. 1C illustrates secreted sialidase activity.

FIG. 5E compared to FIG. 5D). FIGS. 5B and 5E represent at 10:1 effector: target ratio of Neu2-BBz T cells:tumor, and show greater activity compared with FIGS. 5C and 5F, which represent a 5:1 effector:target ratio of Neu2-BBz T cells to tumor cells.

FIG. 8A illustrates at 1:1 effector:target ratio, 5E5-CD2z CAR T cells and NTD T cells exhibit no cytotoxic effects against PC3 tumor cells. FIG. 8B illustrates that there is no increased cytotoxicity through the addition of sialidase or NK cells to the 5E5-CART cells. However, when sialidase AND NK cells are added to the 5E5-CART cells, there is virtually complete lysis of PC3 cells, approximating that of the positive lysis control, Triton. Of note, this effect is not observed with 5E5-CART alone, NK cells alone, 5E5-CART+ sialidase, or 5E5-CART+NK cells. FIG. 8C shows the synergy of T cells, NK cells, and sialidase activity is not observed with NTD T cells, demonstrating that CAR activity is required for increased cytotoxicity from this combination. This data suggests that 5E5-CART cell cytotoxicity can cooperate with unmodified innate immune cells, such as NK cells, through the addition of sialidase activity.

FIG. 12A depicts NTD T cells gated on protein L and anti-Myc tag antibody staining. FIG. 12B depicts T cells transduced with the single lentiviral vector 5E5-BBz, gated on protein L and anti-Myc tag stainings. FIG. 12C depicts T cells single transduced with lentiviral vector Myc-Neu1-Dz, gated on protein L and anti-Myc tag staining. FIG. 12D depicts T cells double-transduced with both the 5E5-BBz and Myc-Neu1-Dz lentiviral vectors (referred to as Dual Expressing Sialidase-5E5 T cells), and gated on protein L and anti-Myc tag antibodies. FIG. 12E depicts cytotoxic ability assessed using xCELLigence RTCA. NK cells and effectors listed were co-cultured at a 1:1 ratio with PC3 tumor cells. The 5E5+NK+Sialidase-T cell group is a 3-product co-culture; whereas the Dual Expressing Sialidase-5E5 T cell+NK group is a 2-cell product consisting of NK cells co-cultured with T cells expressing both the Neuraminidase receptor and the 5E5-CAR.

FIGS. 13A-13H depict nucleotide and amino acid sequences of constructs disclosed herein.

FIGS. 14A-14C depict additional sialidase nucleotide and amino acid sequences.

DETAILED DESCRIPTION

Figures 1A, 1B, 1C:
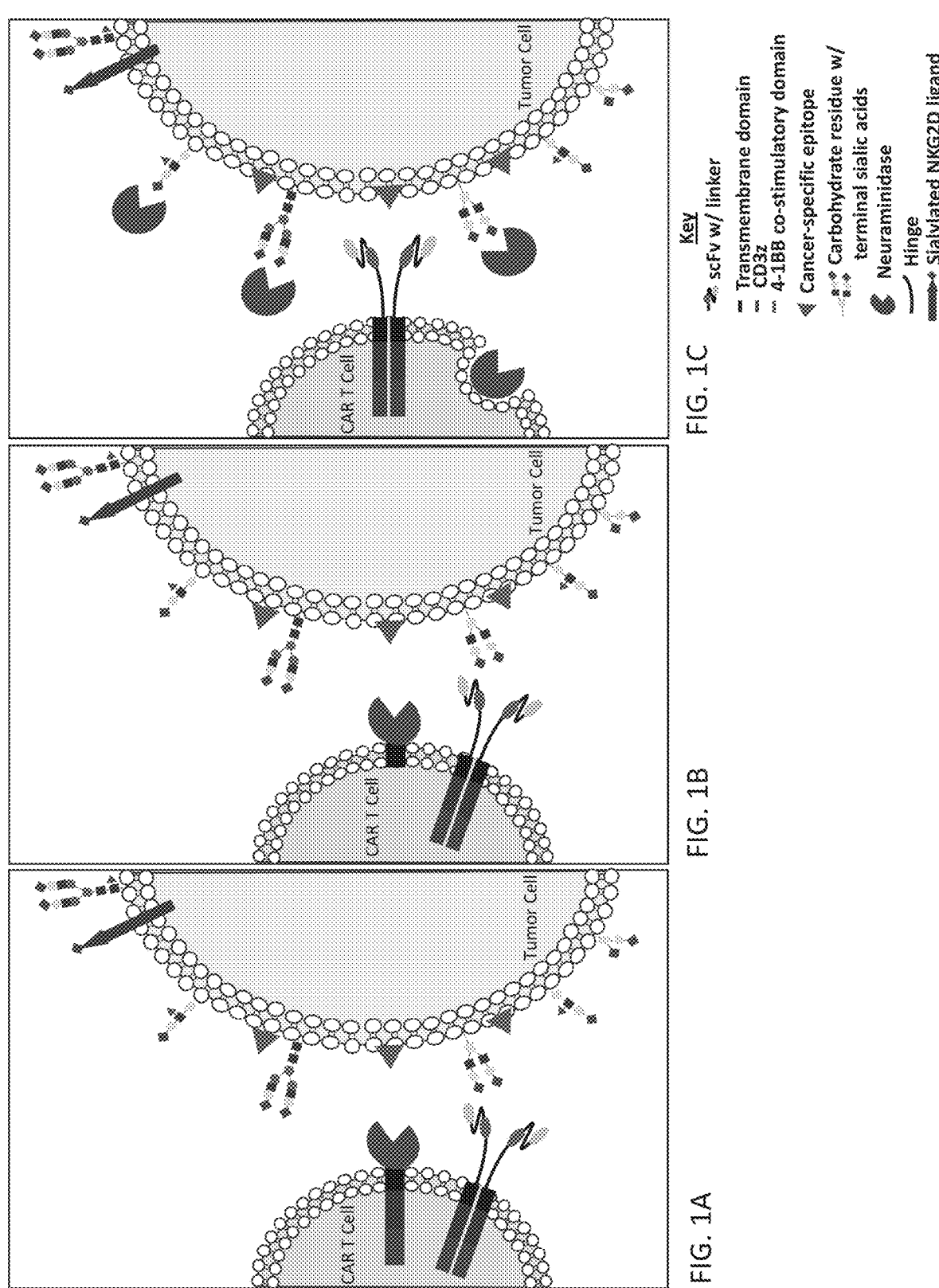
FIGS. 1A-1C depict schematics of CAR-T cells with sialidase enzymatic activity. T cells bearing sialidase/neuraminidase activity can cleave inhibitory sialic acids on tumor cells, thereby enhancing the anti-tumor efficacy of Siglec-expressing innate immune cells, such as NK and monocytes.

The present invention is based on the discovery that CAR T therapies may be improved by endowing glycoediting activity to the T cell, which promotes synergistic cytotoxic effects of the modified and endogenous immune system, mitigating some of the boundaries to T cell infiltration and anti-tumor efficacy seen in solid tumors.

In certain aspects, the present invention provides a chimeric cell surface sialidase (neuraminidase) enzyme comprising an extracellular portion comprising a sialidase (neuraminidase) or an enzymatically functional portion thereof, and a heterologous transmembrane domain capable of tethering the extracellular portion to a cell surface. In another aspect, the invention provides a variant sialidase precursor protein comprising a heterologous secretory sequence operably linked to a sialidase (neuraminidase) or an enzymatically functional portion thereof, and lacks a transmembrane domain. The sialidase or enzymatically functional portion thereof is capable of being secreted from an immune or precursor cell thereof when the variant sialidase precursor protein is expressed in the cell.

Also provided are compositions and methods for modified immune cells or precursors thereof (e.g., modified T cells) comprising a variant sialidase precursor protein or a chimeric cell surface sialidase (neuraminidase) enzyme. In certain embodiments, the modified immune cells or precursors thereof further comprise a chimeric antigen receptor (CAR) and/or a T cell receptor (TCR).

Pharmaceutical compositions comprising a chimeric cell surface sialidase or a variant sialidase precursor protein, nucleic acids encoding a chimeric cell surface sialidase or a variant sialidase precursor protein, and expression vectors comprising nucleic acids comprising a chimeric cell surface sialidase or a variant sialidase precursor protein, are also provided.

The invention also provides methods of treating cancer in a subject in need thereof, comprising administering to the subject a modified T cell comprising a CAR and a variant sialidase precursor protein or a variant sialidase precursor protein. In certain embodiments, the method further comprises administering a population of innate immune cells (e.g. NK cells) to the subject.

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2nd edition).

A. Definitions

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen.

Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. Preferably, the epitope is about 4-18 amino acids, more preferably about 5-16 amino acids, and even more most preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide used in the present invention can be an epitope.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a cellular response to an antigen that occurs when lymphocytes identify antigenic molecules as foreign and induce the formation of antibodies and/or activate lymphocytes to remove the antigen.

The term "immunosuppressive" is used herein to refer to reducing overall immune response.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "oligonucleotide" typically refers to short polynucleotides. It will be understood that when a nucleotide sequence is represented by a DNA sequence (i.e., A, T, C, G), this also includes an RNA sequence (i.e., A, U, C, G) in which "U" replaces "T."

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a nucleic acid sequence that defines a portion of a nucleic acid to which a binding molecule may specifically bind under conditions sufficient for binding to occur. In some embodiments, a target sequence refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

B. Chimeric Cell Surface Sialidases

The present invention provides a chimeric cell surface sialidase (neuraminidase) enzyme comprising an extracellular portion comprising a sialidase (neuraminidase) or an enzymatically functional portion thereof, and a heterologous transmembrane domain capable of tethering the extracellular portion to a cell surface.

The sialidase may be derived from any species. In certain embodiments, the sialidase is from a human. Examples of human sialidases include, but are not limited to, sialidase 1 (Neu1), sialidase 2 (Neu2), sialidase 3 (Neu3), and sialidase 4 (Neu4). In certain embodiments, the sialidase is Neu2. In certain embodiments, the sialidase is humanized.

In certain embodiments, the sialidase comprises Neu2 comprising the amino acid sequence set forth in SEQ ID NO: 13 and may be encoded by the nucleotide sequence set forth in SEQ ID NO: 4. In certain embodiments, the sialidase comprises Neu2 (without a signal peptide) comprising the amino acid sequence set forth in SEQ ID NO: 34 and may be encoded by the nucleotide sequence set forth in SEQ ID NO: 30. In certain embodiments, the sialidase comprises Neu1 comprising the amino acid sequence set forth in SEQ ID NO: 33 and may be encoded by the nucleotide sequence set forth in SEQ ID NO: 29. In certain embodiments, the sialidase comprises Neu3 comprising the amino acid sequence set forth in SEQ ID NO: 35 and may be encoded by the nucleotide sequence set forth in SEQ ID NO: 31. In certain embodiments, the sialidase comprises Neu4 comprising the amino acid sequence set forth in SEQ ID NO: 36 and may be encoded by the nucleotide sequence set forth in SEQ ID NO: 32.

Tolerable variations of the sialidase or an enzymatically functional portion thereof will be known to those of skill in the art. For example, in some embodiments the sialidase or an enzymatically functional portion thereof comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NO: 13, 33, 34, 35, or 36. In some embodiments the sialidase or an enzymatically functional portion thereof is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least or 99% sequence identity to the nucleic acid sequence set forth in SEQ ID NO: 4, 29, 30, 31 or 32.

In some embodiments, the sialidase or an enzymatically functional portion thereof consists of an amino acid sequence set forth in SEQ ID NO: 13, 33, 34, 35, or 36. In some embodiments, the sialidase or an enzymatically functional portion thereof is encoded by a nucleic acid sequence set forth in SEQ ID NO: 4, 29, 30, 31 or 32.

The chimeric cell surface sialidase comprises a heterologous transmembrane domain capable of tethering the extracellular portion to a cell surface. The transmembrane domain of the chimeric cell surface sialidase may comprise any of the transmembrane domains described elsewhere herein (e.g. any CAR transmembrane domain). In certain embodiments, the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154. In certain embodiments, the transmembrane domain comprises a transmembrane domain of CD8. In certain embodiments, the transmembrane domain comprises a transmembrane domain of CD8 alpha. In certain embodiments, the transmembrane domain comprises the amino acid sequence set forth in SEQ ID NO: 16. In certain embodiments, the transmembrane domain consists of the amino acid sequence set forth in SEQ ID NO: 16. In certain embodiments, the transmembrane domain is encoded by the nucleotide sequence set forth in SEQ ID NO: 7.

The chimeric cell surface sialidase may optionally comprise a hinge domain. The hinge domain may comprise any of the hinge domains described in detail elsewhere herein. Hinge domains that may be included in the chimeric cell surface sialidase include, but are not limited, to an Fc fragment of an antibody, a hinge region of an antibody, a CH2 region of an antibody, a CH3 region of an antibody, an artificial hinge domain, a hinge comprising an amino acid sequence of CD8, or any combination thereof. In certain embodiments, the hinge domain is a hinge comprising an amino acid sequence of CD8 or encoded by a nucleotide sequence of CD8. In certain exemplary embodiments, the hinge domain is a hinge comprising an amino acid sequence of CD8 alpha or encoded by a nucleotide sequence of CD8 alpha. In certain exemplary embodiments, the hinge domain comprises the amino acid sequence set forth in SEQ ID NO: 15. In some embodiments, the hinge domain consists of the amino acid sequence set forth in SEQ ID NO: 15. In certain exemplary embodiments, the hinge domain is encoded by the nucleotide sequence set forth in SEQ ID NO: 6.

The chimeric cell surface sialidase may optionally comprise an intracellular region comprising a costimulatory signaling domain and/or an intracellular signaling domain. The intracellular region may comprise any of the intracellular domains or any of the costimulatory signaling domains or any of the intracellular signaling domains described herein. In certain embodiments, the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, and B7-H3 (CD276), or a variant thereof. In certain embodiments, the costimulatory signaling domain comprises a costimulatory domain of 4-1BB. In certain embodiments, the costimulatory signaling domain comprises the amino acid sequence set forth in SEQ ID NO: 17. In some embodiments, the costimulatory signaling domain consists of the amino acid sequence set forth in SEQ ID NO: 17. In certain embodiments, the costimulatory signaling domain is encoded by the nucleotide sequence set forth in SEQ ID NO: 8.

In certain embodiments, the intracellular signaling domain of the chimeric cell surface sialidase comprises an intracellular domain selected from the group consisting of cytoplasmic signaling domains of a human CD3 zeta chain (CD3z), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In certain embodiments, the intracellular signaling domain comprises an intracellular domain of CD3z. In certain embodiments, the intracellular signaling domain comprises the amino acid sequence set forth in SEQ ID NO: 18. In some embodiments, the intracellular signaling domain consists of the amino acid sequence set forth in SEQ ID NO: 18. In certain embodiments, the intracellular signaling domain is encoded by the nucleotide sequence set forth in SEQ ID NO: 9.

Tolerable variations of the hinge or transmembrane domain or costimulatory signaling domain or intracellular signaling domain sequences will be known to those of skill in the art. For example, in some embodiments the hinge or transmembrane domain or costimulatory signaling domain or intracellular signaling domain comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NO: 15, 16, 17, or 18. In some embodiments hinge or transmembrane domain or costimulatory signaling domain or intracellular signaling domain is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least or 99% sequence identity to the nucleic acid sequence set forth in SEQ ID NO: 6, 7, 8, or 9.

In some embodiments, the hinge or transmembrane domain or costimulatory signaling domain or intracellular signaling domain consists of the amino acid sequence set forth in SEQ ID NO: 15, 16, 17, or 18. In some embodiments, the hinge or transmembrane domain or costimulatory signaling domain or intracellular signaling domain is encoded by the nucleic acid sequence set forth in SEQ ID NO: 6, 7, 8, or 9.

In some embodiments, the chimeric cell surface sialidase comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any one of SEQ ID NOs: 10, 21, 25, 28, 37, or 38. In some embodiments, the chimeric cell surface sialidase comprises is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any one of SEQ ID NOs: 1, 19, 23, 27, 39 or 40. In certain embodiments, the chimeric cell surface sialidase comprises the amino acid sequence set forth in any one of SEQ ID NOs: 10, 21, 25, 28, 37, or 38. In certain embodiments, the chimeric cell surface sialidase consists of the amino acid sequence set forth in any one of SEQ ID NOs: 10, 21, 25, 28, 37, or 38. In certain embodiments, the cell surface sialidase is encoded by the nucleic acid set forth in any one of SEQ ID NOs: 1, 19, 23, 27, 39 or 40.

```
Neu2-BBz AA sequence
                                    (SEQ ID NO: 10)
MALPVTALLLPLALLLHAARPGSMASLPVLQKESVFQSGAHAYRIPALLY

LPGQQSLLAFAEQRASKKDEHAELIVLRRGDYDAPTHQVQWQAQEVVAQA
```

-continued
RLDGHRSMNPCPLYDAQTGTLFLFFIAIPGQVTEQQQLQTRANVTRLCQV

TSTDHGRTWSSPRDLTDAAIGPAYREWSTFAVGPGHCLQLHDRARSLVVP

AYAYRKLHPIQRPIPSAFCFLSHDHGRTWARGHFVAQDTLECQVAEVETG

EQRVVTLNARSHLRARVQAQSTNDGLDFQESQLVKKLVEPPPQGCQGSVI

SFPSPRSGPGSPAQWLLYTHPTHSWQRADLGAYLNPRPPAPEAWSEPVLL

AKGSCAYSDLQSMGTGPDGSPLFGCLYEANDYEEIVFLMFTLKQAFPAEY

LPQSGTTTPAPRPPTPAPTIASQPLSLRPEACRPAAGGAVHTRGLDFACD

IYIWAPLAGTCGVLLLSLVITLYCKRGRKKLLYIFKQPFMRPVQTTQEED

GCSCRFPEEEEGGCELRVKFSRSADAPAYKQGQNQLYNELNLGRREEYDV

LDKRRGRDPEMGGKPRRKNPQEGLYNELQKDKMAEAYSEIGMKGERRRGK

GHDGLYQGLSTATKDTYDALHMQALPPR

Neu2-BBz (no leader) AA sequence
                                        (SEQ ID NO: 37)
MASLPVLQKESVFQSGAHAYRIPALLYLPGQQSLLAFAEQRASKKDEHAE

LIVLRRGDYDAPTHQVQWQAQEVVAQARLDGHRSMNPCPLYDAQTGTLFL

FFIAIPGQVTEQQQLQTRANVTRLCQVTSTDHGRTWSSPRDLTDAAIGPA

YREWSTFAVGPGHCLQLHDRARSLVVPAYAYRKLHPIQRPIPSAFCFLSH

DHGRTWARGHFVAQDTLECQVAEVETGEQRVVTLNARSHLRARVQAQSTN

DGLDFQESQLVKKLVEPPPQGCQGSVISFPSPRSGPGSPAQWLLYTHPTH

SWQRADLGAYLNPRPPAPEAWSEPVLLAKGSCAYSDLQSMGTGPDGSPLF

GCLYEANDYEEIVFLMFTLKQAFPAEYLPQSGTTTPAPRPPTPAPTIASQ

PLSLRPEACRPAAGGAVHTRGLDFACDIYIWAPLAGTCGVLLLSLVITLY

CKRGRKKLLYIFKQPFMRPVQTTQEEDGCSCRFPEEEEGGCELRVKFSRS

ADAPAYKQGQNQLYNELNLGRREEYDVLDKRRGRDPEMGGKPRRKNPQEG

LYNELQKDKMAEAYSEIGMKGERRRGKGHDGLYQGLSTATKDTYDALHMQ

ALPPR

Neu2-hinge-Tm AA sequence
                                        (SEQ ID NO: 38)
MALPVTALLLPLALLLHAARPGSMASLPVLQKESVFQSGAHAYRIPALLY

LPGQQSLLAFAEQRASKKDEHAELIVLRRGDYDAPTFIQVQWQAQEVVAQ

ARLDGHRSMNPCPLYDAQTGTLFLFFIAIPGQVTEQQQLQTRANVTRLCQ

VTSTDHGRTWSSPRDLTDAAIGPAYREWSTFAVGPGHCLQLHDRARSLVV

PAYAYRKLHPIQRPIPSAFCFLSHDHGRTWARGHFVAQDTLECQVAEVET

GEQRVVTLNARSHLRARVQAQSTNDGLDFQESQLVKKLVEPPPQGCQGSV

ISFPSPRSGPGSPAQWLLYTHPTHSWQRADLGAYLNPRPPAPEAWSEPVL

LAKGSCAYSDLQSMGTGPDGSPLFGCLYEANDYEEIVFLMFTLKQAFPAE

YLPQSGTTTPAPRPPTPAPTIASQPLSLRPEACRPAAGGAVHTRGLDFAC

DIYIWAPLAGTCGVLLLSLVITLYC

Neu2-BBz nucleotide sequence
                                        (SEQ ID NO: 1)
ATGGCCTTACCAGTGACCGCCTTGCTCCTGCCGCTGGCCTTGCTGCTCCA

CGCCGCCAGGCCGGGATCCATGGCTTCCTTGCCGGTGCTGCAAAAAGAGA

GCGTATTCCAGTCAGGCGCCCATGCGTATAGAATCCCGGCACTTCTCTAT

TTGCCGGGCCAACAAAGTCTCTTGGCGTTCGCGGAACAGCGGGCGTCCAA

-continued
AAAAGACGAACACGCCGAGTTGATTGTGCTCCGCCGCGGGGATTATGATG

CCCCAACGCATCAGGTTCAGTGGCAGGCACAAGAGGTAGTCGCTCAGGCG

CGACTGGATGGACATCGGTCAATGAACCCATGTCCACTGTACGATGCTCA

GACAGGTACGTTGTTTCTGTTCTTCATCGCTATCCCTGGGCAAGTAACAG

AACAACAACAACTGCAAACCAGAGCCAATGTAACAAGACTCTGCCAGGTA

ACTAGCACTGACCACGGACGAACGTGGTCTTCCCCTAGAGATCTTACTGA

CGCCGCAATCGGGCCTGCATATCGCGAATGGAGCACTTTCGCAGTAGGCC

CTGGTCATTGCCTGCAACTCCATGATCGCGCCCGATCACTTGTGGTGCCA

GCGTACGCATACCGGAAGCTCCATCCAATACAACGCCCCATCCCGTCCGC

TTTTTGTTTCCTCTCCCATGACCACGGGCGGACTTGGGCGCGGGGTCATT

TCGTCGCACAGGATACGTTGGAGTGTCAGGTAGCGGAAGTAGAAACCGGG

GAGCAGAGAGTGGTCACTCTCAACGCGCGCAGTCATCTTCGCGCCCGCGT

ACAGGCGCAGAGCACTAATGACGGGCTTGATTTTCAAGAAAGTCAACTCG

TCAAAAAGTTGGTTGAACCGCCCCCGCAGGGCTGTCAAGGTTCAGTTATA

AGTTTTCCAAGTCCACGCTCCGGTCCAGGATCACCAGCACAGTGGCTTCT

CTACACCCATCCCACCCACAGCTGGCAGCGGGCAGATCTTGGTGCTTACT

TGAATCCCAGGCCACCGGCCCCCGAAGCCTGGAGCGAGCCTGTACTGCTT

GCAAAGGGGAGCTGTGCGTACTCTGATCTCCAGTCAATGGGTACTGGACC

AGATGGGAGTCCATTGTTTGGTTGTCTCTACGAGGCGAACGATTATGAGG

AAATCGTTTTTCTTATGTTTACTTTGAAACAGGCGTTCCCAGCCGAATAT

TTGCCTCAGTCCGGAACCACGACGCCAGCGCCGCGACCACCAACACCGGC

GCCCACCATCGCGTCGCAGCCCCTGTCCCTGCGCCCAGAGGCGTGCCGGC

CAGCGGCGGGGGGCGCAGTGCACACGAGGGGGCTGGACTTCGCCTGTGAT

ATCTACATCTGGGCGCCCTTGGCCGGGACTTGTGGGGTCCTTCTCCTGTC

ACTGGTTATCACCCTTTACTGCAAACGGGGCAGAAAGAAACTCCTGTATA

TATTCAAACAACCATTTATGAGACCAGTACAAACTACTCAAGAGGAAGAT

GGCTGTAGCTGCCGATTTCCAGAAGAAGAAGAAGGAGGATGTGAACTGAG

AGTGAAGTTCAGCAGGAGCGCAGACGCCCCCGCGTACAAGCAGGGCCAGA

ACCAGCTCTATAACGAGCTCAATCTAGGACGAAGAGAGGAGTACGATGTT

TTGGACAAGAGACGTGGCCGGGACCCTGAGATGGGGGGAAAGCCGAGAAG

GAAGAACCCTCAGGAAGGCCTGTACAATGAACTGCAGAAAGATAAGATGG

CGGAGGCCTACAGTGAGATTGGGATGAAAGGCGAGCGCCGGAGGGGCAAG

GGGCACGATGGCCTTTACCAGGGTCTCAGTACAGCCACCAAGGACACCTA

CGACGCCCTTCACATGCAGGCCCTGCCCCCTCGC

Neu2-BBz (no leader) nucleotide sequence
                                        (SEQ ID NO: 39)
ATGGCTTCCTTGCCGGTGCTGCAAAAAGAGAGCGTATTCCAGTCAGGCGC

CCATGCGTATAGAATCCCGGCACTTCTCTATTTGCCGGGCCAACAAAGTC

TCTTGGCGTTCGCGGAACAGCGGGCGTCCAAAAAAGACGAACACGCCGAG

TTGATTGTGCTCCGCCGCGGGGATTATGATGCCCCAACGCATCAGGTTCA

GTGGCAGGCACAAGAGGTAGTCGCTCAGGCGCGACTGGATGGACATCGGT

-continued

```
CAATGAACCCATGTCCACTGTACGATGCTCAGACAGGTACGTTGTTTCTG

TTCTTCATCGCTATCCCTGGGCAAGTAACAGAACAACAACAACTGCAAAC

CAGAGCCAATGTAACAAGACTCTGCCAGGTAACTAGCACTGACCACGGAC

GAACGTGGTCTTCCCCTAGAGATCTTACTGACGCCGCAATCGGGCCTGCA

TATCGCGAATGGAGCACTTTCGCAGTAGGCCCTGGTCATTGCCTGCAACT

CCATGATCGCGCCCGATCACTTGTGGTGCCAGCGTACGCATACCGGAAGC

TCCATCCAATACAACGCCCCATCCCGTCCGCTTTTTGTTTCCTCTCCCAT

GACCACGGGCGGACTTGGGCGCGGGGTCATTTCGTCGCACAGGATACGTT

GGAGTGTCAGGTAGCGGAAGTAGAAACCGGGGAGCAGAGAGTGGTCACTC

TCAACGCGCGCAGTCATCTTCGCGCCCGCGTACAGGCGCAGAGCACTAAT

GACGGGCTTGATTTTCAAGAAAGTCAACTCGTCAAAAAGTTGGTTGAACC

GCCCCCGCAGGGCTGTCAAGGTTCAGTTATAAGTTTTCCAAGTCCACGCT

CCGGTCCAGGATCACCAGCACAGTGGCTTCTCTACACCCATCCCACCCAC

AGCTGGCAGCGGGCAGATCTTGGTGCTTACTTGAATCCCAGGCCACCGGC

CCCCGAAGCCTGGAGCGAGCCTGTACTGCTTGCAAAGGGGAGCTGTGCGT

ACTCTGATCTCCAGTCAATGGGTACTGGACCAGATGGGAGTCCATTGTTT

GGTTGTCTCTACGAGGCGAACGATTATGAGGAAATCGTTTTTCTTATGTT

TACTTTGAAACAGGCGTTCCCAGCCGAATATTTGCCTCAGTCCGGAACCA

CGACGCCAGCGCCGCGACCACCAACACCGGCGCCCACCATCGCGTCGCAG

CCCCTGTCCCTGCGCCCAGAGGCGTGCCGGCCAGCGGCGGGGGGCGCAGT

GCACACGAGGGGGCTGGACTTCGCCTGTGATATCTACATCTGGGCGCCCT

TGGCCGGGACTTGTGGGGTCCTTCTCCTGTCACTGGTTATCACCCTTTAC

TGCAAACGGGGCAGAAAGAAACTCCTGTATATATTCAAACAACCATTTAT

GAGACCAGTACAAACTACTCAAGAGGAAGATGGCTGTAGCTGCCGATTTC

CAGAAGAAGAAGAAGGAGGATGTGAACTGAGAGTGAAGTTCAGCAGGAGC

GCAGACGCCCCCGCGTACAAGCAGGGCCAGAACCAGCTCTATAACGAGCT

CAATCTAGGACGAAGAGAGGAGTACGATGTTTTGGACAAGAGACGTGGCC

GGGACCCTGAGATGGGGGGAAAGCCGAGAAGGAAGAACCCTCAGGAAGGC

CTGTACAATGAACTGCAGAAAGATAAGATGGCGGAGGCCTACAGTGAGAT

TGGGATGAAAGGCGAGCGCCGGAGGGGCAAGGGGCACGATGGCCTTTACC

AGGGTCTCAGTACAGCCACCAAGGACACCTACGACGCCCTTCACATGCAG

GCCCTGCCCCCTCGC

Neu2-hinge-Tm nucleotide sequence
                                    (SEQ ID NO: 40)
ATGGCCTTACCAGTGACCGCCTTGCTCCTGCCGCTGGCCTTGCTGCTCCA

CGCCGCCAGGCCGGGATCCATGGCTTCCTTGCCGGTGCTGCAAAAAGAGA

GCGTATTCCAGTCAGGCGCCCATGCGTATAGAATCCCGGCACTTCTCTAT

TTGCCGGGCCAACAAAGTCTCTTGGCGTTCGCGGAACAGCGGGCGTCCAA

AAAAGACGAACACGCCGAGTTGATTGTGCTCCGCCGCGGGGATTATGATG

CCCCAACGCATCAGGTTCAGTGGCAGGCACAAGAGGTAGTCGCTCAGGCG

CGACTGGATGGACATCGGTCAATGAACCCATGTCCACTGTACGATGCTCA

GACAGGTACGTTGTTTCTGTTCTTCATCGCTATCCCTGGGCAAGTAACAG
```

-continued

```
AACAACAACAACTGCAAACCAGAGCCAATGTAACAAGACTCTGCCAGGTA

ACTAGCACTGACCACGGACGAACGTGGTCTTCCCCTAGAGATCTTACTGA

CGCCGCAATCGGGCCTGCATATCGCGAATGGAGCACTTTCGCAGTAGGCC

CTGGTCATTGCCTGCAACTCCATGATCGCGCCCGATCACTTGTGGTGCCA

GCGTACGCATACCGGAAGCTCCATCCAATACAACGCCCCATCCCGTCCGC

TTTTTGTTTCCTCTCCCATGACCACGGGCGGACTTGGGCGCGGGGTCATT

TCGTCGCACAGGATACGTTGGAGTGTCAGGTAGCGGAAGTAGAAACCGGG

GAGCAGAGAGTGGTCACTCTCAACGCGCGCAGTCATCTTCGCGCCCGCGT

ACAGGCGCAGAGCACTAATGACGGGCTTGATTTTCAAGAAAGTCAACTCG

TCAAAAAGTTGGTTGAACCGCCCCCGCAGGGCTGTCAAGGTTCAGTTATA

AGTTTTCCAAGTCCACGCTCCGGTCCAGGATCACCAGCACAGTGGCTTCT

CTACACCCATCCCACCCACAGCTGGCAGCGGGCAGATCTTGGTGCTTACT

TGAATCCCAGGCCACCGGCCCCCGAAGCCTGGAGCGAGCCTGTACTGCTT

GCAAAGGGGAGCTGTGCGTACTCTGATCTCCAGTCAATGGGTACTGGACC

AGATGGGAGTCCATTGTTTGGTTGTCTCTACGAGGCGAACGATTATGAGG

AAATCGTTTTTCTTATGTTTACTTTGAAACAGGCGTTCCCAGCCGAATAT

TTGCCTCAGTCCGGAACCACGACGCCAGCGCCGCGACCACCAACACCGGC

GCCCACCATCGCGTCGCAGCCCCTGTCCCTGCGCCCAGAGGCGTGCCGGC

CAGCGGCGGGGGGCGCAGTGCACACGAGGGGGCTGGACTTCGCCTGTGAT

ATCTACATCTGGGCGCCCTTGGCCGGGACTTGTGGGGTCCTTCTCCTGTC

ACTGGTTATCACCCTTTACTGC
```

C. Variant Sialidase Precursor Protein

The present invention provides a variant sialidase precursor protein, comprising a heterologous secretory sequence operably linked to a sialidase (neuraminidase) or an enzymatically functional portion thereof. In some embodiments, the variant sialidase precursor protein comprises a sialidase or an enzymatically functional portion thereof, wherein the sialidase lacks a transmembrane domain, and is capable of being secreted from an immune or precursor cell thereof when the variant sialidase precursor protein is expressed in the cell.

As used herein, a "heterologous secretory sequence" refers to a peptide sequence that functions to prompt a cell to translocate a protein (e.g., sialidase) that the heterologous secretory sequence is operably linked to. A heterologous secretory sequence may also be referred to as a signal peptide, a signal sequence, a targeting sequence, a targeting signal, a localization signal, a localization sequence, a transit peptide, a leader sequence, a leader peptide, or any other term known in the art. The heterologous secretory sequence may be a short peptide about of 16-30 amino acids in length, e.g., about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36 amino acids in length.

In some embodiments, the heterologous secretory sequence is derived from a naturally occurring protein, for example, a naturally secreted protein. The naturally secreted protein from which a heterologous secretory sequence may be derived may be of, without limitation, human, murine, bovine, camelid, bacterial, or yeast origin. The skilled artisan would be able to choose the appropriate naturally occurring protein and origin from which to derive a heterologous secretory sequence. In certain embodiments, the heterologous secretory sequence is derived from a naturally secreted human protein. Examples of human secreted proteins may be found in, e.g., U.S. Pat. No. 7,368,531, the contents of which are hereby incorporated by reference in its entirety. Examples of signal peptide-containing proteins may be found in, e.g., U.S. Pat. No. 8,716,445, the contents of which are hereby incorporated by reference in its entirety. In some embodiments, the heterologous secretory sequence is a synthetic sequence, see, e.g., Clérico et al., *Biopolymers* (2010) 90(3):307-319, the contents of which are hereby incorporated by reference in its entirety.

In some embodiments, a variant sialidase precursor protein comprises a heterologous secretory sequence operably linked N-terminal to a sialidase or enzymatically functional protein thereof. In some embodiments, a variant sialidase precursor protein comprises a heterologous secretory sequence operably linked C-terminal to a sialidase or enzymatically functional protein thereof. The skilled artisan would readily be able to determine the appropriate location of the heterologous secretory sequence in order for it to perform its intended function, e.g., prompt the cell to translocate the sialidase outside of the cell.

In some embodiments, a variant sialidase precursor protein comprises a heterologous secretory sequence operably linked to a sialidase or enzymatically functional portion thereof. The sialidase or enzymatically functional portion thereof may be derived from any species. Sialidases are found in various species, including mammalian, murine, bacterial, and viral species. In certain embodiments, the sialidase or enzymatically functional portion is from a human. Examples of human sialidases include, but are not limited to, sialidase 1 (Neu1), sialidase 2 (Neu2), sialidase 3 (Neu3), and sialidase 4 (Neu4). In certain embodiments, the sialidase is Neu2 or an enzymatically functional portion of Neu2. Accordingly, in some embodiments, a variant sialidase precursor protein comprises a heterologous secretory sequence operably linked to a sialidase or enzymatically functional portion thereof selected from Neu1, Neu2, Neu3, or Neu4. In certain embodiments, the sialidase is humanized.

In certain embodiments, a variant sialidase precursor protein comprises a sialidase or enzymatically functional portion thereof, wherein the sialidase comprises Neu2 comprising the amino acid sequence set forth in SEQ ID NO: 34 or 13, and may be encoded by the nucleotide sequence set forth in SEQ ID NO: 30 or 4. In certain embodiments, a variant sialidase precursor protein comprises a sialidase or enzymatically functional portion thereof, wherein the sialidase comprises Neu1 comprising the amino acid sequence set forth in SEQ ID NO: 33, and may be encoded by the nucleotide sequence set forth in SEQ ID NO: 29. In certain embodiments, a variant sialidase precursor protein comprises a sialidase or enzymatically functional portion thereof, wherein the sialidase comprises Neu3 comprising the amino acid sequence set forth in SEQ ID NO: 35, and may be encoded by the nucleotide sequence set forth in SEQ ID NO: 31. In certain embodiments, a variant sialidase precursor protein comprises a sialidase or enzymatically functional portion thereof, wherein the sialidase comprises Neu4 comprising the amino acid sequence set forth in SEQ ID NO: 36, and may be encoded by the nucleotide sequence set forth in SEQ ID NO: 32.

In some embodiments, a variant sialidase precursor protein comprises a heterologous secretory sequence operably linked to an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 33, 34, 35, or 36. In some embodiments, a variant sialidase precursor protein comprises a heterologous secretory sequence operably linked to an amino acid sequence comprising SEQ ID NO: 33, 34, 35, or 36. In some embodiments, a variant sialidase precursor protein comprises a heterologous secretory sequence operably linked to an amino acid sequence consisting of SEQ ID NO: 13, 33, 34, 35, or 36.

In some embodiments, a variant sialidase precursor protein comprises a heterologous secretory sequence operably linked to a sequence encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 29, 30, 31, or 32. In some embodiments, a variant sialidase precursor protein comprises a heterologous secretory sequence operably linked to a sequence encoded by a nucleic acid sequence comprising SEQ ID NO: 29, 30, 31, or 32. In some embodiments, a variant sialidase precursor protein comprises a heterologous secretory sequence operably linked to a sequence encoded by a nucleic acid sequence consisting of SEQ ID NO: 4, 29, 30, 31, or 32.

D. Modified Immune Cells

In one aspect, the present invention provides a modified immune cell or precursor thereof (e.g., a T cell) comprising a chimeric cell surface sialidase (neuraminidase) enzyme. The chimeric cell surface silidase comprises an extracellular portion comprising a sialidase (neuraminidase) or an enzymatically functional portion thereof, and a heterologous transmembrane domain capable of tethering the extracellular portion to a cell surface.

Also provided is a modified immune cell or precursor cell thereof, comprising a chimeric cell surface sialidase (neuraminidase) enzyme and a chimeric antigen receptor (CAR) and/or a T cell receptor (TCR). The chimeric cell surface silidase comprises an extracellular portion comprising a sialidase (neuraminidase) or an enzymatically functional portion thereof, and a heterologous transmembrane domain capable of tethering the extracellular portion to a cell surface.

In another aspect, the invention provides a modified immune cell or precursor cell thereof, comprising a variant sialidase precursor protein comprising a heterologous secretory sequence operably linked to a sialidase (neuraminidase) or an enzymatically functional portion thereof. The variant sialidase precursor protein lacks a transmembrane domain, and the sialidase or enzymatically functional portion thereof is capable of being secreted from an immune or precursor cell when the variant sialidase precursor protein is expressed in the cell.

Also provided is a modified immune cell or precursor cell thereof, comprising a variant sialidase precursor protein and a chimeric antigen receptor (CAR) and/or a T cell receptor (TCR). The variant sialidase precursor protein comprises a heterologous secretory sequence operably linked to a sialidase (neuraminidase) or an enzymatically functional portion thereof and lacks a transmembrane domain. The sialidase or enzymatically functional portion thereof is capable of being secreted from an immune or precursor cell thereof when the variant sialidase precursor protein is expressed in the cell.

The modified immune cells or precursor cells thereof may comprise any of the chimeric cell surface sialidase (neuraminidase) enzymes disclosed and described in detail elsewhere herein.

The modified immune cells or precursor cells thereof may comprise any of the CARs and/or any of the TCRs disclosed and described in detail elsewhere herein.

In one aspect, the invention includes a modified immune cell or precursor cell thereof, comprising a chimeric cell surface sialidase (neuraminidase) enzyme and a chimeric antigen receptor (CAR). The chimeric cell surface sialidase comprises an extracellular portion comprising Neu2 or an enzymatically functional portion thereof, and a heterologous transmembrane domain capable of tethering the extracellular portion to a cell surface.

In another aspect, the invention includes a modified immune cell or precursor cell thereof, comprising a chimeric cell surface sialidase (neuraminidase) enzyme and a chimeric antigen receptor (CAR) having specificity for TnMUC1, CD19, or PSMA. The chimeric cell surface sialidase comprises an extracellular portion comprising Neu2 or an enzymatically functional portion thereof, and a heterologous transmembrane domain capable of tethering the extracellular portion to a cell surface.

In yet another aspect, the invention includes a modified immune cell or precursor cell thereof, comprising a chimeric cell surface sialidase (neuraminidase) enzyme comprising an extracellular portion comprising Neu2 or an enzymatically functional portion thereof, a heterologous transmembrane domain capable of tethering the extracellular portion to a cell surface, a hinge domain, and an intracellular region comprising a costimulatory signaling domain and an intracellular signaling domain; and a chimeric antigen receptor (CAR).

In still another aspect, the invention includes a modified immune cell or precursor cell thereof, comprising: a chimeric cell surface sialidase (neuraminidase) enzyme comprising an extracellular portion comprising Neu2 or an enzymatically functional portion thereof, a heterologous transmembrane domain capable of tethering the extracellular portion to a cell surface, a hinge domain, and an intracellular region comprising a costimulatory signaling domain and an intracellular signaling domain; and a chimeric antigen receptor (CAR) having specificity for TnMUC1, CD19, or PSMA.

Another aspect of the invention includes a modified immune cell or precursor cell thereof, comprising a variant sialidase precursor protein and a chimeric antigen receptor (CAR) having specificity for TnMUC1, CD19, or PSMA. The variant sialidase precursor protein comprises a heterologous secretory sequence operably linked to a sialidase (neuraminidase) or an enzymatically functional portion thereof and lacks a transmembrane domain, and the sialidase or enzymatically functional portion thereof is capable of being secreted from an immune or precursor cell thereof when the variant sialidase precursor protein is expressed in the cell.

In certain embodiments, the modified cell is a modified immune cell. In certain embodiments, the modified cell is a modified T cell. In certain embodiments, the modified cell is an autologous cell. In certain embodiments, the modified cell is an autologous cell obtained from a human subject.

E. Chimeric Antigen Receptors

The present invention provides compositions and methods for modified immune cells or precursors thereof (e.g., modified T cells comprising a chimeric cell surface sialidase or a variant sialidase precursor protein), comprising a chimeric antigen receptor (CAR). Thus, in some embodiments, the immune cell has been genetically modified to express the CAR. CARs of the present invention comprise an antigen binding domain, a transmembrane domain, and an intracellular domain.

The antigen binding domain may be operably linked to another domain of the CAR, such as the transmembrane domain or the intracellular domain, both described elsewhere herein, for expression in the cell. In one embodiment, a first nucleic acid sequence encoding the antigen binding domain is operably linked to a second nucleic acid encoding a transmembrane domain, and further operably linked to a third a nucleic acid sequence encoding an intracellular domain.

The antigen binding domains described herein can be combined with any of the transmembrane domains described herein, any of the intracellular domains or cytoplasmic domains described herein, or any of the other domains described herein that may be included in a CAR of the present invention. A subject CAR of the present invention may also include a hinge domain as described herein. A subject CAR of the present invention may also include a spacer domain as described herein. In some embodiments, each of the antigen binding domain, transmembrane domain, and intracellular domain is separated by a linker.

Antigen Binding Domain

The antigen binding domain of a CAR is an extracellular region of the CAR for binding to a specific target antigen including proteins, carbohydrates, and glycolipids. In some embodiments, the CAR comprises affinity to a target antigen on a target cell. The target antigen may include any type of protein, or epitope thereof, associated with the target cell. For example, the CAR may comprise affinity to a target antigen on a target cell that indicates a particular disease state of the target cell.

In one embodiment, the target cell antigen is a tumor associated antigen (TAA). Examples of tumor associated antigens (TAAs), include but are not limited to, differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, 43-9F, 5T4, 791Tgp72, alpha-fetoprotein, beta-HCG, BCA225, BTAA, CA 125, CA 15-3CA 27.29BCAA, CA 195, CA 242, CA-50, CAM43, CD68P1, CO-029, FGF-5, G250, Ga733EpCAM, HTgp-175, M344, MA-50, MG7-Ag, MOV18, NB/70K, NY-CO-1, RCAS1, SDCCAG16, TA-90Mac-2 binding proteincy-clophilin C-associated protein, TAAL6, TAG72, TLP, and TPS. In a preferred embodiment, the antigen binding domain of the CAR targets an antigen that includes but is not limited to CD19, CD20, CD22, ROR1, Mesothelin, CD33/IL3Ra, c-Met, PSMA, PSCA, Glycolipid F77, EGFRvIII, GD-2, MY-ESO-1 TCR, MAGE A3 TCR, and the like.

Depending on the desired antigen to be targeted, the CAR of the invention can be engineered to include the appropriate antigen binding domain that is specific to the desired antigen target. For example, if CD19 is the desired antigen that is to be targeted, an antibody for CD19 can be used as the antigen bind moiety for incorporation into the CAR of the invention.

In one embodiment, the target cell antigen is TnMUC1. As such, in one embodiment, a CAR of the present disclosure has affinity for TnMUC1 on a target cell. In one embodiment, the target cell antigen is CD19. As such, in one embodiment, a CAR of the present disclosure has affinity for CD19 on a target cell. This should not be construed as limiting in any way, as a CAR having affinity for any target antigen is suitable for use in a composition or method of the present invention. In one embodiment, the target cell antigen is PSMA. As such, in one embodiment, a CAR of the present disclosure has affinity for PSMA on a target cell.

As described herein, a CAR of the present disclosure having affinity for a specific target antigen on a target cell may comprise a target-specific binding domain. In some embodiments, the target-specific binding domain is a murine target-specific binding domain, e.g., the target-specific binding domain is of murine origin. In some embodiments, the target-specific binding domain is a human target-specific binding domain, e.g., the target-specific binding domain is of human origin. In one embodiment, a CAR of the present disclosure having affinity for CD19 on a target cell may comprise a CD19 binding domain.

In some embodiments, a CAR of the present disclosure may have affinity for one or more target antigens on one or more target cells. In some embodiments, a CAR may have affinity for one or more target antigens on a target cell. In such embodiments, the CAR is a bispecific CAR, or a multispecific CAR. In some embodiments, the CAR comprises one or more target-specific binding domains that confer affinity for one or more target antigens. In some embodiments, the CAR comprises one or more target-specific binding domains that confer affinity for the same target antigen. For example, a CAR comprising one or more target-specific binding domains having affinity for the same target antigen could bind distinct epitopes of the target antigen. When a plurality of target-specific binding domains is present in a CAR, the binding domains may be arranged in tandem and may be separated by linker peptides. For example, in a CAR comprising two target-specific binding domains, the binding domains are connected to each other covalently on a single polypeptide chain, through an oligo- or polypeptide linker, an Fc hinge region, or a membrane hinge region.

In some embodiments, the antigen binding domain is selected from the group consisting of an antibody, an antigen binding fragment (Fab), and a single-chain variable fragment (scFv). In some embodiments, a TnMUC1 binding domain of the present invention is selected from the group consisting of a TnMUC1-specific antibody, a TnMUC1-specific Fab, and a TnMUC1-specific scFv. In one embodiment, a PSCA binding domain is a PSMA-specific antibody. In one embodiment, a PSMA binding domain is a PSMA-specific Fab. In one embodiment, a PSMA binding domain is a PSMA-specific scFv. In some embodiments, a CD19 binding domain of the present invention is selected from the group consisting of a CD19-specific antibody, a CD19-specific Fab, and a CD19-specific scFv. In one embodiment, a CD19 binding domain is a CD19-specific antibody. In one embodiment, a CD19 binding domain is a CD19-specific Fab. In one embodiment, a CD19 binding domain is a CD19-specific scFv.

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. In some embodiments, the antigen binding domain portion comprises a mammalian antibody or a fragment thereof. The choice of antigen binding domain may depend upon the type and number of antigens that are present on the surface of a target cell.

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker, which connects the N-terminus of the VH with the C-terminus of the VL, or the C-terminus of the VH with the N-terminus of the VL. In some embodiments, the antigen binding domain (e.g., PSCA binding domain) comprises an scFv having the configuration from N-terminus to C-terminus, VH-linker-VL. In some embodiments, the antigen binding domain comprises an scFv having the configuration from N-terminus to C-terminus, VL-linker-VH. Those of skill in the art would be able to select the appropriate configuration for use in the present invention.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. Various linker sequences are known in the art, including, without limitation, glycine serine (GS) linkers such as $(GS)_n$, $(GSGGS)_n$ (SEQ ID NO:12), $(GGGS)_n$ (SEQ ID NO:14), and $(GGGGS)_n$ (SEQ ID NO:48), where n represents an integer of at least 1. Exemplary linker sequences can comprise amino acid sequences including, without limitation, GGSG (SEQ ID NO:3), GGSGG (SEQ ID NO:5), GSGSG (SEQ ID NO:41), GSGGG (SEQ ID NO:42), GGGSG (SEQ ID NO:43), GSSSG (SEQ ID NO:44), GGGGS (SEQ ID NO:45), GGGGSGGGGSGGGGS (SEQ ID NO:46) and the like. Those of skill in the art would be able to select the appropriate linker sequence for use in the present invention. In one embodiment, an antigen binding domain of the present invention comprises a heavy chain variable region (VH) and a light chain variable region (VL), wherein the VH and VL is separated by the linker sequence having the amino acid sequence GGGGSGGGGSGGGGS (SEQ ID NO:46), which may be encoded by the nucleic acid sequence (SEQ ID NO: 47)

GGTGGCGGTGGCTCGGGCGGTGGTGGGTCGGGTGGCGGCGGATCT.

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2 (10:31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immunol 1997 17 (5-6):427-55; Ho et al., BioChim Biophys Acta 2003 1638(3):257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

In some embodiments, the antigen binding domain may be derived from the same species in which the CAR will ultimately be used. For example, for use in humans, the antigen binding domain of the CAR may comprise a human antibody or a fragment thereof. In some embodiments, the antigen binding domain may be derived from a different species in which the CAR will ultimately be used. For example, for use in humans, the antigen binding domain of the CAR may comprise a murine antibody or a fragment thereof.

Transmembrane Domain

CARs of the present invention may comprise a transmembrane domain that connects the antigen binding domain of the CAR to the intracellular domain of the CAR. The transmembrane domain of a subject CAR is a region that is capable of spanning the plasma membrane of a cell (e.g., an immune cell or precursor thereof). The transmembrane domain is for insertion into a cell membrane, e.g., a eukaryotic cell membrane. In some embodiments, the transmembrane domain is interposed between the antigen binding domain and the intracellular domain of a CAR.

In some embodiments, the transmembrane domain is naturally associated with one or more of the domains in the CAR. In some embodiments, the transmembrane domain can be selected or modified by one or more amino acid substitutions to avoid binding of such domains to the transmembrane domains of the same or different surface membrane proteins, to minimize interactions with other members of the receptor complex.

The transmembrane domain may be derived either from a natural or a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the CAR into a cell membrane, e.g., an artificial hydrophobic sequence. Examples of the transmembrane domain of particular use in this invention include, without limitation, transmembrane domains derived from (i.e. comprise at least the transmembrane region(s) of) the alpha, beta or zeta chain of the T cell receptor, CD28, CD3 epsilon, CD45, CD4, CD5, CD7, CD8, CD9, CD16, CD22, CD33, CD37, CD64, CD80, CD86, CD134 (OX-40), CD137 (4-1BB), CD154 (CD40L), Toll-like receptor 1 (TLR1), TLR2, TLR3, TLR4, TLR5, TLR6, TLR7, TLR8, and TLR9. In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

The transmembrane domains described herein can be combined with any of the antigen binding domains described herein, any of the intracellular domains described herein, or any of the other domains described herein that may be included in a subject CAR.

In some embodiments, the transmembrane domain further comprises a hinge region. A subject CAR of the present invention may also include a hinge region. The hinge region of the CAR is a hydrophilic region which is located between the antigen binding domain and the transmembrane domain. In some embodiments, this domain facilitates proper protein folding for the CAR. The hinge region is an optional component for the CAR. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4).

In some embodiments, a subject CAR of the present disclosure includes a hinge region that connects the antigen binding domain with the transmembrane domain, which, in turn, connects to the intracellular domain. The hinge region is preferably capable of supporting the antigen binding domain to recognize and bind to the target antigen on the target cells (see, e.g., Hudecek et al., *Cancer Immunol. Res.* (2015) 3(2): 125-135). In some embodiments, the hinge region is a flexible domain, thus allowing the antigen binding domain to have a structure to optimally recognize the specific structure and density of the target antigens on a cell such as tumor cell (Hudecek et al., supra). The flexibility of the hinge region permits the hinge region to adopt many different conformations.

In some embodiments, the hinge region is an immunoglobulin heavy chain hinge region. In some embodiments, the hinge region is a hinge region polypeptide derived from a receptor (e.g., a CD8-derived hinge region).

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa. In some embodiments, the hinge region can have a length of greater than 5 aa, greater than 10 aa, greater than 15 aa, greater than 20 aa, greater than 25 aa, greater than 30 aa, greater than 35 aa, greater than 40 aa, greater than 45 aa, greater than 50 aa, greater than 55 aa, or more.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids. Suitable hinge regions can have a length of greater than 20 amino acids (e.g., 30, 40, 50, 60 or more amino acids).

For example, hinge regions include glycine polymers $(G)_n$, glycine-serine polymers (including, for example, $(GS)_n$, $(GSGGS)_n$ (SEQ ID NO:12) and $(GGGS)_n$(SEQ ID NO:14), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, *Rev. Computational. Chem.* (1992) 2: 73-142). Exemplary hinge regions can comprise amino acid sequences including, but not limited to, GGSG (SEQ ID NO:3), GGSGG (SEQ ID NO:5), GSGSG (SEQ ID NO:41), GSGGG (SEQ ID NO:42), GGGSG (SEQ ID NO:43), GSSSG (SEQ ID NO:44), and the like.

In some embodiments, the hinge region is an immunoglobulin heavy chain hinge region. Immunoglobulin hinge region amino acid sequences are known in the art; see, e.g., Tan et al., *Proc. Natl. Acad. Sci. USA* (1990) 87(1):162-166; and Huck et al., *Nucleic Acids Res.* (1986) 14(4): 1779-1789. As non-limiting examples, an immunoglobulin hinge region can include one of the following amino acid sequences: DKTHT (SEQ ID NO:49); CPPC (SEQ ID NO:50); CPEPKSCDTPPPCPR (SEQ ID NO:51) (see, e.g., Glaser et al., *J. Biol. Chem.* (2005) 280:41494-41503); ELKTPLGDTTHT (SEQ ID NO:52); KSCDKTHTCP (SEQ ID NO:53); KCCVDCP (SEQ ID NO:54); KYGPPCP (SEQ ID NO:55); EPKSCDKTHTCPPCP (SEQ ID NO:56) (human IgG1 hinge); ERKCCVECPPCP (SEQ ID NO:57) (human IgG2 hinge); ELKTPLGDTTHTCPRCP (SEQ ID NO:58) (human IgG3 hinge); SPNMVPHAHHAQ (SEQ ID NO:59) (human IgG4 hinge); and the like.

The hinge region can comprise an amino acid sequence of a human IgG1, IgG2, IgG3, or IgG4, hinge region. In one embodiment, the hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO:116); see, e.g., Yan et al., *J. Biol. Chem.* (2012) 287: 5891-5897. In one embodiment, the hinge region can comprise an amino acid sequence derived from human CD8, or a variant thereof.

Intracellular Region

A subject CAR of the present invention also includes an intracellular region. The intracellular region comprises a costimulatory signaling domain and an intracellular signaling domain". The intracellular region of the CAR is responsible for activation of at least one of the effector functions of the cell in which the CAR is expressed (e.g., immune cell). The intracellular region transduces the effector function signal and directs the cell (e.g., immune cell) to perform its specialized function, e.g., harming and/or destroying a target cell.

Examples of an intracellular region for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular signaling domain include, without limitation, the ζ chain of the T cell receptor complex or any of its homologs, e.g., η chain, FcsRIγ and β chains, MB 1 (Iga) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular signaling domain may be human CD3 zeta chain, FcyRIII, FcsRI, cytoplasmic tails of Fc receptors, an immunoreceptor tyrosine-based activation motif (ITAM) bearing cytoplasmic receptors, and combinations thereof.

In one embodiment, the costimulatory signaling domain of the CAR includes any portion of one or more co-stimulatory molecules, such as at least one signaling domain from CD2, CD3, CD8, CD27, CD28, ICOS, 4-1BB, PD-1, any derivative or variant thereof, any synthetic sequence thereof that has the same functional capability, and any combination thereof.

Other examples of the costimulatory signaling domain include a fragment or domain from one or more molecules or receptors including, but not limited to, TCR, CD3 zeta, CD3 gamma, CD3 delta, CD3 epsilon, CD86, common FcR gamma, FcR beta (Fc Epsilon RIb), CD79a, CD79b, Fcgamma RIIa, DAP10, DAP12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CDlib, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAMI, CRT AM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) super-family receptors (see, e.g., Park and Brentjens, J. Clin. Oncol. (2015) 33(6): 651-653). Additionally, intracellular signaling domains may include signaling domains used by NK and NKT cells (see, e.g., Hermanson and Kaufman, Front. Immunol. (2015) 6: 195) such as signaling domains of NKp30 (B7-H6) (see, e.g., Zhang et al., J. Immunol. (2012) 189(5): 2290-2299), and DAP 12 (see, e.g., Topfer et al., J. Immunol. (2015) 194(7): 3201-3212), NKG2D, NKp44, NKp46, DAP10, and CD3z.

Intracellular signaling domains suitable for use in a subject CAR of the present invention include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In some embodiments, the intracellular signaling domain includes at least one (e.g., one, two, three, four, five, six, etc.) ITAM motifs as described below. In some embodiments, the intracellular signaling domain includes DAP10/CD28 type signaling chains. In some embodiments, the intracellular signaling domain is not covalently attached to the membrane bound CAR, but is instead diffused in the cytoplasm.

Intracellular signaling domains suitable for use in a subject CAR of the present invention include immunoreceptor tyrosine-based activation motif (ITAM)-containing intracellular signaling polypeptides. In some embodiments, an ITAM motif is repeated twice in an intracellular signaling domain, where the first and second instances of the ITAM motif are separated from one another by 6 to 8 amino acids. In one embodiment, the intracellular signaling domain of a subject CAR comprises 3 ITAM motifs.

In some embodiments, intracellular signaling domains includes the signaling domains of human immunoglobulin receptors that contain immunoreceptor tyrosine based activation motifs (ITAMs) such as, but not limited to, FcgammaRI, FcgammaRIIA, FcgammaRIIC, FcgammaRIIIA, FcRL5 (see, e.g., Gillis et al., Front. Immunol. (2014) 5:254).

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12, FCER1G (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In one embodiment, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular signaling domain is derived from FCER1G (also known as FCRG; Fe epsilon receptor I gamma chain; Fc receptor gamma-chain; fc-epsilon RI-gamma; fcRgamma; fceR1 gamma; high affinity immunoglobulin epsilon receptor subunit gamma; immunoglobulin E receptor, high affinity, gamma chain; etc.). In one embodiment, the intracellular signaling domain is derived from T-cell surface glycoprotein CD3 delta chain (also known as CD3D; CD3-DELTA; T3D;

CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In one embodiment, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In one embodiment, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). In one embodiment, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). In one embodiment, the intracellular signaling domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In one embodiment, an intracellular signaling domain suitable for use in an FN3 CAR of the present disclosure includes a DAP10/CD28 type signaling chain. In one embodiment, an intracellular signaling domain suitable for use in an FN3 CAR of the present disclosure includes a ZAP70 polypeptide. In some embodiments, the intracellular signaling domain includes a cytoplasmic signaling domain of TCR zeta, FcR gamma, FcR beta, CD3 gamma, CD3 delta, CD3 epsilon, CD5, CD22, CD79a, CD79b, or CD66d. In one embodiment, the intracellular signaling domain in the CAR includes a cytoplasmic signaling domain of human CD3 zeta.

While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The intracellular signaling domain includes any truncated portion of the intracellular signaling domain sufficient to transduce the effector function signal.

The intracellular regions described herein can be combined with any of the antigen binding domains described herein, any of the transmembrane domains described herein, or any of the other domains described herein that may be included in the CAR.

F. T Cell Receptors

The present invention provides compositions and methods for modified immune cells or precursors thereof (e.g., modified T cells comprising a chimeric cell surface sialidase or a variant sialidase precursor protein) comprising a T cell receptor (TCR). In some embodiments, the cell has been altered to contain specific T cell receptor (TCR) genes (e.g., a nucleic acid encoding an alpha/beta TCR). TCRs or antigen-binding portions thereof include those that recognize a peptide epitope or T cell epitope of a target polypeptide, such as an antigen of a tumor, viral or autoimmune protein. In certain embodiments, the TCR has binding specificity for a tumor associated antigen, e.g., human NY-ESO-1.

A TCR is a disulfide-linked heterodimeric protein comprised of six different membrane bound chains that participate in the activation of T cells in response to an antigen.

There exists alpha/beta TCRs and gamma/delta TCRs. An alpha/beta TCR comprises a TCR alpha chain and a TCR beta chain. T cells expressing a TCR comprising a TCR alpha chain and a TCR beta chain are commonly referred to as alpha/beta T cells. Gamma/delta TCRs comprise a TCR gamma chain and a TCR delta chain. T cells expressing a TCR comprising a TCR gamma chain and a TCR delta chain are commonly referred to as gamma/delta T cells. A TCR of the present disclosure is a TCR comprising a TCR alpha chain and a TCR beta chain.

The TCR alpha chain and the TCR beta chain are each comprised of two extracellular domains, a variable region and a constant region. The TCR alpha chain variable region and the TCR beta chain variable region are required for the affinity of a TCR to a target antigen. Each variable region comprises three hypervariable or complementarity-determining regions (CDRs) which provide for binding to a target antigen. The constant region of the TCR alpha chain and the constant region of the TCR beta chain are proximal to the cell membrane. A TCR further comprises a transmembrane region and a short cytoplasmic tail. CD3 molecules are assembled together with the TCR heterodimer. CD3 molecules comprise a characteristic sequence motif for tyrosine phosphorylation, known as immunoreceptor tyrosine-based activation motifs (ITAMs). Proximal signaling events are mediated through the CD3 molecules, and accordingly, TCR-CD3 complex interaction plays an important role in mediating cell recognition events.

Stimulation of TCR is triggered by major histocompatibility complex molecules (MHCs) on antigen presenting cells that present antigen peptides to T cells and interact with TCRs to induce a series of intracellular signaling cascades. Engagement of the TCR initiates both positive and negative signaling cascades that result in cellular proliferation, cytokine production, and/or activation-induced cell death.

A TCR of the present invention can be a wild-type TCR, a high affinity TCR, and/or a chimeric TCR. A high affinity TCR may be the result of modifications to a wild-type TCR that confers a higher affinity for a target antigen compared to the wild-type TCR. A high affinity TCR may be an affinity-matured TCR. Methods for modifying TCRs and/or the affinity-maturation of TCRs are known to those of skill in the art. Techniques for engineering and expressing TCRs include, but are not limited to, the production of TCR heterodimers which include the native disulphide bridge which connects the respective subunits (Garboczi, et al., (1996), Nature 384(6605): 134-41; Garboczi, et al., (1996), J Immunol 157(12): 5403-10; Chang et al., (1994), PNAS USA 91: 11408-11412; Davodeau et al., (1993), J. Biol. Chem. 268(21): 15455-15460; Golden et al., (1997), J. Imm. Meth. 206: 163-169; U.S. Pat. No. 6,080,840).

In some embodiments, the exogenous TCR is a full TCR or an antigen-binding portion or antigen-binding fragment thereof. In some embodiments, the TCR is an intact or full-length TCR, including TCRs in the αβ form or Γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions (CDRs) involved in recognition of the peptide, MHC and/or MHC-peptide complex.

In some embodiments, the variable domains of the TCR contain hypervariable loops, or CDRs, which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al, Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR contains a variable alpha domain ($V_\alpha$) and/or a variable beta domain ($V_\beta$) or antigen-binding fragments thereof. In some embodiments, the α-chain and/or β-chain of a TCR also can contain a constant domain, a transmembrane domain and/or a short cytoplasmic tail (see, e.g., Janeway et al., Immunobiology: The Immune System in Health and Disease, 3 Ed., *Current Biology Publications*, p. 4:33, 1997). In some embodiments, the α chain constant domain is encoded by the TRAC gene (IMGT nomenclature) or is a variant thereof. In some embodiments, the β chain constant region is encoded by TRBC1 or TRBC2 genes (IMGT nomenclature) or is a variant thereof. In some embodiments, the constant domain is adjacent to the cell membrane. For example, in some cases, the extracellular portion of the TCR formed by the two chains contains two membrane-proximal constant domains, and two membrane-distal variable domains, which variable domains each contain CDRs.

It is within the level of a skilled artisan to determine or identify the various domains or regions of a TCR. In some aspects, residues of a TCR are known or can be identified according to the International Immunogenetics Information System (IMGT) numbering system (see e.g. www.imgt.org; see also, Lefranc et al. (2003) Developmental and Comparative Immunology, 2&; 55-77; and The T Cell Factsbook 2nd Edition, Lefranc and LeFranc Academic Press 2001). Using this system, the CDR1 sequences within a TCR Va chain and/or Vβ chain correspond to the amino acids present between residue numbers 27-38, inclusive, the CDR2 sequences within a TCR Va chain and/or Vβ chain correspond to the amino acids present between residue numbers 56-65, inclusive, and the CDR3 sequences within a TCR Va chain and/or Vβ chain correspond to the amino acids present between residue numbers 105-117, inclusive. The IMGT numbering system should not be construed as limiting in any way, as there are other numbering systems known to those of skill in the art, and it is within the level of the skilled artisan to use any of the numbering systems available to identify the various domains or regions of a TCR.

In some embodiments, the TCR may be a heterodimer of two chains α and β (or optionally γ and δ) that are linked, such as by a disulfide bond or disulfide bonds. In some embodiments, the constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains. In some embodiments, each of the constant and variable domains contain disulfide bonds formed by cysteine residues.

In some embodiments, the TCR for engineering cells as described is one generated from a known TCR sequence(s), such as sequences of Va, chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences. In some embodiments, the TCR is obtained from a biological source, such as from cells such as from a T cell (e.g. cytotoxic T cell), T cell hybridomas or other publicly available source. In some embodiments, the T cells can be obtained from in vivo isolated cells. In some embodiments, the T-cells can be a cultured T cell hybridoma or clone. In some embodiments, the TCR or antigen-binding portion thereof can be synthetically generated from knowledge of the sequence of the TCR. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15: 169-180 and Cohen et al. (2005) J Immunol. 175:5799-5808. In some embodiments, phage display is used to isolate TCRs against a target antigen (see, e.g., Varela-Rohena et al. (2008) Nat Med. 14: 1390-1395 and Li (2005) Nat Biotechnol. 23:349-354.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which one or more residues of the CDRs are mutated, and mutants with an desired altered property, such as higher affinity for a desired target antigen, are selected.

In some embodiments as described, the TCR can contain an introduced disulfide bond or bonds. In some embodiments, the native disulfide bonds are not present. In some embodiments, the one or more of the native cysteines (e.g. in the constant domain of the α chain and β chain) that form a native interchain disulfide bond are substituted with another residue, such as with a serine or alanine. In some embodiments, an introduced disulfide bond can be formed by mutating non-cysteine residues on the alpha and beta chains, such as in the constant domain of the α chain and β chain, to cysteine. Exemplary non-native disulfide bonds of a TCR are described in published International PCT No. WO2006/000830 and WO2006/037960. In some embodiments, cysteines can be introduced at residue Thr48 of the α chain and Ser57 of the β chain, at residue Thr45 of the α chain and Ser77 of the β chain, at residue Tyr10 of the α chain and Ser17 of the β chain, at residue Thr45 of the α chain and Asp59 of the β chain and/or at residue Ser15 of the α chain and Glu15 of the β chain. In some embodiments, the presence of non-native cysteine residues (e.g. resulting in one or more non-native disulfide bonds) in a recombinant TCR can favor production of the desired recombinant TCR in a cell in which it is introduced over expression of a mismatched TCR pair containing a native TCR chain.

In some embodiments, the TCR chains contain a transmembrane domain. In some embodiments, the transmembrane domain is positively charged. In some cases, the TCR chain contains a cytoplasmic tail. In some aspects, each chain (e.g. alpha or beta) of the TCR can possess one N-terminal immunoglobulin variable domain, one immunoglobulin constant domain, a transmembrane region, and a short cytoplasmic tail at the C-terminal end. In some embodiments, a TCR, for example via the cytoplasmic tail, is associated with invariant proteins of the CD3 complex involved in mediating signal transduction. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3y, CD35, CD3s and CD3ζ chains) contain one or more immunoreceptor tyrosine-based activation motif or IT AM that are involved in the signaling capacity of the TCR complex.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). A TCR may be cell-bound or in soluble form. In some embodiments, for purposes of the provided methods, the TCR is in cell-bound form expressed on the surface of a cell. In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native interchain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane. In some embodiments, a dTCR contains a TCR α chain containing a variable α domain, a constant α domain and a first dimerization motif attached to the C-terminus of the constant α domain, and a TCR β chain comprising a variable R domain, a constant β domain and a first dimerization motif attached to the C-terminus of the constant R domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR, which is a single amino acid strand containing an α chain and a β chain that is able to bind to MHC-peptide complexes. Typically, a scTCR can be generated using methods known to those of skill in the art, See e.g., International published PCT Nos. WO 96/13593, WO 96/18105, WO99/18129, WO04/033685, WO2006/037960, WO2011/044186; U.S. Pat. No. 7,569,664; and Schlueter, C. J. et al. J. Mol. Biol. 256, 859 (1996). In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment. In some embodiments, a scTCR contains a first segment constituted by an amino acid sequence corresponding to a TCR β chain variable region, a second segment constituted by an amino acid sequence corresponding to a TCR α chain variable region sequence fused to the N terminus of an amino acid sequence corresponding to a TCR α chain constant domain extracellular sequence, and a linker sequence linking the C terminus of the first segment to the N terminus of the second segment. In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment. In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence comprising an α chain extracellular constant domain sequence and transmembrane sequence, and, optionally, a linker sequence linking the C terminus of the first segment to the N terminus of the second segment. In some embodiments, for the scTCR to bind an MHC-peptide complex, the α and β chains must be paired so that the variable region sequences thereof are orientated for such binding. Various methods of promoting pairing of an α and β in a scTCR are well known in the art. In some embodiments, a linker sequence is included that links the α and β chains to form the single polypeptide strand. In some embodiments, the linker should have sufficient length to span the distance between the C terminus of the α chain and the N terminus of the β chain, or vice versa, while also ensuring that the linker length is not so long so that it blocks or reduces bonding of the scTCR to the target peptide-MHC complex. In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P-, wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, a scTCR contains a disulfide bond between residues of the single amino acid strand, which, in some cases, can promote stability of the pairing between the α and β regions of the single chain molecule (see e.g. U.S. Pat. No. 7,569,664). In some embodiments, the scTCR contains a covalent disulfide bond linking a residue of the immunoglobulin region of the constant domain of the α immunoglobulin region of the constant domain of the α chain to a residue of the immunoglobulin region of the constant domain of the β chain of the single chain molecule. In some embodiments, the disulfide bond corresponds to the native disulfide bond present in a native dTCR. In some embodiments, the disulfide bond in a native TCR is not present. In some embodiments, the disulfide bond is an introduced non-native disulfide bond, for example, by incorporating one or more cysteines into the constant region extracellular sequences of the first and second chain regions of the scTCR polypeptide. Exemplary cysteine mutations include any as described above. In some cases, both a native and a non-native disulfide bond may be present.

In some embodiments, any of the TCRs, including a dTCR or scTCR, can be linked to signaling domains that yield an active TCR on the surface of a T cell. In some embodiments, the TCR is expressed on the surface of cells. In some embodiments, the TCR does contain a sequence corresponding to a transmembrane sequence. In some embodiments, the transmembrane domain can be a Ca or CP transmembrane domain. In some embodiments, the transmembrane domain can be from a non-TCR origin, for example, a transmembrane region from CD3z, CD28 or B7.1. In some embodiments, the TCR does contain a sequence corresponding to cytoplasmic sequences. In some embodiments, the TCR contains a CD3z signaling domain. In some embodiments, the TCR is capable of forming a TCR complex with CD3. In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal.

In some embodiments, the TCR comprises affinity to a target antigen on a target cell. The target antigen may include any type of protein, or epitope thereof, associated with the target cell. For example, the TCR may comprise affinity to a target antigen on a target cell that indicates a particular disease state of the target cell. In some embodiments, the target antigen is processed and presented by MHCs.

In one embodiment, the target cell antigen is a New York esophageal-1 (NY-ESO-1) peptide. NY-ESO-1 belongs to the cancer-testis (CT) antigen group of proteins. NY-ESO-1 is a highly immunogenic antigen in vitro and is presented to T cells via the MHC. CTLs recognizing the A2 presented epitope NY-ESO$_{157-165}$, SLLMWITQC (SEQ ID NO:60), have been grown from the blood and lymph nodes of myeloma patients. T cell clones specific for this epitope have been shown to kill tumor cells. A high affinity TCR recognizing the NY-ESO$_{157-165}$ epitope may recognize HLA-A2-positive, NY-ESO-1 positive cell lines (but not to cells that lack either HLA-A2 or NY-ESO). Accordingly, a TCR of the present disclosure may be a HLA-A2-restricted NY-ESO-1 (SLLMWITQC; SEQ ID NO:60)-specific TCR. In one embodiment, an NY-ESO-1 TCR of the present disclosure is a wild-type NY-ESO-1 TCR. A wild-type NY-ESO-1 TCR may include, without limitation, the 8F NY-ESO-1 TCR (also referred to herein as "8F" or "8F TCR"), and the 1G4 NY-ESO-1 TCR (also referred to herein as "1G4" or "1G4 TCR"). In one embodiment, an NY-ESO-1 TCR of the present disclosure is an affinity enhanced 1G4 TCR, also called Ly95. 1G4 TCR and affinity enhanced 1G4 TCR is described in U.S. Pat. No. 8,143,376. This should not be construed as limiting in any way, as a TCR having affinity for any target antigen is suitable for use in a composition or method of the present invention.

The TCR alpha chain coding sequence and the TCR beta chain coding sequence may be separated by a linker. In certain embodiments, the linker comprises a nucleic acid sequence encoding an internal ribosome entry site (IRES), a furin cleavage site, a self-cleaving peptide, or any combination thereof. In certain embodiments, the first linker comprises a furin cleavage site and a self-cleaving peptide. In certain embodiments, the self-cleaving peptide is a 2A peptide selected from the group consisting of porcine teschovirus-1 2A (P2A), Thoseaasigna virus 2A (T2A), equine rhinitis A virus 2A (E2A), and foot-and-mouth disease virus 2A (F2A).

G. Nucleic Acids and Expression Vectors

The present disclosure provides a nucleic acid comprising a nucleic acid sequence encoding a chimeric cell surface sialidase (neuraminidase) enzyme. Also provided is a nucleic acid comprising a nucleic acid sequence encoding a variant sialidase precursor protein.

In one embodiment, a nucleic acid of the present disclosure further comprises a nucleic acid sequence encoding an exogenous TCR (e.g., an NY-ESO-1 TCR). In one embodiment, a nucleic acid of the present disclosure further comprises a nucleic acid sequence encoding an exogenous CAR (e.g., a PSMA CAR).

In certain embodiments, a nucleic acid of the present disclosure comprises a first nucleic acid encoding a chimeric cell surface sialidase and a second nucleic acid sequence encoding an exogenous TCR. In certain embodiments, a nucleic acid of the present disclosure comprises a first nucleic acid encoding a chimeric cell surface sialidase and a second nucleic acid sequence encoding an exogenous CAR. In certain embodiments, a nucleic acid of the present disclosure comprises a first nucleic acid encoding a chimeric cell surface sialidase and a second nucleic acid sequence encoding an exogenous TCR and an exogenous CAR.

In certain embodiments, a nucleic acid of the present disclosure comprises a first nucleic acid sequence encoding a variant sialidase precursor protein and a second nucleic acid sequence encoding an exogenous TCR. In certain embodiments, a nucleic acid of the present disclosure comprises a first nucleic acid sequence encoding a variant sialidase precursor protein and a second nucleic acid sequence encoding an exogenous CAR. In certain embodiments, a nucleic acid of the present disclosure comprises a first nucleic acid sequence encoding a variant sialidase precursor protein and a second nucleic acid sequence encoding an exogenous TCR and an exogeneous CAR.

In certain embodiments, the first nucleic acid sequence and the second nucleic acid sequence are separated by a linker.

In some embodiments, the linker comprises a nucleic acid sequence that encodes for an internal ribosome entry site (IRES). As used herein, "an internal ribosome entry site" or "IRES" refers to an element that promotes direct internal ribosome entry to the initiation codon, such as ATG, of a protein coding region, thereby leading to cap-independent translation of the gene. Various internal ribosome entry sites are known to those of skill in the art, including, without limitation, IRES obtainable from viral or cellular mRNA sources, e.g., immunoglobulin heavy-chain binding protein (BiP); vascular endothelial growth factor (VEGF); fibroblast growth factor 2; insulin-like growth factor; translational initiation factor eIF4G; yeast transcription factors TFIID and HAP4; and IRES obtainable from, e.g., cardiovirus, rhinovirus, aphthovirus, HCV, Friend murine leukemia virus (FrMLV), and Moloney murine leukemia virus (MoMLV). Those of skill in the art would be able to select the appropriate IRES for use in the present invention.

In some embodiments, the linker comprises a nucleic acid sequence that encodes for a self-cleaving peptide. As used herein, a "self-cleaving peptide" or "2A peptide" refers to an oligopeptide that allow multiple proteins to be encoded as polyproteins, which dissociate into component proteins upon translation. Use of the term "self-cleaving" is not intended to imply a proteolytic cleavage reaction. Various self-cleaving or 2A peptides are known to those of skill in the art, including, without limitation, those found in members of the Picornaviridae virus family, e.g., foot-and-mouth disease virus (FMDV), equine rhinitis A virus (ERAVO, Thosea asigna virus (TaV), and porcine tescho virus-1 (PTV-1); and carioviruses such as Theilovirus and encephalomyocarditis viruses. 2A peptides derived from FMDV, ERAV, PTV-1, and TaV are referred to herein as "F2A," "E2A," "P2A," and "T2A," respectively. Those of skill in the art would be able to select the appropriate self-cleaving peptide for use in the present invention.

In some embodiments, a linker further comprises a nucleic acid sequence that encodes a furin cleavage site. Furin is a ubiquitously expressed protease that resides in the trans-golgi and processes protein precursors before their secretion. Furin cleaves at the COOH— terminus of its consensus recognition sequence. Various furin consensus recognition sequences (or "furin cleavage sites") are known to those of skill in the art, including, without limitation, Arg-X1-Lys-Arg (SEQ ID NO:117) or Arg-X1-Arg-Arg (SEQ ID NO:118), X2-Arg-X1-X3-Arg (SEQ ID NO:119) and Arg-X1-X1-Arg (SEQ ID NO:120), such as an Arg-Gln-Lys-Arg (SEQ ID NO:121), where X1 is any naturally occurring amino acid, X2 is Lys or Arg, and X3 is Lys or Arg. Those of skill in the art would be able to select the appropriate Furin cleavage site for use in the present invention.

In some embodiments, the linker comprises a nucleic acid sequence encoding a combination of a Furin cleavage site and a 2A peptide. Examples include, without limitation, a linker comprising a nucleic acid sequence encoding Furin and F2A, a linker comprising a nucleic acid sequence encoding Furin and E2A, a linker comprising a nucleic acid sequence encoding Furin and P2A, a linker comprising a nucleic acid sequence encoding Furin and T2A. Those of skill in the art would be able to select the appropriate combination for use in the present invention. In such embodiments, the linker may further comprise a spacer sequence between the Furin and 2A peptide. Various spacer sequences are known in the art, including, without limitation, glycine serine (GS) spacers such as (GS)n, (GSGGS)n (SEQ ID NO:12) and (GGGS)n (SEQ ID NO:14), where n represents an integer of at least 1. Exemplary spacer sequences can comprise amino acid sequences including, without limitation, GGSG (SEQ ID NO:3), GGSGG (SEQ ID NO:5), GSGSG (SEQ ID NO:41), GSGGG (SEQ ID NO:42), GGGSG (SEQ ID NO:43), GSSSG (SEQ ID NO:44), and the like. Those of skill in the art would be able to select the appropriate spacer sequence for use in the present invention.

In some embodiments, a nucleic acid of the present disclosure is provided for the production of a chimeric cell surface sialidase or a variant sialidase precursor protein or a TCR or a CAR as described herein, e.g., in a mammalian cell. In some embodiments, a nucleic acid of the present disclosure provides for amplification of the sialidase- or TCR- or CAR-encoding nucleic acid.

As described herein, a TCR of the present disclosure comprises a TCR alpha chain and a TCR beta chain. Accordingly, the present disclosure provides a nucleic acid encoding a TCR alpha chain, and a nucleic acid encoding a TCR beta chain. In some embodiments, the nucleic acid encoding a TCR alpha chain is separate from the nucleic acid encoding a TCR beta chain. In an exemplary embodiment, the nucleic acid encoding a TCR alpha chain, and the nucleic acid encoding a TCR beta chain, resides within the same nucleic acid.

In some embodiments, a nucleic acid of the present disclosure comprises a nucleic acid comprising a TCR alpha chain coding sequence and a TCR beta chain coding sequence. In some embodiments, a nucleic acid of the present disclosure comprises a nucleic acid comprising a TCR alpha chain coding sequence and a TCR beta chain coding sequence that is separated by a linker. A linker for use in the present disclosure allows for multiple proteins to be encoded by the same nucleic acid sequence (e.g., a multicistronic or bicistronic sequence), which are translated as a polyprotein that is dissociated into separate protein components. For example, a linker for use in a nucleic acid of the present disclosure comprising a TCR alpha chain coding sequence and a TCR beta chain coding sequence, allows for the TCR alpha chain and TCR beta chain to be translated as a polyprotein that is dissociated into separate TCR alpha chain and TCR beta chain components.

In some embodiments, a nucleic acid of the present disclosure may comprise a leader sequence. Suitable leader sequences are known to those of skill in the art. In one embodiment, the leader sequence is a CD8 alpha leader sequence. In one embodiment, the leader sequence is encoded by a nucleic acid sequence comprising SEQ ID NO: 2.

In some embodiments, a nucleic acid of the present disclosure may be operably linked to a transcriptional control element, e.g., a promoter, and enhancer, etc. Suitable promoter and enhancer elements are known to those of skill in the art.

In certain embodiments, the nucleic acid is in operable linkage with a promoter. In certain embodiments, the promoter is a phosphoglycerate kinase-1 (PGK) promoter.

For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. Proc. Natl. Acad. Sci. USA (1993) 90:7739; and Marodon et al. (2003) Blood 101:3416. As another example, a CD8 gene promoter can be used. NK cell-specific expression can be achieved by use of an NcrI (p46) promoter; see, e.g., Eckelhart et al. Blood (2011) 117:1565.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in Pichia). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173(1): 86-93; Alpuche-Aranda et al., Proc. Natl. Acad. Sci. USA (1992) 89(21): 10079-83), a nirB promoter (Harborne et al. Mol. Micro. (1992) 6:2805-2813), and the like (see, e.g., Dunstan et al., Infect. Immun. (1999) 67:5133-5141; McKelvie et al., Vaccine (2004) 22:3243-3255; and Chatfield et al., Biotechnol. (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al., Infect. Immun. (2002) 70:1087-1096); an rpsM promoter (see, e.g., Valdivia and Falkow Mol. Microbiol. (1996). 22:367); a tet promoter (see, e.g., Hillen, W. and Wissmann, A. (1989) In Saenger, W. and Heinemann, U. (eds), Topics in Molecular and Structural Biology, Protein-Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (LacI repressor protein changes conformation when contacted with lactose, thereby preventing the Lad repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to a simian virus 40 (SV40) early promoter, a mouse mammary tumor virus (MMTV) or human immunodeficiency virus (HIV) long terminal repeat (LTR) promoter, a MoMuLV promoter, an avian leukemia virus promoter, an Epstein-Barr virus immediate early promoter, a Rous sarcoma virus promoter, the EF-1 alpha promoter, as well as human gene promoters such as, but not limited to, an actin promoter, a myosin promoter, a hemoglobin promoter, and a creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

In some embodiments, a nucleic acid of the present disclosure further comprises a nucleic acid sequence encoding a TCR and/or CAR inducible expression cassette. In one embodiment, the TCR and/or CAR inducible expression cassette is for the production of a transgenic polypeptide product that is released upon TCR and/or CAR signaling. See, e.g., Chmielewski and Abken, Expert Opin. Biol. Ther. (2015) 15(8): 1145-1154; and Abken, Immunotherapy (2015) 7(5): 535-544. In some embodiments, a nucleic acid of the present disclosure further comprises a nucleic acid sequence encoding a cytokine operably linked to a T-cell activation responsive promoter. In some embodiments, the cytokine operably linked to a T-cell activation responsive promoter is present on a separate nucleic acid sequence. In one embodiment, the cytokine is IL-12.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35: 2543-2549; Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648; Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617); SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, an expression vector (e.g., a lentiviral vector) may be used to introduce the chimeric cell surface sialidase or variant sialidase precursor protein into an immune cell or precursor thereof (e.g., a T cell). Accordingly, an expression vector (e.g., a lentiviral vector) of the present invention may comprise a nucleic acid encoding for a chimeric cell surface sialidase or variant sialidase precursor protein (and optionally a TCR and/or CAR). In some embodiments, the expression vector (e.g., lentiviral vector) will comprise additional elements that will aid in the functional expression of the chimeric cell surface sialidase or variant sialidase precursor protein encoded therein. In some embodiments, an expression vector comprising a nucleic acid encoding for a chimeric cell surface sialidase or variant sialidase precursor protein further comprises a mammalian promoter. In one embodiment, the vector further comprises an elongation-factor-1-alpha promoter (EF-1α promoter). Use of an EF-1α promoter may increase the efficiency in expression of downstream transgenes (e.g., a chimeric cell surface sialidase or variant sialidase precursor protein or TCR or CAR encoding nucleic acid sequence). Physiologic promoters (e.g., an EF-1α promoter) may be less likely to induce integration mediated genotoxicity, and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention.

In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In one embodiment, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a chimeric cell surface sialidase or variant sialidase precursor protein.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a chimeric cell surface sialidase or variant sialidase precursor protein and/or TCR and/or CAR of the present disclosure. Methods for introducing RNA into a host cell are known in the art. See, e.g., Zhao et al. Cancer Res. (2010) 15: 9053. Introducing RNA comprising a nucleotide sequence encoding a chimeric cell surface sialidase or variant sialidase precursor protein and/or TCR and/or CAR of the present disclosure into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a chimeric cell surface sialidase or variant sialidase precursor protein and/or TCR and/or CAR of the present disclosure.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

H. Methods of Treatment

The modified cells (e.g., T cells comprising a chimeric cell surface sialidase or a variant sialidase precursor protein) described herein may be included in a composition for immunotherapy. The composition may include a pharmaceutical composition and further include a pharmaceutically acceptable carrier. A therapeutically effective amount of the pharmaceutical composition comprising the modified T cells may be administered.

In one aspect, the invention includes a method for adoptive cell transfer therapy comprising administering to a subject in need thereof a modified T cell of the present invention. In another aspect, the invention includes a method of treating a disease or condition (e.g. cancer) in a subject comprising administering to a subject in need thereof a population of modified T cells.

Methods for administration of immune cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338. In some embodiments, the cell therapy, e.g., adoptive T cell therapy is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject has been treated with a therapeutic agent targeting the disease or condition, e.g. the tumor, prior to administration of the cells or composition containing the cells. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse. In some aspects, the subject has not received prior treatment with another therapeutic agent.

In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

The modified immune cells of the present invention can be administered to an animal, preferably a mammal, even more preferably a human, to treat a cancer. In addition, the cells of the present invention can be used for the treatment of any condition related to a cancer, especially a cell-mediated immune response against a tumor cell(s), where it is desirable to treat or alleviate the disease. The types of cancers to be treated with the modified cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. Other exemplary cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. The cancers may be non-solid tumors (such as hematological tumors) or solid tumors. Adult tumors/cancers and pediatric tumors/cancers are also included. In one embodiment, the cancer is a solid tumor or a hematological tumor. In one embodiment, the cancer is a carcinoma. In one embodiment, the cancer is a sarcoma. In one embodiment, the cancer is a leukemia. In one embodiment the cancer is a solid tumor.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

In certain exemplary embodiments, the modified immune cells of the invention are used to treat a myeloma, or a condition related to myeloma. Examples of myeloma or conditions related thereto include, without limitation, light chain myeloma, non-secretory myeloma, monoclonal gammopathy of undertermined significance (MGUS), plasmacytoma (e.g., solitary, multiple solitary, extramedullary plasmacytoma), amyloidosis, and multiple myeloma. In one embodiment, a method of the present disclosure is used to treat multiple myeloma. In one embodiment, a method of the present disclosure is used to treat refractory myeloma. In one embodiment, a method of the present disclosure is used to treat relapsed myeloma.

In certain exemplary embodiments, the modified immune cells of the invention are used to treat a melanoma, or a condition related to melanoma. Examples of melanoma or conditions related thereto include, without limitation, superficial spreading melanoma, nodular melanoma, lentigo maligna melanoma, acral lentiginous melanoma, amelanotic melanoma, or melanoma of the skin (e.g., cutaneous, eye, vulva, vagina, rectum melanoma). In one embodiment, a method of the present disclosure is used to treat cutaneous melanoma. In one embodiment, a method of the present disclosure is used to treat refractory melanoma. In one embodiment, a method of the present disclosure is used to treat relapsed melanoma.

In yet other exemplary embodiments, the modified immune cells of the invention are used to treat a sarcoma, or a condition related to sarcoma. Examples of sarcoma or conditions related thereto include, without limitation, angiosarcoma, chondrosarcoma, Ewing's sarcoma, fibrosarcoma, gastrointestinal stromal tumor, leiomyosarcoma, liposarcoma, malignant peripheral nerve sheath tumor, osteosarcoma, pleomorphic sarcoma, rhabdomyosarcoma, and synovial sarcoma. In one embodiment, a method of the present disclosure is used to treat liposarcoma such as myxoid/round cell liposarcoma, differentiated/dedifferentiated liposarcoma, and pleomorphic liposarcoma. In one embodiment, a method of the present disclosure is used to treat myxoid/round cell liposarcoma. In one embodiment, a method of the present disclosure is used to treat a refractory sarcoma. In one embodiment, a method of the present disclosure is used to treat a relapsed sarcoma.

The cells of the invention to be administered may be autologous, with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, alymph node, an organ, a tumor, and the like.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as CD8$^+$ and CD4$^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as CD4$^+$ to CD8$^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or subtype, or minimum number of cells of the population or sub-type per unit of body weight. Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of CD4$^+$ to CD8$^+$ cells, and/or is based on a desired fixed or minimum dose of CD4$^+$ and/or CD8$^+$ cells.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $1\times10^5$ cells/kg to about $1\times10^{11}$ cells/kg $10^4$ and at or about $10^{11}$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight. For example, in some embodiments, the cells are administered at, or within a certain range of error of, between at or about $10^4$ and at or about $10^9$ T cells/kilograms (kg) body weight, such as between 10' and $10^6$ T cells/kg body weight, for example, at or about $1\times10^5$ T cells/kg, $1.5\times10^1$ T cells/kg, $2\times10^1$ T cells/kg, or $1\times10^6$ T cells/kg body weight. In other exemplary embodiments, a suitable dosage range of modified cells for use in a method of the present disclosure includes, without limitation, from about $1\times10^5$ cells/kg to about $1\times10^6$ cells/kg, from about $1\times10^6$ cells/kg to about $1\times10^7$ cells/kg, from about $1\times10^7$ cells/kg about $1\times10^8$ cells/kg, from about $1\times10^8$ cells/kg about $1\times10^9$ cells/kg, from about $1\times10^9$ cells/kg about $1\times10^{10}$ cells/kg, from about $1\times10^{10}$ cells/kg about $1\times10^{11}$ cells/kg. In an exemplary embodiment, a suitable dosage for use in a method of the present disclosure is about $1\times10^8$ cells/kg. In an exemplary embodiment, a suitable dosage for use in a method of the present disclosure is about $1\times10^7$ cells/kg. In other embodiments, a suitable dosage is from about $1\times10^7$ total cells to about $5\times10^7$ total cells. In some embodiments, a suitable dosage is from about $1\times10^8$ total cells to about $5\times10^8$ total cells. In some embodiments, a suitable dosage is from about $1.4\times10^7$ total cells to about $1.1\times10^9$ total cells. In an exemplary embodiment, a suitable dosage for use in a method of the present disclosure is about $7\times10^9$ total cells.

In some embodiments, the cells are administered at or within a certain range of error of between at or about $10^4$ and at or about $10^9$ CD4$^+$ and/or CD8$^+$ cells/kilograms (kg) body weight, such as between $10^1$ and $10^6$ CD4$^+$ and/or CD8$^+$ cells/kg body weight, for example, at or about $1\times10^5$ CD4$^+$ and/or CD8$^+$ cells/kg, $1.5\times10^5$ CD4$^+$ and/or CD8$^+$ cells/kg, $2\times10^5$ CD4$^+$ and/or CD8$^+$ cells/kg, or $1\times10^6$ CD4$^+$ and/or CD8$^+$ cells/kg body weight. In some embodiments, the cells are administered at or within a certain range of error of, greater than, and/or at least about $1\times10^6$, about $2.5\times10^6$, about $5\times10^6$, about $7.5\times10^6$, or about $9\times10^6$ CD4$^+$ cells, and/or at least about $1\times10^6$, about $2.5\times10^6$, about $5\times10^6$, about $7.5\times10^6$, or about $9\times10^6$ CD8$^+$ cells, and/or at least about $1\times10^6$, about $2.5\times10^6$, about $5\times10^6$, about $7.5\times10^6$, or about $9\times10^6$ T cells. In some embodiments, the cells are administered at or within a certain range of error of between about $10^8$ and $10^{12}$ or between about $10^{10}$ and $10^{11}$ T cells, between about $10^8$ and $10^{12}$ or between about $10^{10}$ and $10^{11}$ CD4$^+$ cells, and/or between about $10^8$ and $10^{12}$ or between about $10^{10}$ and $10^{11}$ CD8$^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios, for example, in some embodiments, the desired ratio (e.g., ratio of CD4$^+$ to CD8$^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, a dose of modified cells is administered to a subject in need thereof, in a single dose or multiple doses. In some embodiments, a dose of modified cells is administered in multiple doses, e.g., once a week or every 7 days, once every 2 weeks or every 14 days, once every 3 weeks or every 21 days, once every 4 weeks or every 28 days. In an exemplary embodiment, a single dose of modified cells is administered to a subject in need thereof. In an exemplary embodiment, a single dose of modified cells is administered to a subject in need thereof by rapid intravenous infusion.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

In certain embodiments, the modified cells of the invention may be administered to a subject in combination with an immune checkpoint antibody (e.g., an anti-PD1, anti-CTLA-4, or anti-PDL1 antibody). For example, the modified cell may be administered in combination with an antibody or antibody fragment targeting, for example, PD-1 (programmed death 1 protein). Examples of anti-PD-1 antibodies include, but are not limited to, pembrolizumab (KEYTRUDA®, formerly lambrolizumab, also known as MK-3475), and nivolumab (BMS-936558, MDX-1106, ONO-4538, OPDIVA®) or an antigen-binding fragment thereof. In certain embodiments, the modified cell may be administered in combination with an anti-PD-L1 antibody or antigen-binding fragment thereof. Examples of anti-PD-L1 antibodies include, but are not limited to, BMS-936559, MPDL3280A (TECENTRIQ®, Atezolizumab), and MEDI4736 (Durvalumab, Imfinzi). In certain embodiments, the modified cell may be administered in combination with an anti-CTLA-4 antibody or antigen-binding fragment thereof. An example of an anti-CTLA-4 antibody includes, but is not limited to, Ipilimumab (trade name Yervoy). Other types of immune checkpoint modulators may also be used including, but not limited to, small molecules, siRNA, miRNA, and CRISPR systems. Immune checkpoint modulators may be administered before, after, or concurrently with the modified cell comprising the CAR. In certain embodiments, combination treatment comprising an immune checkpoint modulator may increase the therapeutic efficacy of a therapy comprising a modified cell of the present invention.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD107a, IFNγ, IL-2, and TNF. In some aspects the biological activity is measured by assessing clinical outcome, such as reduction in tumor burden or load.

In certain embodiments, the subject is provided a secondary treatment. Secondary treatments include but are not limited to chemotherapy, radiation, surgery, and medications.

In some embodiments, the subject can be administered a conditioning therapy prior to CAR T cell therapy. In some embodiments, the conditioning therapy comprises administering an effective amount of cyclophosphamide to the subject. In some embodiments, the conditioning therapy comprises administering an effective amount of fludarabine to the subject. In preferred embodiments, the conditioning therapy comprises administering an effective amount of a combination of cyclophosphamide and fludarabine to the subject. Administration of a conditioning therapy prior to CAR T cell therapy may increase the efficacy of the CAR T cell therapy. Methods of conditioning patients for T cell therapy are described in U.S. Pat. No. 9,855,298, which is incorporated herein by reference in its entirety.

In some embodiments, a specific dosage regimen of the present disclosure includes a lymphodepletion step prior to the administration of the modified T cells. In an exemplary embodiment, the lymphodepletion step includes administration of cyclophosphamide and/or fludarabine.

In some embodiments, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day). In an exemplary embodiment, the dose of cyclophosphamide is about 300 mg/m$^2$/day. In some embodiments, the lymphodepletion step includes administration of fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the dose of fludarabine is about 30 mg/m$^2$/day.

In some embodiment, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the lymphodepletion step includes administration of cyclophosphamide at a dose of about 300 mg/m$^2$/day, and fludarabine at a dose of about 30 mg/m$^2$/day.

In an exemplary embodiment, the dosing of cyclophosphamide is 300 mg/m$^2$/day over three days, and the dosing of fludarabine is 30 mg/m$^2$/day over three days.

Dosing of lymphodepletion chemotherapy may be scheduled on Days −6 to −4 (with a −1 day window, i.e., dosing on Days −7 to −5) relative to T cell (e.g., CAR-T, TCR-T, a modified T cell, etc.) infusion on Day 0.

In an exemplary embodiment, for a subject having cancer, the subject receives lymphodepleting chemotherapy including 300 mg/m$^2$ of cyclophosphamide by intravenous infusion 3 days prior to administration of the modified T cells. In an exemplary embodiment, for a subject having cancer, the subject receives lymphodepleting chemotherapy including 300 mg/m$^2$ of cyclophosphamide by intravenous infusion for 3 days prior to administration of the modified T cells.

In an exemplary embodiment, for a subject having cancer, the subject receives lymphodepleting chemotherapy including fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including fludarabine at a dose of 30 mg/m$^2$ for 3 days.

In an exemplary embodiment, for a subject having cancer, the subject receives lymphodepleting chemotherapy including cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including cyclophosphamide at a dose of about 300 mg/m$^2$/day, and fludarabine at a dose of 30 mg/m$^2$ for 3 days.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It is known in the art that one of the adverse effects following infusion of CAR T cells is the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS; grade≥3 organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with the CRS syndrome. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, the invention provides for, following the diagnosis of CRS, appropriate CRS management strategies to mitigate the physiological symptoms of uncontrolled inflammation without dampening the antitumor efficacy of the engineered cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief. More severe cases include patients with any degree of hemodynamic instability; with any hemodynamic instability, the administration of tocilizumab is recommended. The first-line management of CRS may be tocilizumab, in some embodiments, at the labeled dose of 8 mg/kg IV over 60 minutes (not to exceed 800 mg/dose); tocilizumab can be repeated Q8 hours. If suboptimal response to the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) *Biol Blood Marrow Transplant*, doi.org/10.1016/j.bbmt.2018.12.758; Neelapu et al. (2018) *Nat Rev Clin Oncology*, 15:47; Teachey et al. (2016) *Cancer Discov*, 6(6):664-679).

Features consistent with Macrophage Activation Syndrome (MAS) or Hemophagocytic lymphohistiocytosis (HLH) have been observed in patients treated with CAR-T therapy (Henter, 2007), coincident with clinical manifestations of the CRS. MAS appears to be a reaction to immune activation that occurs from the CRS, and should therefore be considered a manifestation of CRS. MAS is similar to HLH (also a reaction to immune stimulation). The clinical syndrome of MAS is characterized by high grade non-remitting fever, cytopenias affecting at least two of three lineages, and hepatosplenomegaly. It is associated with high serum ferritin, soluble interleukin-2 receptor, and triglycerides, and a decrease of circulating natural killer (NK) activity.

In one aspect, the invention includes a method of treating cancer in a subject in need thereof, comprising administering to the subject any one of the modified immune or precursor cells disclosed herein.

In another aspect, the invention includes a method of treating cancer in a subject in need thereof, the method comprising administering a modified T cell comprising a chimeric cell surface sialidase (neuraminidase) enzyme comprising an extracellular portion comprising a sialidase (neuraminidase) or an enzymatically functional portion thereof, and a heterologous transmembrane domain capable of tethering the extracellular portion to a cell surface, and a chimeric antigen receptor (CAR).

In another aspect, the invention includes a method of treating cancer in a subject in need thereof, the method comprising administering a modified T cell comprising a variant sialidase precursor protein comprising a heterologous secretory sequence operably linked to a sialidase (neuraminidase) or an enzymatically functional portion thereof, wherein the variant sialidase precursor protein lacks a transmembrane domain, and wherein the sialidase or enzymatically functional portion thereof is capable of being secreted from an immune or precursor cell thereof when the variant sialidase precursor protein is expressed in the cell, and a chimeric antigen receptor (CAR).

In certain embodiments, the CAR comprises specificity for TnMUC1. In certain embodiments, the CAR comprises specificity for CD19. In certain embodiments, the CAR comprises specificity for PSMA.

In certain embodiments, the method further comprises administering to the subject a population of innate immune cells. In certain embodiments, the innate immune cells are NK cells. In certain embodiments, the NK cells are autologous NK cells obtained from a human subject.

In another aspect, the invention includes a method of treating cancer in a subject in need thereof comprising: administering to the subject a therapeutically effective amount of a modified T cell comprising a chimeric cell surface sialidase (neuraminidase) enzyme comprising an extracellular portion comprising a sialidase (neuraminidase) or an enzymatically functional portion thereof, and a heterologous transmembrane domain capable of tethering the extracellular portion to a cell surface, and a chimeric antigen receptor (CAR); and administering to the subject a therapeutically effective amount of a NK cell.

In another aspect, the invention includes a method of treating cancer in a subject in need thereof comprising: administering to the subject a therapeutically effective amount of a modified T cell comprising a variant sialidase precursor protein comprising a heterologous secretory sequence operably linked to a sialidase (neuraminidase) or an enzymatically functional portion thereof, wherein the variant sialidase precursor protein lacks a transmembrane domain, and wherein the sialidase or enzymatically functional portion thereof is capable of being secreted from an immune or precursor cell thereof when the variant sialidase precursor protein is expressed in the cell, and a chimeric antigen receptor (CAR); and administering to the subject a therapeutically effective amount of a NK cell.

In certain embodiments, the modified T cell and the NK cell are administered simultaneously. In certain embodiments, the modified T cell and the NK cell are administered separately. In certain embodiments, the NK cell is autologous.

I. Sources of Immune Cells

Prior to expansion, a source of immune cells may be obtained from a subject for ex vivo manipulation. Sources of target cells for ex vivo manipulation may also include, e.g., autologous or heterologous donor blood, cord blood, or bone marrow. For example, the source of immune cells may be from the subject to be treated with the modified immune cells of the invention, e.g., the subject's blood, the subject's cord blood, or the subject's bone marrow. Non-limiting examples of subjects include humans, dogs, cats, mice, rats, and transgenic species thereof. Preferably, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some aspects, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), a stem cell memory T cell, a lymphoid progenitor cell a hematopoietic stem cell, a natural killer cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

In some embodiments, the methods include isolating immune cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some aspects, a washing step is accomplished by tangential flow filtration (TFF) according to the manufacturer's instructions. In some embodiments, the cells are resuspended in a variety of biocompatible buffers after washing. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient.

In one embodiment, immune are obtained cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker+) or express high levels (marker$^{high}$) of one or more particular markers, such as surface markers, or that are negative for (marker−) or express relatively low levels (marker$^{low}$) of one or more markers. For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD 127, and/or CD62L and/or depleted of (e.g., negatively selected for) cells that are positive for or express high surface levels of CD45RA. In some embodiments, cells are enriched for or depleted of cells positive or expressing high surface levels of CD 122, CD95, CD25, CD27, and/or IL7-Ra (CD 127). In some examples, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNABEADS® M-450 CD3/CD28 T Cell Expander).

In some embodiments, T cells are separated from a PBMC sample by negative selection of markers expressed on non-T cells, such as B cells, monocytes, or other white blood cells, such as CD 14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such sub-populations. In some embodiments, combining TCM-enriched CD8+ T cells and CD4+ T cells further enhances efficacy.

In some embodiments, memory T cells are present in both CD62L+ and CD62L-subsets of CD8+ peripheral blood lymphocytes. PBMC can be enriched for or depleted of CD62L-CD8+ and/or CD62L+CD8+ fractions, such as using anti-CD8 and anti-CD62L antibodies. In some embodiments, a CD4+ T cell population and a CD8+ T cell sub-population, e.g., a sub-population enriched for central memory (TCM) cells. In some embodiments, the enrichment for central memory T (TCM) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for TCM cells is carried out by depletion of cells expressing CD4, CD 14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD 14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+T helper cells are sorted into naive, central memory, and effector cells by identifying cell populations that have cell surface antigens. CD4+ lymphocytes can be obtained by standard methods. In some embodiments, naive CD4+T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L- and CD45RO. In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/ mL.

In another embodiment, T cells are isolated from peripheral blood by lysing the red blood cells and depleting the monocytes, for example, by centrifugation through a PER-COLL™ gradient. Alternatively, T cells can be isolated from an umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

J. Expansion of Immune Cells

Whether prior to or after modification of cells to express a a chimeric cell surface sialidase or a variant sialidase precursor protein and/or a TCR and/or CAR, the cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005. For example, the T cells of the invention may be expanded by contact with a surface having attached thereto an agent that stimulates a CD3/TCR complex associated signal and a ligand that stimulates a co-stimulatory molecule on the surface of the T cells. In particular, T cell populations may be stimulated by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, T cells can be contacted with an anti-CD3 antibody and an anti-CD28 antibody, under conditions appropriate for stimulating proliferation of the T cells. Examples of an anti-CD28 antibody include 9.3, B-T3, XR-CD28 (Diaclone, Besancon, France) and these can be used in the invention, as can other methods and reagents known in the art (see, e.g., ten Berge et al., Transplant Proc. (1998) 30(8): 3975-3977; Haanen et al., J. Exp. Med. (1999) 190(9): 1319-1328; and Garland et al., J. Immunol. Methods (1999) 227(1-2): 53-63).

Expanding T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), inter-leukin-2 (IL-2), insulin, IFN-gamma, IL-4, IL-7, GM-CSF, IL-10, IL-12, IL-15, TGF-beta, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. A cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more. In one embodiment, human T regulatory cells are expanded via anti-CD3 antibody coated KT64.86 artificial antigen presenting cells (aAPCs). Methods for expanding and activating T cells can be found in U.S. Pat. Nos. 7,754,482, 8,722,400, and 9,555,105, contents of which are incorporated herein in their entirety.

In one embodiment, the method of expanding the T cells can further comprise isolating the expanded T cells for further applications. In another embodiment, the method of expanding can further comprise a subsequent electropora-tion of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

K. Pharmaceutical Compositions and Formulations

Also provided are populations of modified immune cells of the invention, compositions containing such cells and/or enriched for such cells, such as in which cells expressing the chimeric cell surface sialidase or variant sialidase precursor protein make up at least 50%, 60%, 70%, 80%, 90%, 91%, 92%, 93%, 94%, 95%, 96%, 97%, 98%, 99%, or more of the total cells in the composition or cells of a certain type such as T cells or CD8$^+$ or CD4$^+$ cells. Among the compositions are pharmaceutical compositions and formulations for administration, such as for adoptive cell therapy. Also provided are therapeutic methods for administering the cells and compositions to subjects, e.g., patients.

Also provided are compositions including the cells for administration, including pharmaceutical compositions and formulations, such as unit dose form compositions including the number of cells for administration in a given dose or fraction thereof. The pharmaceutical compositions and for-mulations generally include one or more optional pharma-ceutically acceptable carrier or excipient. In some embodi-ments, the composition includes at least one additional therapeutic agent.

The term "pharmaceutical formulation" refers to a prepa-ration which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceu-tical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives. Suitable preserva-tives may include, for example, methylparaben, propylpa-raben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concen-trations employed, and include, but are not limited to: buffers such as phosphate, citrate, and other organic acids; antioxidants including ascorbic acid and methionine; pre-servatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobu-lins; hydrophilic polymers such as polyvinylpyrrolidone; amino acids such as glycine, glutamine, asparagine, histi-dine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming coun-ter-ions such as sodium; metal complexes (e.g. Zn-protein complexes); and/or non-ionic surfactants such as polyeth-ylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

L. Methods of Producing Genetically Modified Immune Cells

The present disclosure provides methods for producing or generating a modified immune cell or precursor thereof (e.g., a T cell comprising a chimeric cell surface sialidase or a variant sialidase precursor protein) of the invention for tumor immunotherapy, e.g., adoptive immunotherapy.

In some embodiments, the chimeric cell surface sialidase or variant sialidase precursor protein is introduced into a cell by an expression vector. Expression vectors comprising a nucleic acid sequence encoding a chimeric cell surface sialidase or a variant sialidase precursor protein of the present invention are provided herein. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggybak, and Integrases such as Phi31. Some other suitable expression vectors include Herpes simplex virus (HSV) and retrovirus expression vectors.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the chimeric cell surface sialidase or a variant sialidase precursor protein in the host cell. In some embodiments, the adenovirus genome is a 36 kb, linear, double stranded DNA, where a foreign DNA sequence (e.g., a nucleic acid encoding a chimeric cell surface sialidase or a variant sialidase precursor protein) may be inserted to substitute large pieces of adenoviral DNA in order to make the expression vector of the present invention (see, e.g., Danthinne and Imperiale, Gene Therapy (2000) 7(20): 1707-1714). Another expression vector is based on an adeno associated virus (AAV), which takes advantage of the adenovirus coupled systems. This AAV expression vector has a high frequency of integration into the host genome. It can infect nondividing cells, thus making it useful for delivery of genes into mammalian cells, for example, in tissue cultures or in vivo. The AAV vector has a broad host range for infectivity. Details concerning the generation and use of AAV vectors are described in U.S. Pat. Nos. 5,139,941 and 4,797,368. In some embodiments, the nucleic acid encoding a chimeric cell surface sialidase or a variant sialidase precursor protein is introduced into the cell via viral transduction. In certain embodiments, the viral transduction comprises contacting the immune or precursor cell with a viral vector comprising the nucleic acid encoding a chimeric cell surface sialidase or a variant sialidase precursor protein. In certain embodiments, the viral vector is an adeno-associated viral (AAV) vector. In certain embodiments, the AAV vector comprises a Woodchuck Hepatitis Virus post-transcriptional regulatory element (WPRE). In certain embodiments, the AAV vector comprises a polyadenylation (polyA) sequence. In certain embodiments, the polyA sequence is a bovine growth hormone (BGH) polyA sequence.

Retrovirus expression vectors are capable of integrating into the host genome, delivering a large amount of foreign genetic material, infecting a broad spectrum of species and cell types and being packaged in special cell lines. The retroviral vector is constructed by inserting a nucleic acid (e.g., a nucleic acid encoding a chimeric cell surface sialidase or a variant sialidase precursor protein) into the viral genome at certain locations to produce a virus that is replication defective. Though the retroviral vectors are able to infect a broad variety of cell types, integration and stable expression of the chimeric cell surface sialidase or variant sialidase precursor protein requires the division of host cells.

Lentiviral vectors are derived from lentiviruses, which are complex retroviruses that, in addition to the common retroviral genes gag, pol, and env, contain other genes with regulatory or structural function (see, e.g., U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentiviral vectors have been generated by multiply attenuating the HIV virulence genes, for example, the genes env, vif, vpr, vpu and nef are deleted making the vector biologically safe. Lentiviral vectors are capable of infecting non-dividing cells and can be used for both in vivo and ex vivo gene transfer and expression, e.g., of a nucleic acid encoding a chimeric cell surface sialidase or a variant sialidase precursor protein (see, e.g., U.S. Pat. No. 5,994,136).

Expression vectors including a nucleic acid of the present disclosure can be introduced into a host cell by any means known to persons skilled in the art. The expression vectors may include viral sequences for transfection, if desired. Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and may be screened by virtue of a marker present in the vectors. Various markers that may be used are known in the art, and may include hprt, neomycin resistance, thymidine kinase, hygromycin resistance, etc. As used herein, the terms "cell," "cell line," and "cell culture" may be used interchangeably. In some embodiments, the host cell an immune cell or precursor thereof, e.g., a T cell, an NK cell, or an NKT cell.

The present invention also provides modified cells which include and stably express a chimeric cell surface sialidase or a variant sialidase precursor protein of the present disclosure. In some embodiments, the modified cells are genetically engineered T-lymphocytes (T cells), naive T cells (TN), memory T cells (for example, central memory T cells (TCM), effector memory cells (TEM)), natural killer cells (NK cells), and macrophages capable of giving rise to therapeutically relevant progeny. In certain embodiments, the genetically engineered cells are autologous cells.

Modified cells (e.g., comprising a chimeric cell surface sialidase or a variant sialidase precursor protein) may be produced by stably transfecting host cells with an expression vector including a nucleic acid of the present disclosure. Additional methods for generating a modified cell of the present disclosure include, without limitation, chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells expressing a chimeric cell surface sialidase or a variant sialidase precursor protein of the present disclosure may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, e.g., Sambrook et al. (2001), Molecular Cloning: A Laboratory Manual, Cold Spring Harbor Laboratory, New York. Chemical methods for introducing an expression vector into a host cell include colloidal dispersion systems, such as macromolecule complexes, nanocapsules, microspheres, beads, and lipid-based systems including oil-in-water emulsions, micelles, mixed micelles, and liposomes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform may be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). Compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, molecular biology assays well known to those of skill in the art, such as Southern and Northern blotting, RT-PCR and PCR; biochemistry assays, such as detecting the presence or absence of a particular peptide, e.g., by immunological means (ELISAs and Western blots) or by assays described herein to identify agents falling within the scope of the invention.

In one embodiment, the nucleic acids introduced into the host cell are RNA. In another embodiment, the RNA is mRNA that comprises in vitro transcribed RNA or synthetic RNA. The RNA may be produced by in vitro transcription using a polymerase chain reaction (PCR)-generated template. DNA of interest from any source can be directly converted by PCR into a template for in vitro mRNA synthesis using appropriate primers and RNA polymerase. The source of the DNA may be, for example, genomic DNA, plasmid DNA, phage DNA, cDNA, synthetic DNA sequence or any other appropriate source of DNA.

PCR may be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers may also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA. 5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

In some embodiments, the RNA is electroporated into the cells, such as in vitro transcribed RNA. Any solutes suitable for cell electroporation, which can contain factors facilitating cellular permeability and viability such as sugars, peptides, lipids, proteins, antioxidants, and surfactants can be included.

In some embodiments, a nucleic acid encoding a chimeric cell surface sialidase or a variant sialidase precursor protein of the present disclosure will be RNA, e.g., in vitro synthesized RNA. Methods for in vitro synthesis of RNA are known in the art; any known method can be used to synthesize RNA comprising a sequence encoding a chimeric cell surface sialidase or a variant sialidase precursor protein. Methods for introducing RNA into a host cell are known in the art. See, e.g., Zhao et al. Cancer Res. (2010) 15: 9053. Introducing RNA comprising a nucleotide sequence encoding a chimeric cell surface sialidase or a variant sialidase precursor protein into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a chimeric cell surface sialidase or a variant sialidase precursor protein.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced.

Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

In some embodiments, the immune cells (e.g. T cells) can be incubated or cultivated prior to, during and/or subsequent to introducing the nucleic acid molecule encoding the chimeric cell surface sialidase or a variant sialidase precursor protein (and/or the TCR and/or CAR). In some embodiments, the cells (e.g. T cells) can be incubated or cultivated prior to, during or subsequent to the introduction of the nucleic acid molecule encoding the chimeric cell surface sialidase or a variant sialidase precursor protein, such as prior to, during or subsequent to the transduction of the cells with a viral vector (e.g. lentiviral vector) encoding the exogenous receptor.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Molecular Cloning: Codon optimized nucleic acid sequences of human Neu1, Neu2, Neu3, and Neu4 were synthesized as "gBlock Gene Fragments" through Integrated DNA Technologies (IDT). Each neuraminidase was subcloned into the pCR-BluntII-TOPO vector, then cloned into destination pTRPE lentiviral vectors, which are third-generation lentiviral production vectors utilizing the EF1α promoter, and containing the CD8a leader sequence, hinge, transmembrane domain, and 4-1BB and CD3z endodomains. Myc-Tag sequences were also cloned into each construct, and other receptor versions were designed to include a truncated intracellular domain ($\Delta z$ endodomain).

Transduction and Expansion of Normal Donor T Cells: HEK 293T cells were transfected with pTRPE-Neu2-BBz, pTRPE-Myc-Neu2-BBz, pTRPE-5E5-CD2z, pELPS-CD19-BBz, and pTRPE-PSMA-BBz in addition to gag/pol, env, and Vsvg packaging mix. Virus was collected and concentrated at 24 and 48 hrs. Normal donor T cells were obtained from the Human Immunology Core (HIC) at the University of Pennsylvania where they were negatively selected from apheresis. The normal donor T cells were activated in-vitro with CD3/CD28 magnetic Dynabeads (Thermo Fischer Scientific), transduced with lentivirus 16 hrs after bead activation, and cultured in RPMI 1640 medium (Gibco) supplemented with 10% FBS, 1% penicillin-streptomycin (Gibco), 1% HEPES (Gibco), and 1% GlutaMax (Gibco) (R10 complete growth medium), with the addition of 30 U/mL of IL-2 for 10-17 days.

Cell Culture: The adherent PC3 and DU145 prostate cancer cells lines were obtained from ATCC and maintained with R10 complete growth medium. The human embryonic kidney 293T cell line was also obtained from ATCC and maintained on R10. All T cells used in assays were obtained from the Human Immunology Core at the University of Pennsylvania and activated and transduced in R10, expanded in R10 supplemented with IL-2, and maintained in R10 during use in assays.

Flow Cytometry: Before each staining, cells were washed in either phosphate-buffered saline (PBS), or PBS containing 2% FBS, and stains were performed on ice. SNA expression was assessed in neuraminidase activity assays by staining PC3 and DU145 cells with Biotinylated-SNA Lectin (Vector Laboratories) followed by PE-conjugated streptavidin. Surface Myc-Tag expression was assessed by staining 293T cells with Myc-Tag (71D10) rabbit mAb-Alexa AF700 conjugated (Cell Signaling Technology). Extracellular Neu2 expression was assessed by staining 293T cells with Neu2 rabbit pAb (OriGene) and goat anti-rabbit AF488 secondary antibody. Intracellular CD3z was detected by fixing and permeabilizing the 293T cells (BD Cytofix/Cytoperm), then staining for CD3z/CD247 rabbit pAb (Proteintech), and goat anti rabbit AF488 secondary antibody. Viability of cells used in assays was assessed using Live/Dead Violet Stain (Thermo Fischer Scientific). CAR T cells were detected by staining with biotinylated goat anti mouse F(ab)$_2$ antibody (Jackson ImmunoResearch) and PE-conjugated streptavidin. Flow analysis was performed by gating singlets on FSC-H versus FSC-A and SSC-H versus SSC-A, then on forward versus side scatter characteristics. All flow cytometry was performed on LSRFortessa or LSRII multi-laser Becton Dickinson cytometers.

Figure 7:
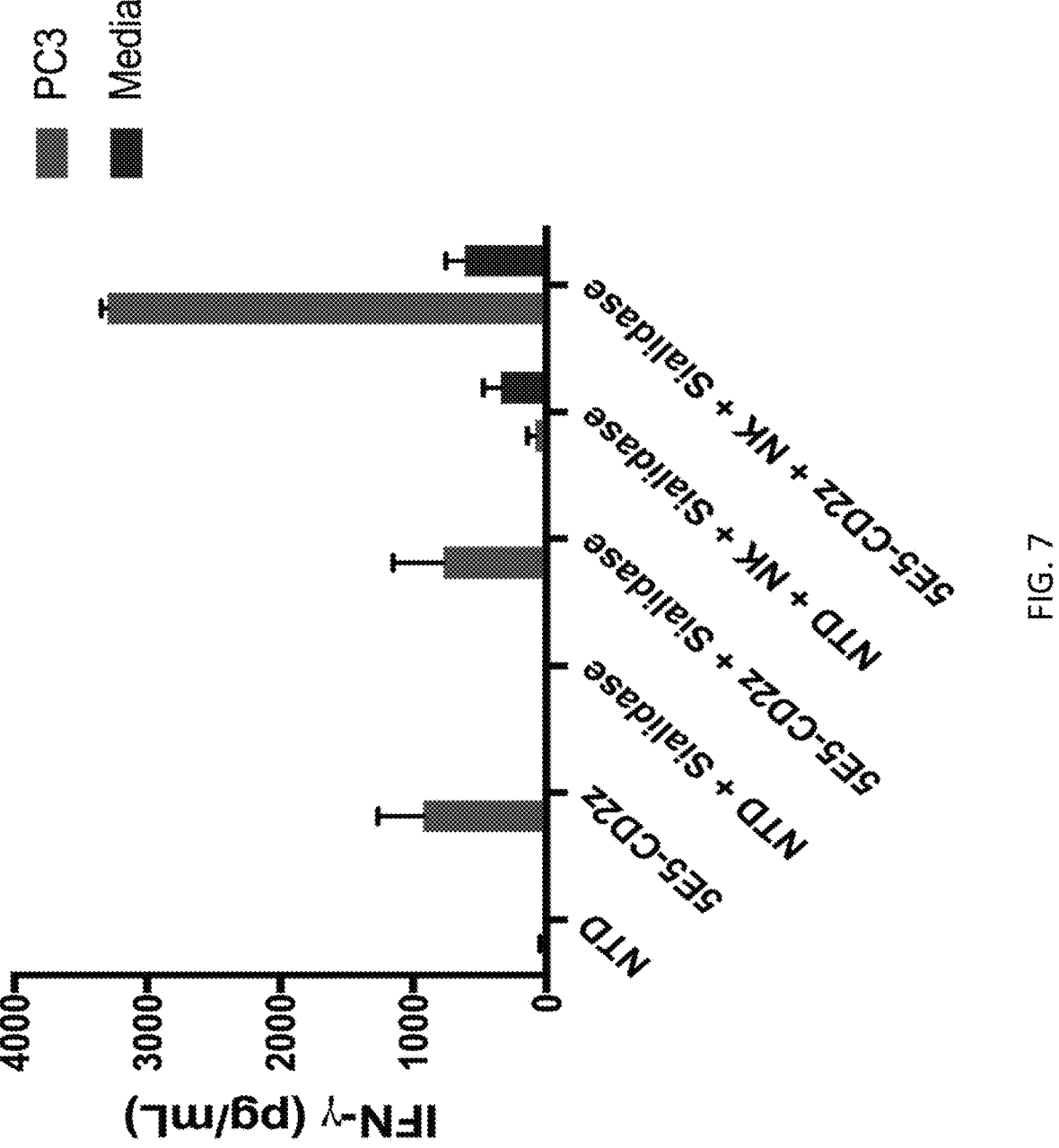
FIG. 7 depicts the finding that addition of sialidase and NK cells enhances IFN-g production of CART cells targeting prostate cancer PC3 cells. 5E5-CD2z CART cells demonstrate reactivity to PC3 prostate cancer cells in co-culture alone. Interestingly, IFN-g secretion is elevated when both sialidase and NK cells are also added at the time of co-culture with 5E5-CD2z CART cells. This combination approach shows greater reactivity than with each effector condition alone.
Figure 9:
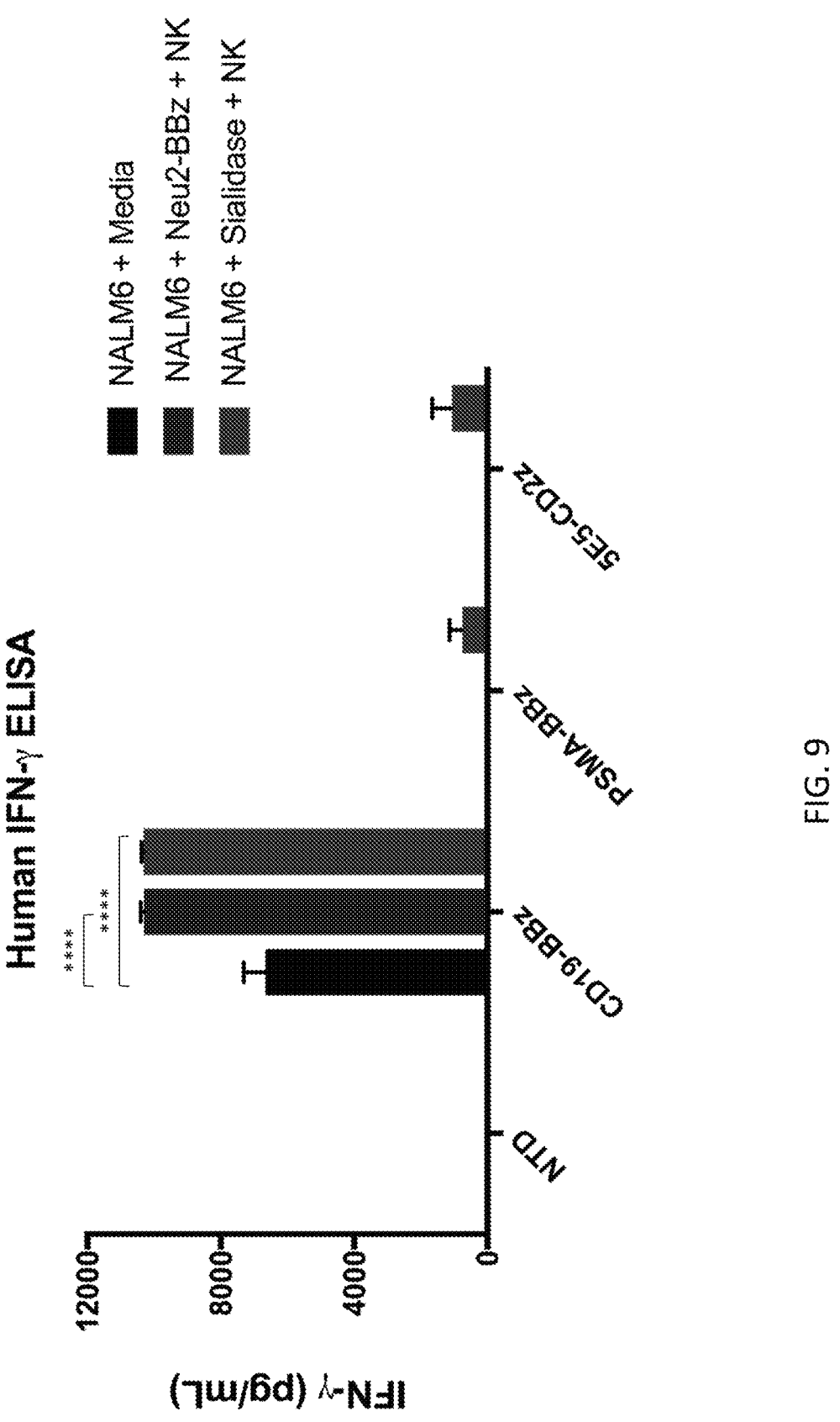
FIG. 9 depicts the finding that engineered Neu2-BBz T cells or sialidase activity can also enhance the anti-tumor activity of CD19-BBz treatment against leukemic cells. CD19-BBz CART cell effector function can be enhanced with the addition of neuraminidase-expressing T cells and NK cells, much like in cultures with bacterial sialidase and NK cells (no significant difference between treatment with the addition of Neu2-BBz+NK and Sialidase+NK). This data demonstrates the potential for the invention to enhance CAR-T cell immunotherapies beyond the 5E5-CAR.
Figure 10:
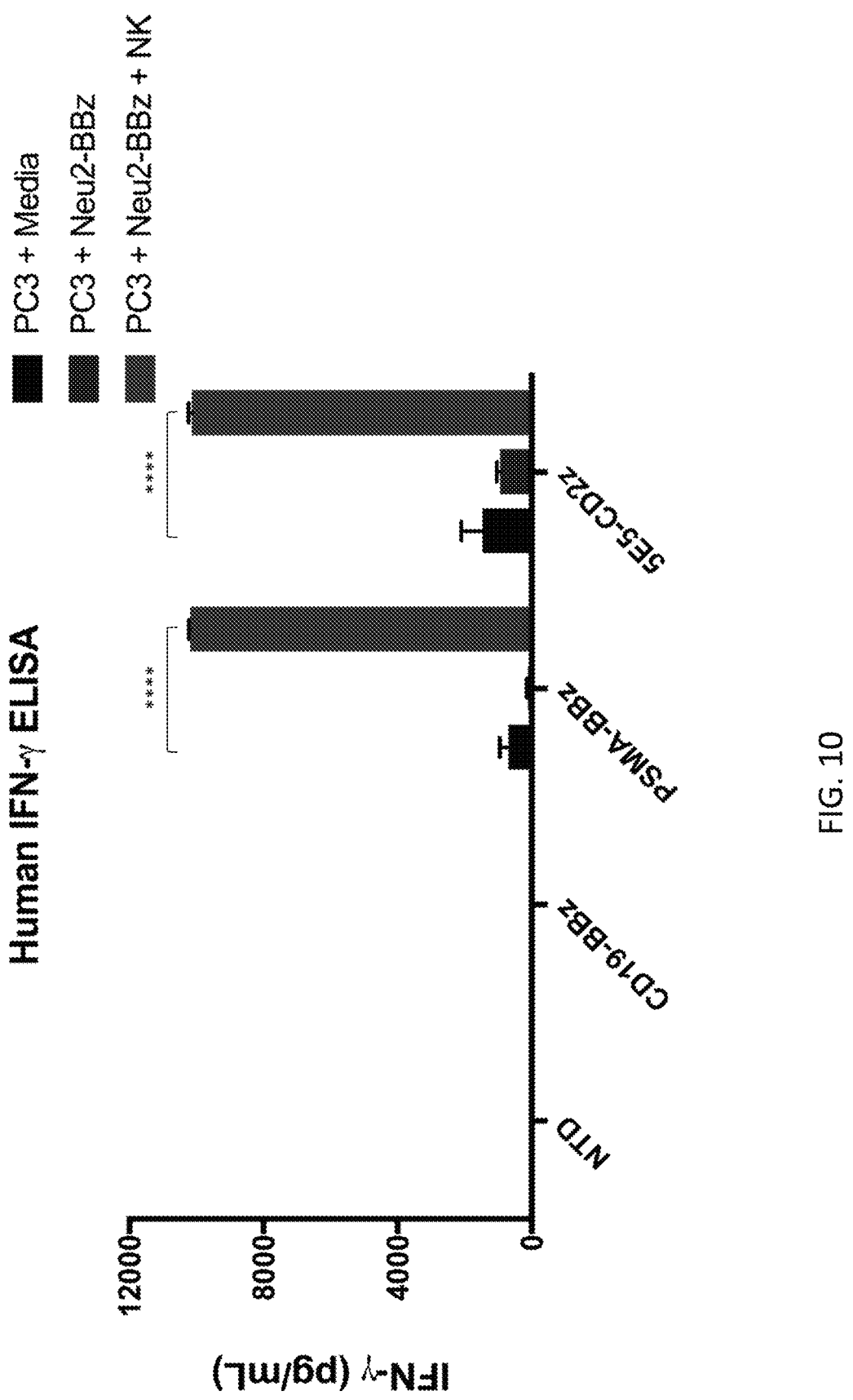
FIG. 10 depicts the finding that engineered Neu2-BBz T cells can enhance the anti-tumor activity of prostate cancer CART treatment. The reactivity of PSMA-BBz CART cells and 5E5-CART cells against aggressive prostate cancer cell line PC3 is significantly increased by human sialidase/neuraminidase T cells and NK cells.

Cytokine Secretion: 5E5-CD2z CAR T cells were incubated with PC3 target cells at a 1:1 ratio either alone, or with the addition of Sialidase and NK cells individually, or the combination of the CAR T cells, Sialidase, and NK cells (as indicated in FIG. 7) for 16 hrs in R10 medium at 37° C. NTD T cells were used as a control in the same conditions. CD19-BBz, PSMA-BBz, and 5E5-CD2z CAR T cells were incubated with NALM6 target cells at a 1:1 ratio either alone or with Neu2-BBz T cells+NK cells, or Sialidase+NK cells (as indicated in FIG. 9) for 16 hrs in R10 medium. NTD T cells were used as a control under the same conditions. CD19-BBz, PSMA-BBz, and 5E5-CD2z CAR T cells were incubated with PC3 target cells at a 1:1 ratio either alone or with Neu2-BBz T cells, or with Neu2-BBz T cells+NK cells (as indicated in FIG. 10). NTD T cells were used as a control under the same conditions. After 16 hrs, supernatant was collected and analyzed for IFN-γ production using the Human DuoSet ELISA kit (R&D Systems).

Cytotoxicity Assays: Cytotoxicity assays were performed using the xCELLigence real-time cell analysis (RTCA) system, which measures rate of de-adherence as target cells are lysed/undergo cytolytic responses after the addition of cytolytic cells. Adherent PC3 target cells in culture were suspended using trypsin (0.05%) and counted on a Beckman Coulter multisizer Coulter Counter, then 1E4 PC3 target cells were plated on an xCELLigence assay E-plate and allowed to adhere overnight at 37° C. After overnight incubation, T cells, NK cells and sialidase were added at the indicated effector:target ratios (FIG. 8), and co-cultures were returned to 37° C., and de-adherence data was monitored and recorded automatically and continuously for 7 days.

Neuraminidase (Sialidase) Activity Assays:

Flow-based surface sialic acid detection using SNA-lectin staining: PC3 tumor cells were treated with *Clostridium perfringens*-derived sialidase (500 U of α2-3,6,8 Neuraminidase from New England BioLabs) for one hour ate 37° C. Cells were allowed to recover for either a 2-hour, or 1-hour period, or no recovery time to restore surface sialic acid expression. Non-treated PC3 cells were used as a control. Surface expression of sialic acid was investigated by flow cytometry of SNA-lectin staining after treatment and recovery periods, and staining intensity of the non-treated group was compared to treatment groups. Neuraminidase activity of engineered T cells was assessed against PC3 and DU145 tumor cells. Cells were co-cultured at indicated effector:target ratios (FIG. 6) for 24 hrs at 37° C. with Neu2-BBz T cells and NTD T cell controls. Sialic acid expression was assessed using SNA-lectin staining and flow cytometric analysis comparing PC3 and DU145 cells co-cultured with either NTD or Neu2-BBz T cells. Fluorometric Assay for Sialidase Activity (using the artificial substrate 4-MU-NANA): 293T cells were transfected with 2.5 ug of the each of the following lentiviral sialidase expressing constructs and a lipofectamine/Opti-MEM mixture—pTRPE-Myc-Neu1-Dz, pTREP-Myc-Neu2-Dz, pTRPE-Myc-Neu3-Dz, pTRPE-Myc-Neu4Dz, and pTREP-Myc-Neu2-BBz, and one sample was left non-transfected as a control. Cells were incubated for 24 hours, and then $2\times10^6$ 293T cells from each of the samples were harvested and washed 3× with PBS and pelleted with gentle centrifugation. Cells were resuspended in assay buffer as described in Leang and Hurt, 2017, and 100 µL of each sample was plated in a black flat-bottom 96 well plate in duplicate. In order to generate a standard curve of relative fluorescence units (RFU) of 4-MU and an equation for which to derive the unknown sialidase activity of each receptor, serial dilutions of *Clostridium perfringens*-derived sialidase (from 0.5 U to OU of enzyme) were added to the plate in duplicate, and suspended in the same assay buffer. The artificial substrate 4-MU-NANA was added to each of the wells as described in Leang and Hurt, 2017. The plate was taped to mix, covered, and incubated for 1 hour at 37° C. After incubation, the reaction was terminated with a stop solution (Leang and Hurt, J Vis Exp. 2017; (122):55570. Published 2017 Apr. 15. doi:10.3791/55570) and sialidase activity was determined by measuring the fluorescence intensity of released 4-MU with a fluorescence plate reader (fluorescence spectrophotometer; excitation at 355 nm; emission at 460 nm).

Example 1: Engineered Expression of Cell Surface and Secreted Sialidase by CART Cells for Increased Efficacy in Solid Tumors CAR T cells have lacked efficacy in the treatment of solid tumors due to a number of challenges, including overcoming the dense immunosuppressive tumor stroma and post-translational modifications on the tumor that favor tumor survival. The work presented herein improves CAR T cell therapy against solid tumors by enhancing cytotoxic effects of endogenous and unmodified immune cells by engineering sialidase function on CAR T cells. T cells bearing sialidase/neuraminidase activity can cleave inhibitory sialic acids on tumor cells, thereby enhancing the anti-tumor efficacy of Siglec-expressing innate immune cells, such as NK and monocytes (FIGS. 1A-1C). In one iteration, the CAR T cell comprises a cell-surface receptor comprising a sialidase/neuraminidase domain along with T cell signaling domains from 4-1BB and CD3zeta (FIG. 1A). In another iteration, the CAR T cell comprises a cell-surface receptor without intracellular T cell signaling domains (FIG. 1B). In a third iteration, the CAR T cell comprises secreted sialidase activity (FIG. 1C).

Figure 2:
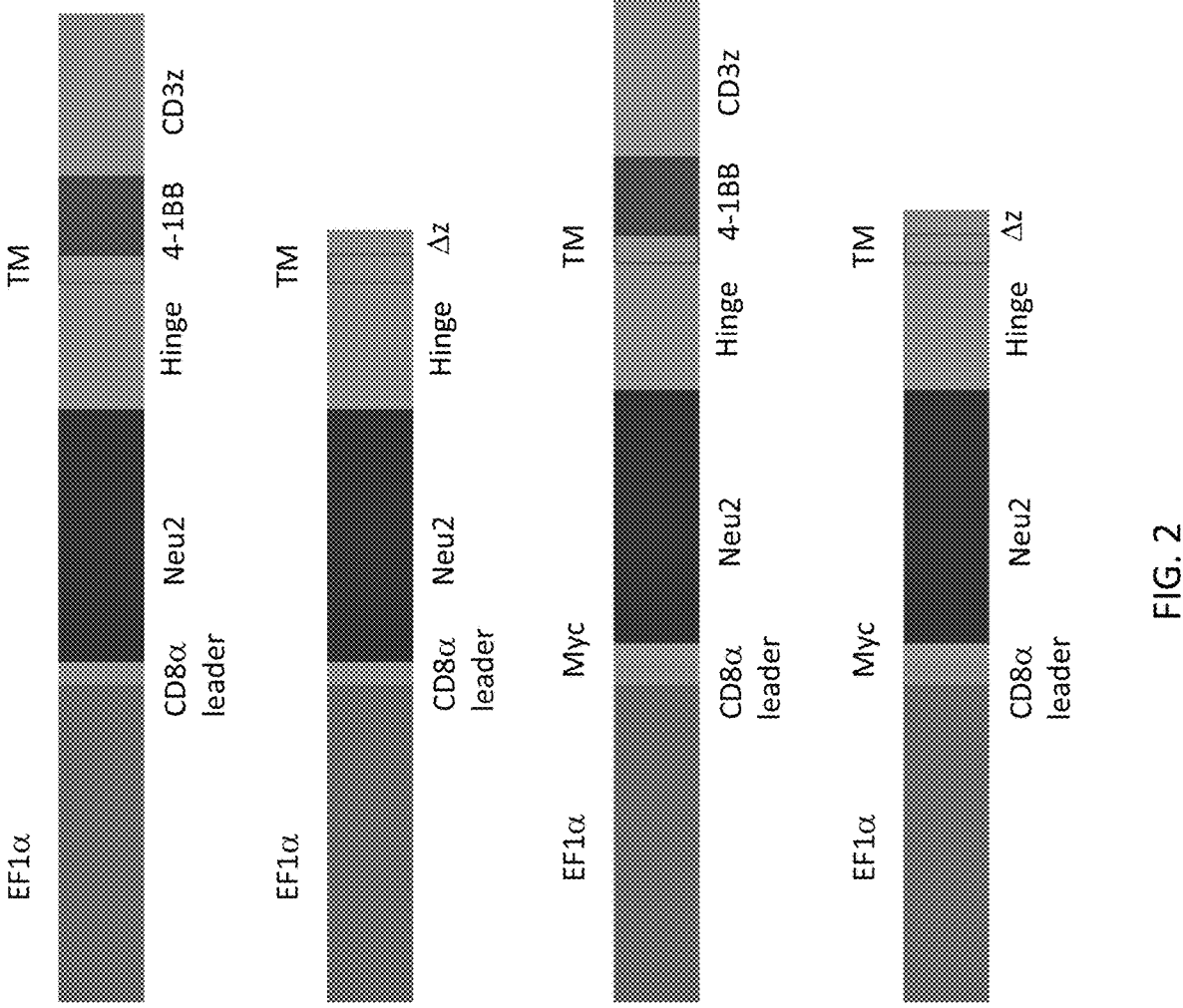
FIG. 2 depicts chimeric siladase/neuraminidase constructs. Constructs include pTRPE-Neu2-BBz, pTRPE-Neu2-Dz, pTRPE-Myc-Neu2-BBz, pTRPE-Myc-Neu2-Dz, Neu2, Neu1, Neu3, Neu4, and 5E5-P2A-Neu2.
Figure 3:
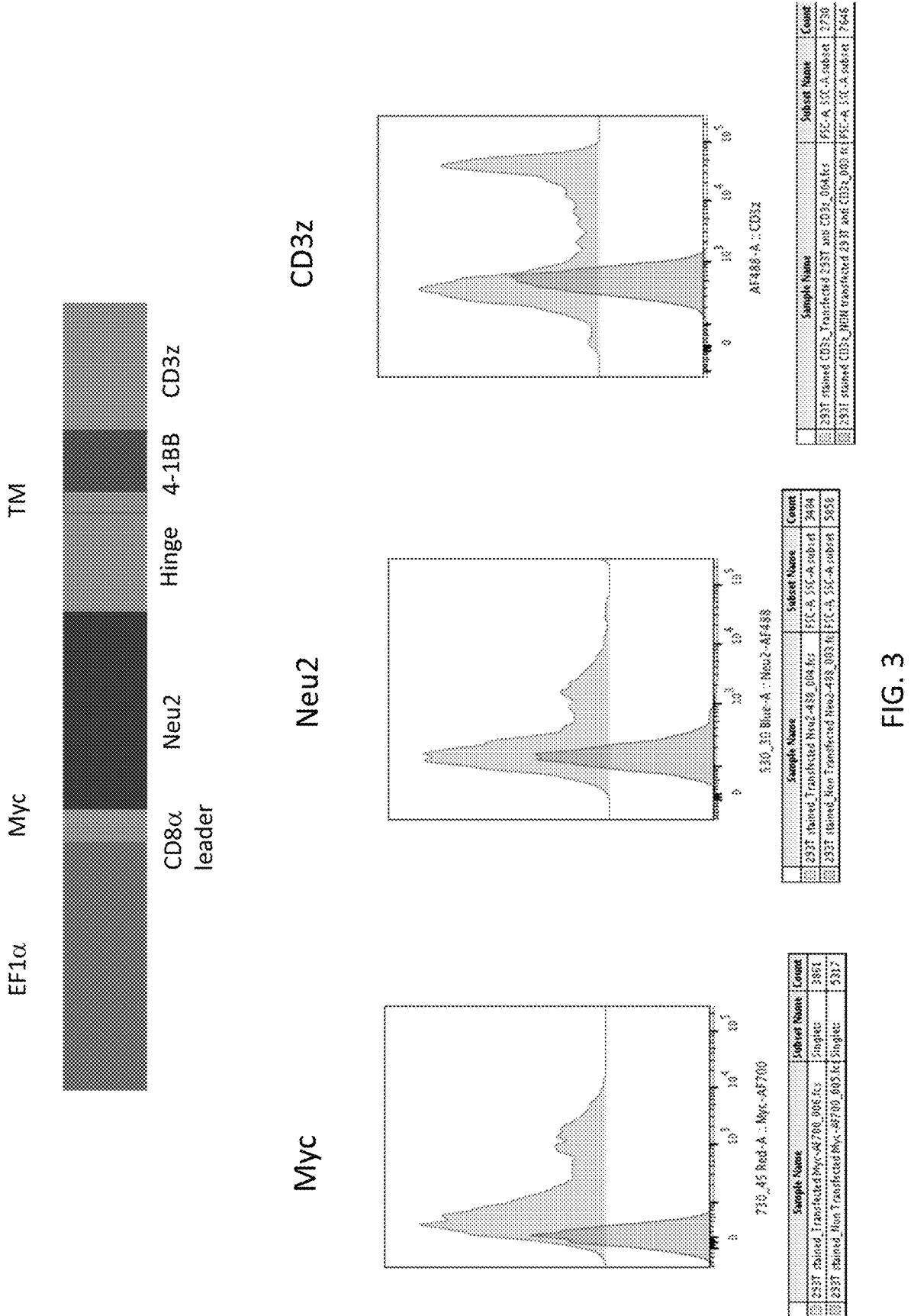
FIG. 3 depicts surface detection of 293T cells transfected with the Myc-Tagged Neu2-BBz construct.

Various neuraminidase (Neu) receptor (chimeric cell surface sialidase) constructs were generated (FIG. 2) including pTRPE-Neu2-BBz (SEQ ID NOs: 1 & 10), pTRPE-Neu2-Dz (SEQ ID NOs: 19 & 21), pTRPE-Myc-Neu2-BBz (SEQ ID NOs: 23 & 25), and pTRPE-Myc-Neu2-Dz (SEQ ID NO: 27 & 28). Additional constructs were generated which replaced the Neu2 domain (SEQ ID NO: 4 or 13) with a Neu1 (SEQ ID NO: 29 or 33), Neu3 (SEQ ID NO: 31 or 33), or Neu4 (SEQ ID NO: 32 or 36) domain (FIG. 2). The construct 5E5-P2A-Neu2 was also generated (FIG. 2). Constructs were transfected into HEK 293T cells and surface expression was detected (FIG. 3).

Figure 4:
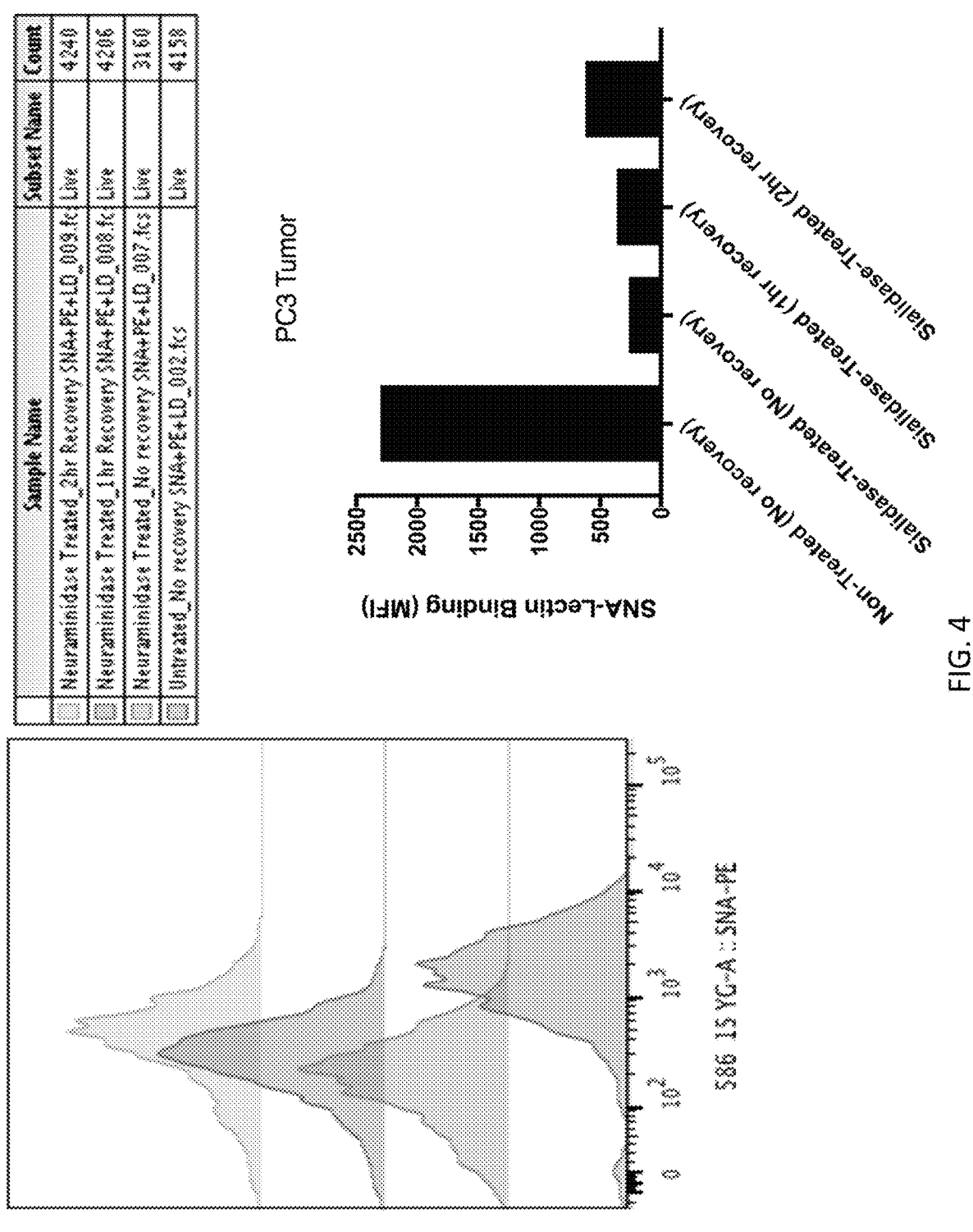
FIG. 4 depicts surface expression of sialic acid on PC3 cells after purified sialidase treatment and recovery periods. This figure demonstrates cleavage of sialic acid from the surface of PC3 tumor cells using sialidase enzyme derived from *Clostridium perfringens*. The bottom-most flow cytometry histogram represents SNA lectin staining on PC3 cells that were not treated with sialidase, a staining control for sialic acid on PC3 cells. The histogram third from the top represents PC3 cells that were treated with sialidase for 1 hr at 37 degrees C. and given no recovery time to restore surface sialic acid expression. There is a significant decrease in MFI for SNA staining on these cells. SNA staining after one hour and 2-hour recovery periods demonstrate sialic acid increase with recovery time (the top two histograms respectively). The changes in MFI are plotted in the bar graph.

PC3 tumor cells were treated with the sialidase enzyme derived from *Clostridium perfringens* for 1 hr at 37 degrees C. (FIG. 4). Cells were given either a 2-hour recovery time, a 1-hour recovery time, or no recovery time to restore surface sialic acid expression. PC3 cells that were not treated with sialidase were used as a control. Surface expression of sialic acid was measured on PC3 cells after the sialidase treatment and recovery periods using flow cytometry. The bottom-most flow cytometry histogram in FIG. 4 represents SNA lectin staining on PC3 cells that were not treated with sialidase, a staining control for sialic acid on PC3 cells.

There was a significant decrease in MFI for SNA staining on PC3 cells that were treated with sialidase for 1 hr at 37 degrees C. and given no recovery time to restore surface sialic acid expression (FIG. 4). SNA staining after one hour and 2-hour recovery periods demonstrated that sialic acid increased with recovery time (FIG. 4).

Figures 5A, 5B, 5C, 5D, 5E, 5F:
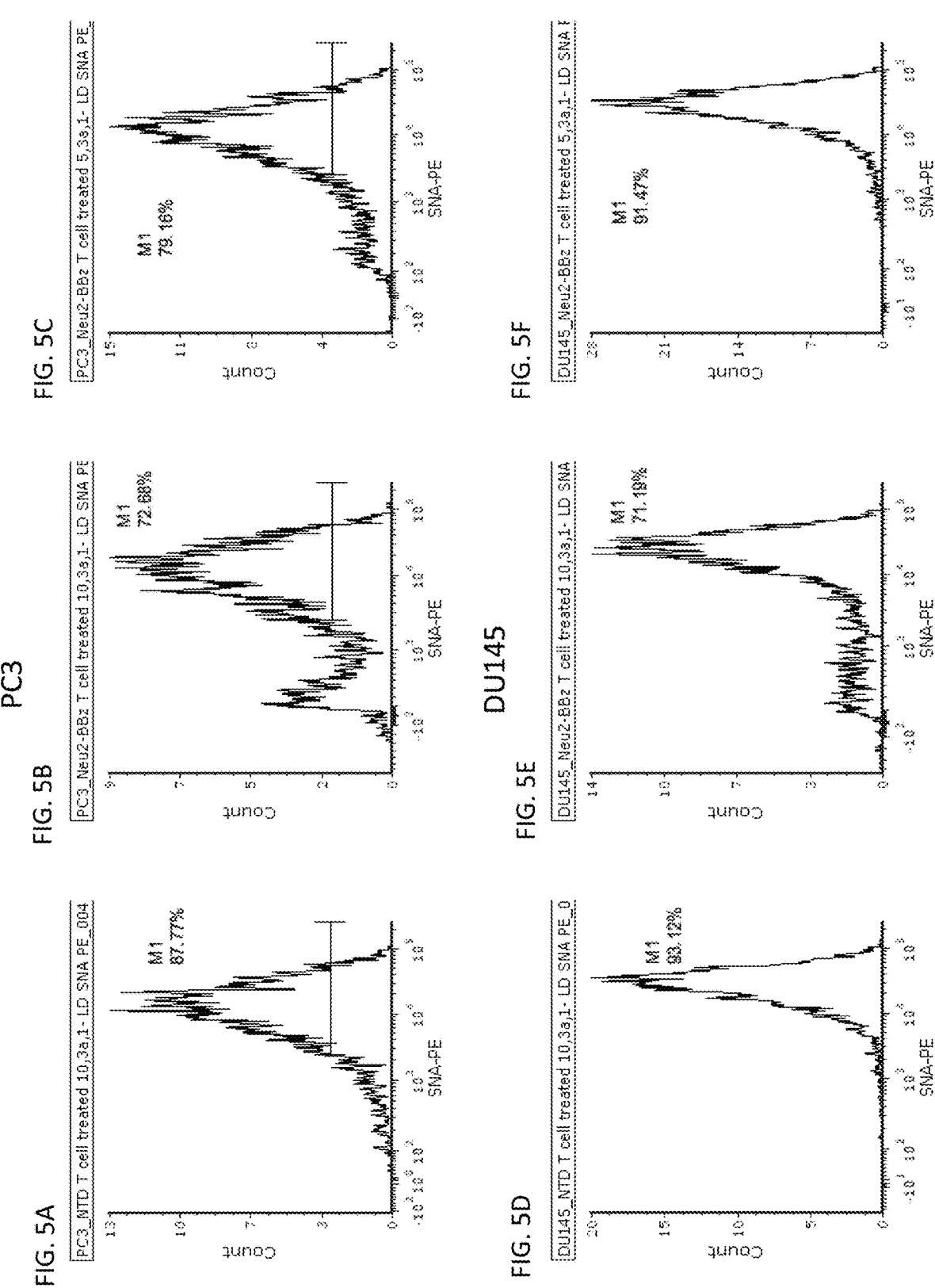
FIGS. 5A-5F depict the finding that engineered Neu2-BBz T cells demonstrate sialidase activity after 24 hr co-culture. Human sialidase/neuraminidase-expressing T cells exhibit the ability to reduce surface sialic acid expression after co-culture with PC3 and DU145 tumor cells, as evidenced by SNA staining. There is a decrease in SNA staining after co-culture with Neu2-BBz T cells compared with NTD T cells (FIG. 5B compared to FIG. 5A.
Figure 6:
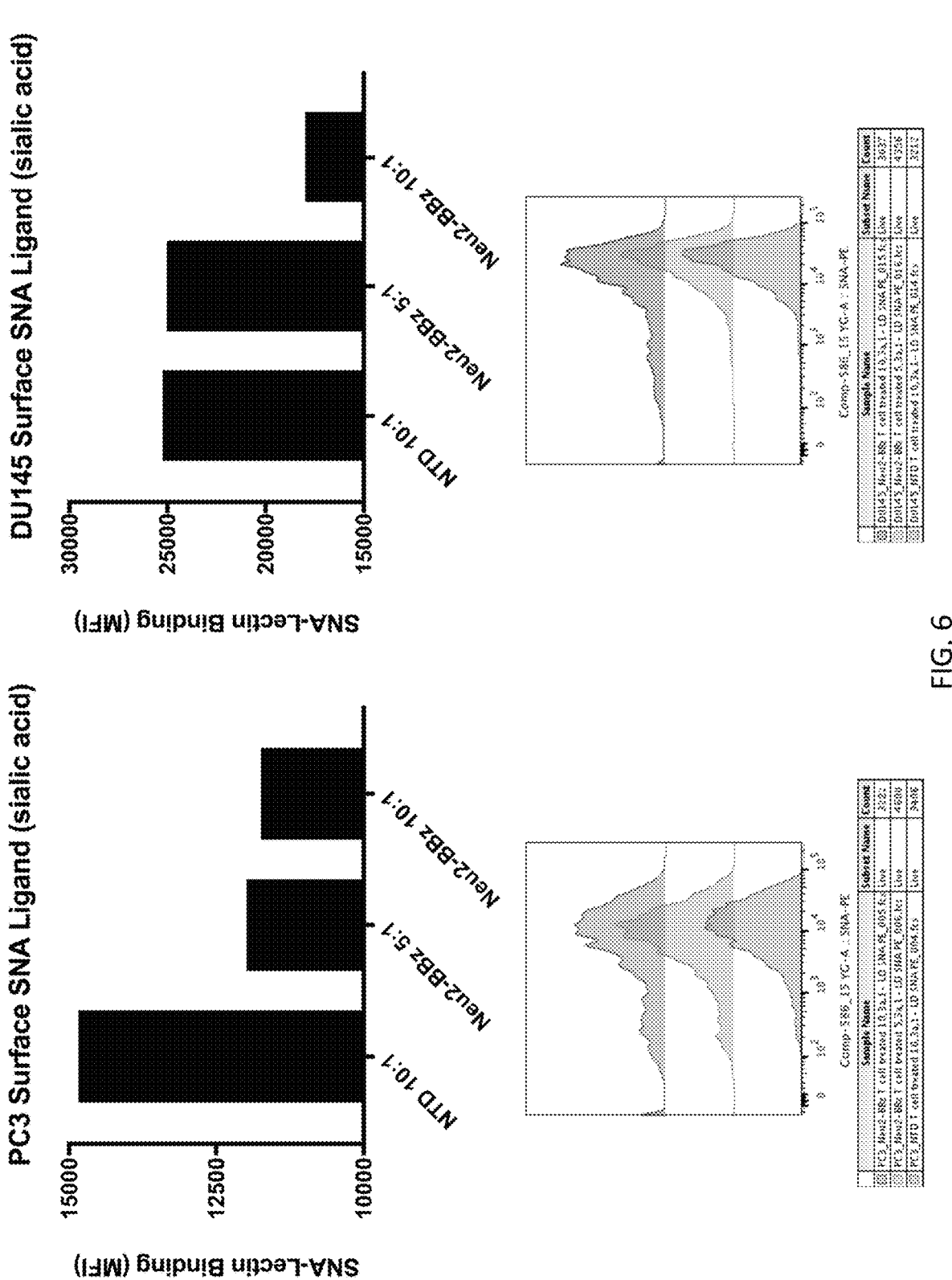
FIG. 6 depicts 24 hr co-culture analysis repeated comparing MFI.

Human sialidase/neuraminidase-expressing T cells exhibited the ability to reduce surface sialic acid expression after 24 hr co-culture with PC3 and DU145 tumor cells, as evidenced by SNA staining (FIGS. 5A-5F). There is a decrease in SNA staining after co-culture with Neu2-BBz T cells compared with NTD T cells (FIG. 5B compared to FIG. 5A; FIG. 5E compared to FIG. 5D). FIGS. 5B and 5E represent a 10:1 effector:target ratio of Neu2-BBz T cells: tumor, and show greater activity compared with FIGS. 5C and 5F, which represent a 5:1 effector:target ratio of Neu2-BBz T cells to tumor cells. The 24 hr co-culture analysis was repeated and MFI compared (FIG. 6).

The addition of sialidase and NK cells enhanced IFN-g production of CART cells targeting prostate cancer PC3 cells (FIG. 7). 5E5-CD2z CART cells demonstrated reactivity to PC3 prostate cancer cells in co-culture alone. Interestingly, IFN-g secretion was elevated when both sialidase and NK cells were added at the time of co-culture with 5E5-CD2z CART cells. This combination approach showed greater reactivity than with each effector condition alone (FIG. 7).

Figures 8A, 8B, 8C:
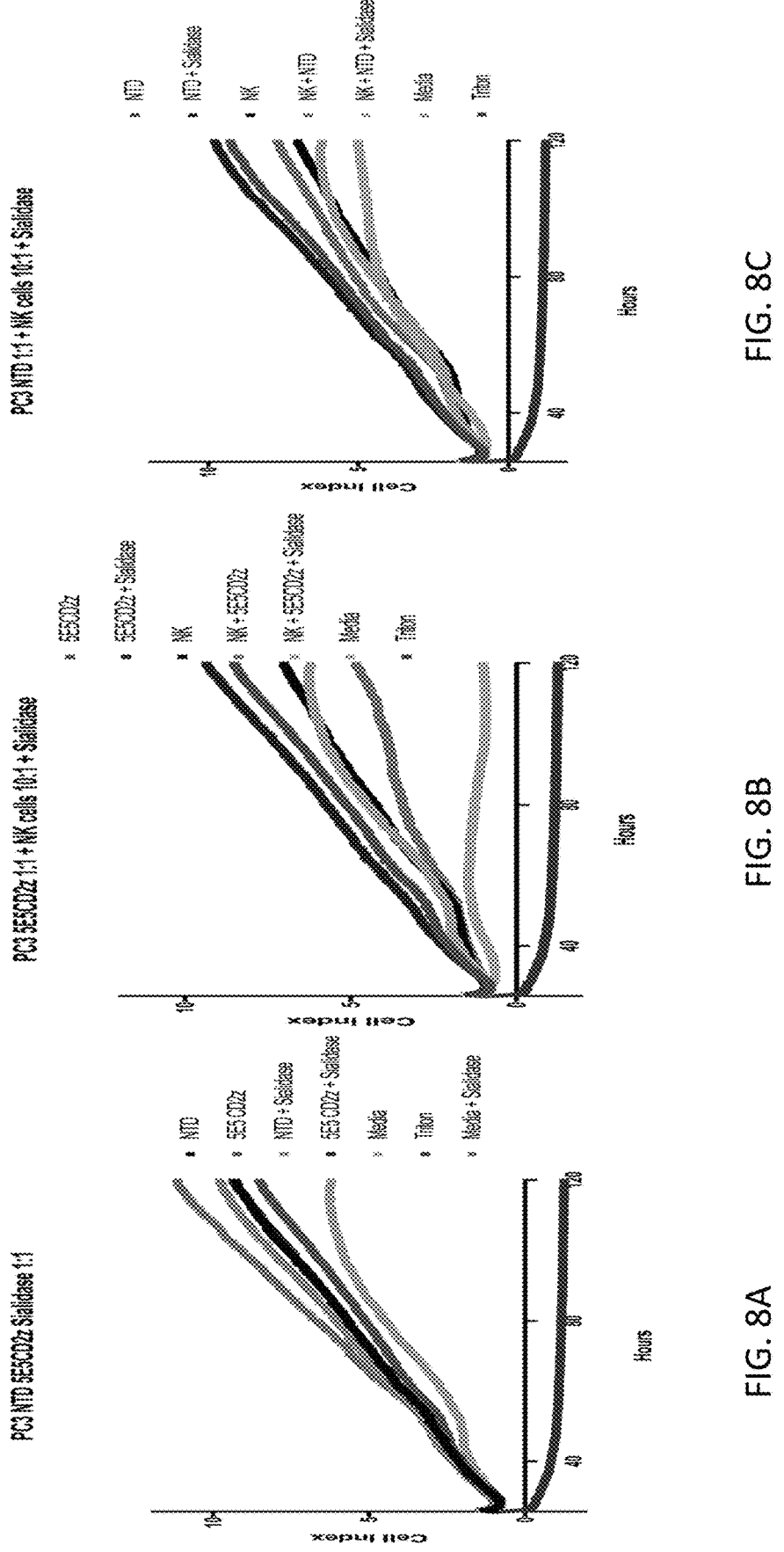
FIG. 8A-8C depicts the finding that sialidase activity promotes synergistic cytotoxicity effects of CART and NK cells. Results from cytotoxicity assays of PC3 prostate cancer cells cultured with human T cells are shown.

Sialidase activity promoted synergistic cytotoxicity effects of CART and NK cells (FIGS. 8A-8C). Cytotoxicity assays of PC3 prostate cancer cells cultured with human T cells were performed. At 1:1 effector:target ratio, 5E5-CD2z CAR T cells and NTD T cells exhibited no cytotoxic effects against PC3 tumor cells (FIG. 8A). There was no increased cytotoxicity through the addition of sialidase or NK cells to the 5E5-CART cells (FIG. 8B). However, when sialidase AND NK cells were added to the 5E5-CART cells, there was virtually complete lysis of PC3 cells, approximating that of the positive lysis control, Triton. Of note, this effect was not observed with 5E5-CART alone, NK cells alone, 5E5-CART+ sialidase, or 5E5-CART+NK cells. The synergy of T cells, NK cells, and sialidase activity was not observed with NTD T cells, demonstrating that CAR activity was required for increased cytotoxicity from this combination (FIG. 8C) These data suggests that 5E5-CART cell cytotoxicity can cooperate with unmodified innate immune cells, such as NK cells, through the addition of sialidase activity.

Engineered Neu2-BBz T cells or sialidase activity enhanced the anti-tumor activity of CD19-BBz treatment against leukemic cells (FIG. 9). CD19-BBz CART cell effector function was enhanced with the addition of neuraminidase-expressing T cells and NK cells, much like in cultures with bacterial sialidase and NK cells (no significant difference between treatment with the addition of Neu2-BBz+NK and Sialidase+NK). These data demonstrate the potential for the invention to enhance CAR-T cell immunotherapies beyond the 5E5-CAR.

Engineered Neu2-BBz T cells enhanced the anti-tumor activity of prostate cancer CART treatment (FIG. 10). The reactivity of PSMA-BBz CART cells and 5E5-CART cells against aggressive prostate cancer cell line PC3 is significantly increased by human sialidase/neuraminidase T cells and NK cells (FIG. 10).

A novel cell-surface human sialidase was designed and expressed on CART cells targeting Tn-MUC1. Truncated, cancer-specific glycoforms, such as Tn-MUC1, are thought to play a role in decreasing cell-cell interactions and increasing the metastatic potential of cancer cells. Tn-MUC1-

CART (or 5E5-CART) cells induced minimal cytotoxic effects against the aggressive PC3 prostate cancer cell line, when co-cultured alone at equal effector:target ratios. When PC3 cells were treated with a *Clostridium perfringens*-derived sialidase, NK cells and 5E5-CART cells showed enhanced IFN-7 production and improved cytotoxic effects are observed compared with NK cells and 5E5-CART cells alone. Similarly, these effector enhancements were observed in the presence of T cells presenting a human cell-surface sialidase. Taken together, these data demonstrated that gly-coediting of tumor sialic acid presents a rational and unique opportunity to overcome barriers for adoptive immunothera-pies in solid tumors, and engagement of the endogenous immune system by adoptively transferred cells is an effec-tive strategy for improved anti-tumor activity.

The sialidase-expressing CAR presented herein is the first of its kind, and cleaves inhibitory glycans on the tumor cell surface, allowing tumors to be recognized and killed by cells of the endogenous innate immune system, such as NK cells and monocytes, in combination and/or synergy with CAR T cell activity.

Figure 11:
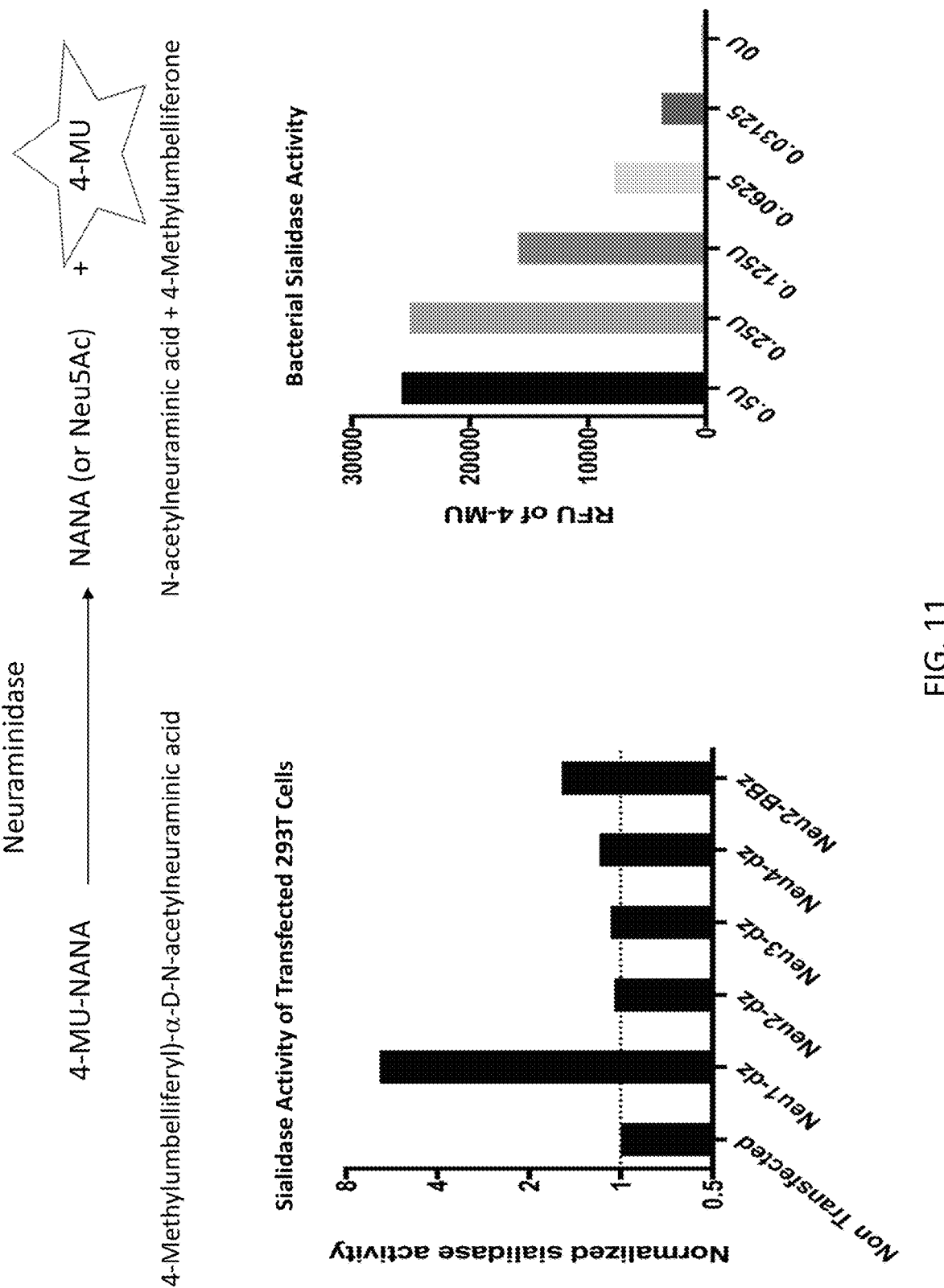
FIG. 11 depicts results from a neuraminidase activity assay that compares the enzymatic function of engineered receptors. A fluorometric neuraminidase functional assay using the artificial substrate 4-MU-NANA. Neuraminidase catalyzes the release of fluorescent 4-MU from 4-MU-NANA, and the fluorescence emissions is quantified. The panel to the left shows the normalized sialidase function of various forms of the neuraminidase receptors present on transfected 293T cells compared to non-transfected. The Neu1-Dz (delta zeta) receptor showed the greatest enzymatic activity followed by Neu2-BBz. The panel to the right shows various units of bacterial sialidase and corresponding function as determined by fluorescence emission. This information was used as a standard when calculating fluorescent readout for activity produced by the receptors.

Example 2: Enzymatic Function of Engineered Receptors is Demonstrated Using a Fluorometric Neuraminidase (Sialidase) Activity Assays Neuraminidase (Sialidase) activity assays were performed to compare the enzymatic function of the engineered recep-tors designed herein (FIG. 11). A fluorometric neuramini-dase functional assay using the artificial substrate 4-MU-NANA was performed. The enzymatic activity of neuraminidase catalyzes the release of 4-MU from 4-MU-NANA, and the florescence emission is quantified. 293T cells were transfected with various forms of the neuramini-dase receptors and sialidase activity was measured. Normal-ized sialidase function of the various receptors compared to non-transfected cells is shown in FIG. 11, left panel. The Neu1-Dz (delta zeta) receptor showed the greatest enzy-matic activity followed by Neu2-BBz. FIG. 11, right panel shows various units of bacterial sialidase and corresponding function as determined by fluorescence emission. This infor-mation was used as a standard when calculating fluorescent readout for activity produced by the receptors. Based on the activity level demonstrated, Neu1-Dz, Neu2-BBz, Neu1-BBz, and Neu1-secreted (when generated) receptor versions were chosen for additional functional assays (both in-vitro and in-vivo).

Based on results from this assay the Neu1-delta zeta vector was used to assess if normal donor human T cells could be successfully transduced, and to evaluate the syn-ergistic effects of CAR-T cells expressing this receptor co-cultured with NK cells against prostate tumor cells.

Example 3: Dual Expressing Human Sialidase-5E5-CAR-T Cells Exhibit Rapid Synergistic Cytotoxicity Against PC3 Tumor Cells when Co-Cultured with NK Cells Normal donor human T cells were transduced with either the single lentiviral vector 5E5-BBz, the single lentiviral vector Myc-NeulDz, or double-transduced with both the 5E5-BBz and Myc-Neu1-Dz lentiviral vectors (referred to as Dual Expressing Sialidase-5E5 T cells) and analyzed by flow cytometry (FIGS. 12A-12D). Non-transduced (NTD) cells were used as a control. Cells were gated on protein L and stained with an anti-Myc tagged antibody (FIG. 12A-12D).

Figures 12A, 12B, 12C, 12D, 12E:
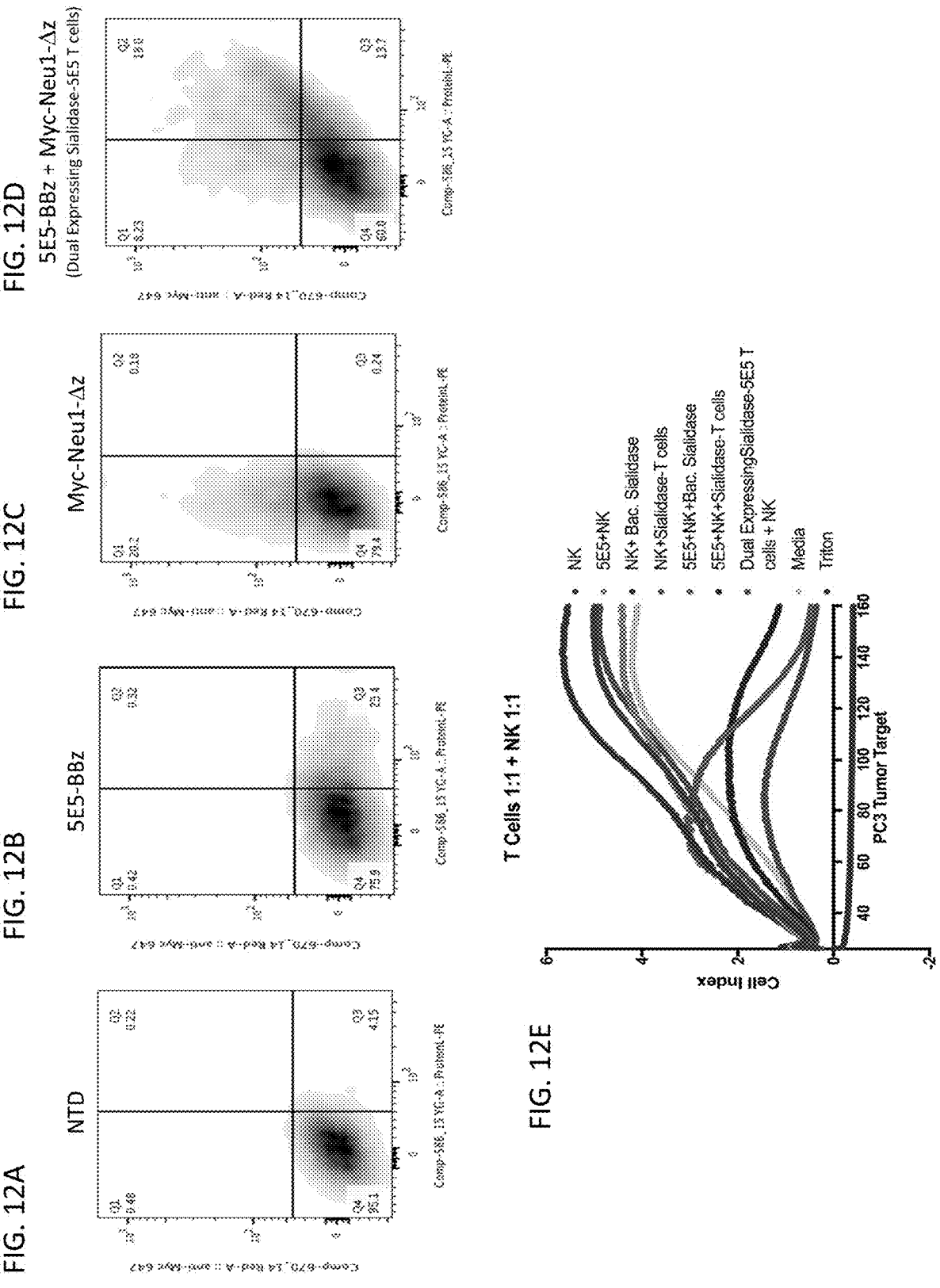
FIGS. 12A-12E depict the finding that dual expressing human sialidase-5E5-CAR-T cells exhibit rapid synergistic cytotoxicity against PC3 tumor cells when co-cultured with NK cells. Normal donor human T cells were lentivirually transduced with the construct indicated. Non-transduced (NTD) cells were used as a control.

Cytotoxic ability was also assessed using xCELLigence RTCA (FIG. 12E). NK cells and effectors listed were co-cultured at a 1:1 ratio with PC3 tumor cells. The 5E5+NK+ Sialidase-T cell group is a 3-product co-culture; whereas the Dual Expressing Sialidase-5E5 T cell+NK group is a 2-cell product consisting of NK cells co-cultured with T cells expressing both the Neuraminidase receptor and the 5E5-CAR.

These data demonstrated that normal donor human T cells can be successfully transduced with an engineered human neuraminidase receptor and confer neuraminidase receptor expression on 5E5-CAR-T cells (FIGS. 12C-12D). Addi-tionally, these dual expressing Sialidase-5E5 T cells are functional, and in co-culture with NK cells show more rapid synergistic cytotoxicity against PC3 tumors than what is observed with the bacterial sialidase control in co-culture with NK and 5E5-CAR-T cells (FIG. 12E).

SEQUENCE LISTING

```
Sequence total quantity: 60
SEQ ID NO: 1              moltype = DNA  length = 1884
FEATURE                  Location/Qualifiers
misc_feature             1..1884
                         note = Neu2-BBz
source                   1..1884
                         mol_type = other DNA
                         organism = synthetic construct
SEQUENCE: 1
atggccttac cagtgaccgc cttgctcctg ccgctggcct tgctgctcca cgccgccagg   60
ccgggatcca tggcttcctt gccggtgctg caaaaagaga gcgtattcca gtcaggcgcc  120
catgcgtata gaatcccggc acttctctat ttgccgggcc aacaaagtct cttggcgttc  180
gcggaacagc gggcgtccaa aaaagacgaa cacgccgagt tgattgtgct ccgccgcggg  240
gattatgatg ccccaacgca tcaggttcag tggcaggcac aagaggtagt cgctcaggcg  300
cgactggatg gacatcggtc aatgaaccca tgtccactgt acgatgctca gacaggtacg  360
ttgtttctgt tcttcatcgc tatccctggg caagtaacag aacaacaaca actgcaaacc  420
agagccaatg taacaagact ctgccaggta actagcactg accacggacg aacgtggtct  480
tcccctagag atcttactga cgccgcaatc gggcctgcat atcgcgaatg gagcactttc  540
gcagtaggcc ctggtcattg cctgcaactc catgatcgcg cccgatcact tgtggtgcca  600
gcgtacgcat accggaagct ccatccaata caacgcccca tcccgtccgc tttttgtttc  660
ctctcccatg accacgggcg gacttgggcg cggggtcatt tcgtcgcaca ggatacgttg  720
gagtgtcagg tagcggaagt agaaaccggg gagcagagag tggtcactct caacgcgcgc  780
agtcatcttc gcgcccgcgt acaggcgcag agcactaatg acgggcttga ttttcaagaa  840
agtcaactcg tcaaaaagtt ggttgaaccg ccccgcagg gctgtcaagg ttcagttata  900
agttttccaa gtccacgctc cggtccagga tcaccagcac agtggcttct ctacacccat  960
```

-continued

```
cccacccaca gctggcagcg ggcagatctt ggtgcttact tgaatcccag gccaccggcc   1020
cccgaagcct ggagcgagcc tgtactgctt gcaaaggga gctgtgcgta ctctgatctc      1080
cagtcaatgg gtactggacc agatgggagt ccattgtttg gttgtctcta cgaggcgaac    1140
gattatgagg aaatcgtttt tcttatgttt actttgaaac aggcgttccc agccgaatat    1200
ttgcctcagt ccggaaccac gacgccagcg ccgcgaccac caacaccggc gcccaccatc     1260
gcgtcgcagc ccctgtccct gcgcccagag gcgtgccggc cagcggcggg gggcgcagtg    1320
cacacgaggg ggctggactt cgcctgtgat atctacatct gggcgcccct ggccgggact     1380
tgtgggggtcc ttctcctgtc actggttatc acccctttact gcaaacgggg cagaaagaaa   1440
ctcctgtata tattcaaaca accatttatg agaccagtac aaactactca agaggaagat   1500
ggctgtagct gccgatttcc agaagaagaa gaaggaggat gtgaactgag agtgaagttc     1560
agcaggagcg cagacgcccc cgcgtacaag cagggccaga accagctcta taacgagctc      1620
aatctaggac gaagagagga gtacgatgtt ttggacaaga gacgtggccg ggaccctgag     1680
atggggggaa agccgagaag gaagaaccct caggaaggcc tgtacaatga actgcagaaa     1740
gataagatgg cggaggccta cagtgagatt gggatgaaag gcgagcgccg gaggggcaag    1800
gggcacgatg gcctttacca gggtctcagt acagccacca aggacaccta cgacgccctt    1860
cacatgcagg ccctgcccccc tcgc                                          1884
```

```
SEQ ID NO: 2               moltype = DNA   length = 63
FEATURE                    Location/Qualifiers
misc_feature               1..63
                           note = CD8alpha leader
source                     1..63
                           mol_type = other DNA
                           organism = synthetic construct
SEQUENCE: 2
atggccttac cagtgaccgc cttgctcctg ccgctggcct tgctgctcca cgccgccagg   60
ccg                                                                63
```

```
SEQ ID NO: 3               moltype = AA   length = 4
FEATURE                    Location/Qualifiers
REGION                     1..4
                           note = spacer
source                     1..4
                           mol_type = protein
                           organism = synthetic construct
SEQUENCE: 3
GGSG                                                                4
```

```
SEQ ID NO: 4               moltype = DNA   length = 1140
FEATURE                    Location/Qualifiers
misc_feature               1..1140
                           note = Neu2
source                     1..1140
                           mol_type = other DNA
                           organism = synthetic construct
SEQUENCE: 4
atggcttcct tgccggtgct gcaaaaagag agcgtattcc agtcaggcgc ccatgcgtat   60
agaatcccgg cacttctcta tttgccgggc caacaaagtc tcttggcgtt cgcggaacag   120
cgggcgtcca aaaaagacga acacgccgag ttgattgtgc tccgccgcgg ggattatgat   180
gccccaacgc atcaggttca gtggcaggca caagaggtag tcgctcaggc gcgactggat   240
ggacatcggt caatgaaccc atgtccactg tacgatgctc agacaggtac gttgtttctg   300
ttcttcatcg ctatccctgg gcaagtaaca gaacaacaac aactgcaaac cagagccaat   360
gtaacaagac tctgccaggt aactagcact gaccacggac gaacgtggtc ttcccctaga   420
gatcttactg acgccgcaat cgggcctgca tatcgcgaat ggagcacttt cgcagtaggc   480
cctggtcatt gcctgcaact ccatgatcgc gcccgatcac ttgtggtgcc agcgtacgca   540
taccggaagc tccatccaat acaacgcccc atcccgtccg cttttgtttt cctctcccat   600
gaccacgggc ggacttgggc gcggggtcat ttcgtcgcac aggatacgtt ggagtgtcag   660
gtagcggaag tagaaaccgg ggagcagaga gtggtcactc tcaacgcgcg cagtcatctt   720
cgcgcccgcg tacaggcgca gagcactaat gacgggcttg attttcaaga aagtcaactc   780
gtcaaaaagt tggttgaacc gccccgcag ggctgtcaag gttcagttat aagttttcca   840
agtccacgct ccggtccagg atcaccagca cagtggcttc tctacaccca tcccacccac    900
agctggcagc gggcagatct tggtgcttac ttgaatccca gccaccggcc cccgaagcc     960
tggagcgagc ctgtactgct tgcaaaggg agctgtgcgt actctgatct ccagtcaatg    1020
ggtactggac cagatgggag tccattgttt ggttgtctct acgaggcgaa cgattatgag   1080
gaaatcgttt ttcttatgtt tactttgaaa caggcgttcc cagccgaata tttgcctcag   1140
```

```
SEQ ID NO: 5               moltype = AA   length = 5
FEATURE                    Location/Qualifiers
REGION                     1..5
                           note = spacer
source                     1..5
                           mol_type = protein
                           organism = synthetic construct
SEQUENCE: 5
GGSGG                                                              5
```

```
SEQ ID NO: 6               moltype = DNA   length = 132
FEATURE                    Location/Qualifiers
```

-continued

```
misc_feature            1..132
                        note = CD8alpha hinge
source                  1..132
                        mol_type = other DNA
                        organism = synthetic construct
SEQUENCE: 6
accacgacgc cagcgccgcg accaccaaca ccggcgccca ccatcgcgtc gcagcccctg     60
tccctgcgcc cagaggcgtg ccggccagcg gcgggggggcg cagtgcacac gaggggggctg   120
gacttcgcct gt                                                        132

SEQ ID NO: 7            moltype = DNA   length = 75
FEATURE                 Location/Qualifiers
misc_feature            1..75
                        note = transmembrane domain
source                  1..75
                        mol_type = other DNA
                        organism = synthetic construct
SEQUENCE: 7
gatatctaca tctgggcgcc cttggccggg acttgtgggg tccttctcct gtcactggtt     60
atcacccttt actgc                                                      75

SEQ ID NO: 8            moltype = DNA   length = 126
FEATURE                 Location/Qualifiers
misc_feature            1..126
                        note = 4-1BB ICD
source                  1..126
                        mol_type = other DNA
                        organism = synthetic construct
SEQUENCE: 8
aaacggggca gaaagaaact cctgtatata ttcaaacaac catttatgag accagtacaa     60
actactcaag aggaagatgg ctgtagctgc cgatttccag aagaagaaga aggaggatgt    120
gaactg                                                              126

SEQ ID NO: 9            moltype = DNA   length = 336
FEATURE                 Location/Qualifiers
misc_feature            1..336
                        note = CD3 zeta
source                  1..336
                        mol_type = other DNA
                        organism = synthetic construct
SEQUENCE: 9
agagtgaagt tcagcaggag cgcagacgcc cccgcgtaca agcagggcca gaaccagctc     60
tataacgagc tcaatctagg acgaagagag gagtacgatg ttttggacaa gagacgtggc    120
cgggaccctg agatgggggg gaaagccgaga aggaagaacc ctcaggaagg cctgtacaat    180
gaactgcaga aagataagat ggcggaggcc tacagtgaga ttgggatgaa aggcgagcgc    240
cggagggggca aggggcacga tggcctttac caggtctca gtacagccac caaggacacc     300
tacgacgccc ttcacatgca ggccctgccc cctcgc                             336

SEQ ID NO: 10           moltype = AA   length = 628
FEATURE                 Location/Qualifiers
REGION                  1..628
                        note = Neu2-BBz
source                  1..628
                        mol_type = protein
                        organism = synthetic construct
SEQUENCE: 10
MALPVTALLL PLALLLHAAR PGSMASLPVL QKESVFQSGA HAYRIPALLY LPGQQSLLAF      60
AEQRASKKDE HAELIVLRRG DYDAPTHQVQ WQAQEVVAQA RLDGHRSMNP CPLYDAQTGT     120
LFLFFIAIPG QVTEQQQLQT RANVTRLCQV TSTDHGRTWS SPRDLTDAAI GPAYREWSTF     180
AVGPGHCLQL HDRARSLVVP AYAYRKLHPI QRPIPSAFCF LSHDHGRTWA RGHFVAQDTL     240
ECQVAEVETG EQRVVTLNAR SHLRARVQAQ STNDGLDFQE SQLVKKLVEP PPQGCQGSVI     300
SFPSPRSGPG SPAQWLLYTH PTHSWQRADL GAYLNPRPPA PEAWSEPVLL AKGSCAYSDL     360
QSMGTGPDGS PLFGCLYEAN DYEEIVFLMF TLKQAFPAEY LPQSGTTTPA PRPPTPAPTI     420
ASQPLSLRPE ACRPAAGGAV HTRGLDFACD IYIWAPLAGT CGVLLLSLVI TLYCKRGRKK     480
LLYIFKQPFM RPVQTTQEED GCSCRFPEEE EGGCELRVKF SRSADAPAYK QGQNQLYNEL     540
NLGRREEYDV LDKRRGRDPE MGGKPRRKNP QEGLYNELQK DKMAEAYSEI GMKGERRRGK     600
GHDGLYQGLS TATKDTYDAL HMQALPPR                                       628

SEQ ID NO: 11           moltype = AA   length = 21
FEATURE                 Location/Qualifiers
REGION                  1..21
                        note = CD8alpha leader
source                  1..21
                        mol_type = protein
                        organism = synthetic construct
SEQUENCE: 11
MALPVTALLL PLALLLHAAR P                                               21

SEQ ID NO: 12           moltype = AA   length = 5
```

-continued

```
FEATURE            Location/Qualifiers
REGION             1..5
                   note = linker
REPEAT             1..5
                   note = repeat n times, where n represents an integer of at
                    least 1
source             1..5
                   mol_type = protein
                   organism = synthetic construct
SEQUENCE: 12
GSGGS                                                              5

SEQ ID NO: 13      moltype = AA  length = 380
FEATURE            Location/Qualifiers
REGION             1..380
                   note = Neu2
source             1..380
                   mol_type = protein
                   organism = synthetic construct
SEQUENCE: 13
MASLPVLQKE SVFQSGAHAY RIPALLYLPG QQSLLAFAEQ RASKKDEHAE LIVLRRGDYD  60
APTHQVQWQA QEVVAQARLD GHRSMNPCPL YDAQTGTLFL FFIAIPGQVT EQQQLQTRAN  120
VTRLCQVTST DHGRTWSSPR DLTDAAIGPA YREWSTFAVG PGHCLQLHDR ARSLVVPAYA  180
YRKLHPIQRP IPSAFCFLSH DHGRTWARGH FVAQDTLECQ VAEVETGEQR VVTLNARSHL  240
RARVQAQSTN DGLDFQESQL VKKLVEPPPQ GCQGSVISFP SPRSGPGSPA QWLLYTHPTH  300
SWQRADLGAY LNPRPPAPEA WSEPVLLAKG SCAYSDLQSM GTGPDGSPLF GCLYEANDYE  360
EIVFLMFTLK QAFPAEYLPQ                                              380

SEQ ID NO: 14      moltype = AA  length = 4
FEATURE            Location/Qualifiers
REGION             1..4
                   note = linker
REPEAT             1..4
                   note = repeat n times. where n represents an integer of at
                    least 1
source             1..4
                   mol_type = protein
                   organism = synthetic construct
SEQUENCE: 14
GGGS                                                               4

SEQ ID NO: 15      moltype = AA  length = 41
FEATURE            Location/Qualifiers
REGION             1..41
                   note = CD8alpha hinge
source             1..41
                   mol_type = protein
                   organism = synthetic construct
SEQUENCE: 15
TTTPAPRPPT PAPTIASQPL SLRPEACRPA AGGAVHTRGL D                      41

SEQ ID NO: 16      moltype = AA  length = 28
FEATURE            Location/Qualifiers
REGION             1..28
                   note = transmembrane domain
source             1..28
                   mol_type = protein
                   organism = synthetic construct
SEQUENCE: 16
FACDIYIWAP LAGTCGVLLL SLVITLYC                                     28

SEQ ID NO: 17      moltype = AA  length = 42
FEATURE            Location/Qualifiers
REGION             1..42
                   note = 4-1BB ICD
source             1..42
                   mol_type = protein
                   organism = synthetic construct
SEQUENCE: 17
KRGRKKLLYI FKQPFMRPVQ TTQEEDGCSC RFPEEEEGGC EL                     42

SEQ ID NO: 18      moltype = AA  length = 112
FEATURE            Location/Qualifiers
REGION             1..112
                   note = CD3 zeta
source             1..112
                   mol_type = protein
                   organism = synthetic construct
```

```
SEQUENCE: 18
RVKFSRSADA PAYKQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 19            moltype = DNA   length = 1461
FEATURE                  Location/Qualifiers
misc_feature             1..1461
                         note = pTRPE-Neu2-Dz
source                   1..1461
                         mol_type = other DNA
                         organism = synthetic construct
SEQUENCE: 19
atggccttac cagtgaccgc cttgctcctg ccgctggcct tgctgctcca cgccgccagg    60
ccgggatcca tggcttcctt gccggtgctg caaaaagaga gcgtattcca gtcaggcgcc    120
catgcgtata gaatcccggc acttctctat ttgccgggcc aacaaagtct cttggcgttc    180
gcggaacagc gggcgtccaa aaaagacgaa cacgccgagt tgattgtgct ccgccgcggg    240
gattatgatg ccccaacgca tcaggttcag tggcaggcac aagaggtagt cgctcaggcg    300
cgactggatg gacatcggtc aatgaaccca tgtccactgt acgatgctca gacaggtacg    360
ttgtttctgt tcttcatcgc tatccctggg caagtaacag aacaacaaca actgcaaacc    420
agagccaatg taacaagact ctgccaggta actagcactg accacggacg aacgtggtct    480
tcccctagag atcttactga cgccgcaatc gggcctgcat atcgcgaatg gagcactttc    540
gcagtaggcc ctggtcattg cctgcaactc catgatcggc cccgatcact tgtggtgcca    600
gcgtacgcat accggaagct ccatccaata caacgcccca tcccgtccgc tttttgtttc    660
ctctcccatg accacgggcg gacttgggcg cggggtcatt tcgtcgcaca ggatacgttg    720
gagtgtcagg tagcggaagt agaaaccggg gagcagagag tggtcactct caacgcgcgc    780
agtcatcttc gcgcccgcgt acaggcgcag agcactaatg acgggcttga ttttcaagaa    840
agtcaactcg tcaaaaagtt ggttgaaccg cccccgcagg gctgtcaagg ttcagttata    900
agttttccaa gtccacgctc cggtccagga tcaccagcac agtggcttct ctacacccat    960
cccacccaca gctggcagcg ggcagatctt ggtgcttact tgaatcccag gccaccggcc    1020
cccgaagcct ggagcgagcc tgtactgctt gcaaaggcga gcgtgcgta ctctgatctc    1080
cagtcaatgg gtactggacc agatgggagt ccattgtttg gttgtctcta cgaggcgaac    1140
gattatgagg aaatcgtttt tcttatgttt actttgaaac aggcgttccc agccgaatat    1200
ttgcctcagt ccggaaccac gacgccagcg ccgcgaccac caacaccggc gcccaccatc    1260
gcgtcgcagc ccctgtccct gcgcccagag gcgtgccggc cagcggcggg gggcgcagtg    1320
cacacgaggg ggctggactt cgcctgtgat atctacatct gggcgccctt ggccgggact    1380
tgtgggggtcc ttctcctgtc actggttatc accctttact gcagagtgaa gttcagcagg    1440
agcgcagacg cccccgcgta a                                             1461

SEQ ID NO: 20            moltype = DNA   length = 39
FEATURE                  Location/Qualifiers
misc_feature             1..39
                         note = delta zeta domain
source                   1..39
                         mol_type = other DNA
                         organism = synthetic construct
SEQUENCE: 20
agagtgaagt tcagcaggag cgcagacgcc cccgcgtaa                          39

SEQ ID NO: 21            moltype = AA   length = 486
FEATURE                  Location/Qualifiers
REGION                   1..486
                         note = pTRPE-Neu2-Dz
source                   1..486
                         mol_type = protein
                         organism = synthetic construct
SEQUENCE: 21
MALPVTALLL PLALLLHAAR PGSMASLPVL QKESVFQSGA HAYRIPALLY LPGQQSLLAF    60
AEQRASKKDE HAELIVLRRG DYDAPTHQVQ WQAQEVVAQA RLDGHRSMNP CPLYDAQTGT    120
LFLFFIAIPG QVTEQQQLQT RANVTRLCQV TSTDHGRTWS SPRDLTDAAI GPAYREWSTF    180
AVGPGHCLQL HDRARSLVVP AYAYRKLHPI QRPIPSAFCF LSHDHGRTWA RGHFVAQDTL    240
ECQVAEVETG EQRVVTLNAR SHLRARVQAQ STNDGLDFQE SQLVKKLVEP PPQGCQGSVI    300
SFPSPRSGPG SPAQWLLYTH PTHSWQRADL GAYLNPRPPA PEAWSEPVLL AKGSCAYSDL    360
QSMGTGPDGS PLFGCLYEAN DYEEIVFLMF TLKQAFPAEY LPQSGTTTPA PRPPTPAPTI    420
ASQPLSLRPE ACRPAAGGAV HTRGLDFACD IYIWAPLAGT CGVLLLSLVI TLYCRVKFSR    480
SADAPA                                                               486

SEQ ID NO: 22            moltype = AA   length = 12
FEATURE                  Location/Qualifiers
REGION                   1..12
                         note = delta zeta domain
source                   1..12
                         mol_type = protein
                         organism = synthetic construct
SEQUENCE: 22
RVKFSRSADA PA                                                        12

SEQ ID NO: 23            moltype = DNA   length = 1914
FEATURE                  Location/Qualifiers
```

-continued

```
misc_feature          1..1914
                      note = pTRPE-Myc-Neu2-BBz
source                1..1914
                      mol_type = other DNA
                      organism = synthetic construct
SEQUENCE: 23
atggccttac cagtgaccgc cttgctcctg ccgctggcct tgctgctcca cgccgccagg    60
ccggaacaga aacttatctc cgaggaagac ctgggatcca tggcttcctt gccggtgctg   120
caaaaagaga gcgtattcca gtcaggcgcc catgcgtata gaatcccggc acttctctat   180
ttgccgggcc aacaaagtct cttggcgttc gcggaacagc gggcgtccaa aaaagacgaa   240
cacgccgagt tgattgtgct ccgccgcggg gattatgatg ccccaacgca tcaggttcag   300
tggcaggcac aagaggtagt cgctcaggcg cgactggatg gacatcggtc aatgaaccca   360
tgtccactgt acgatgctca gacaggtacg ttgtttctgt tcttcatcgc tatccctggg   420
caagtaacag aacaacaaca actgcaaacc agagccatag taacaagact ctgccaggta   480
actagcactg accacggacg aacgtggtct tcccctagag atcttactga cgccgcaatc   540
gggcctgcat atcgcgaatg gagcactttc gcagtaggcc ctggtcattg cctgcaactc   600
catgatcgcg cccgatcact tgtggtgcca gcgtacgcat accggaagct ccatccaata   660
caacgcccca tcccgtccgc tttttgtttc ctctcccatg accacgggcg gacttgggcg   720
cggggtcatt tcgtcgcaca ggatacgttg gagtgtcagg tagcggaagt agaaaccggg   780
gagcagagag tggtcactct caacgcgcgc agtcatcttc gcgcccgcgt acaggcgcag   840
agcactaatg acgggcttga ttttcaagaa agtcaactcg tcaaaaagtt ggttgaaccg   900
cccccgcagg gctgtcaagg ttcagttata agttttccaa gtccacgctc cggtccagga   960
tcaccagcac agtggcttct ctacacccat cccacccaca gctggcagcg ggcagatctt  1020
ggtgcttact tgaatcccag gccaccggcc cccgaagcct ggagcgagcc tgtactgctt  1080
gcaaagggga gctgtgcgta ctctgatctc cagtcaatgg gtactggacc agatgggagt  1140
ccattgtttg gttgtctcta cgaggcgaac gattatgagg aaatcgtttt tcttatgttt  1200
actttgaaac aggcgttccc agccgaatat ttgcctcagt ccggaaccac gacgccagcg  1260
ccgcgaccac caacaccggc gcccaccatc cgctcgcagc ccctgtccct gcgcccagag  1320
gcgtgccggc cagcggcggg gggcgcagtg cacacgaggg ggctggactt cgcctgtgat  1380
atctacatct gggcgccctt ggccgggact tgtgggggtcc ttctcctgtc actggttatc  1440
acccttact gcaaacgggg cagaaagaaa ctcctgtata tattcaaaca accatttatg  1500
agaccagtac aaactactca agaggaagat ggctgtagct gccgatttcc agaagaagaa  1560
gaaggaggat gtgaactgag agtgaagttc agcaggagcg cagacgcccc cgcgtacaag  1620
cagggccaga accagctcta taacgagctc aatctaggac gaagagagga gtacgatgtt  1680
ttggacaaga cggtggccg ggaccctgag atggggggga agccgagaag gaagaaccct  1740
caggaaggcc tgtacaatga actgcagaaa gataagatgg cggaggccta cagtgagatt  1800
gggatgaaag gcgagcgccg gaggggcaag ggcacgatg gcctttacca gggtctcagt  1860
acagccacca aggacaccta cgacgcccct cacatgcagg ccctgccccc tcgc         1914

SEQ ID NO: 24         moltype = DNA  length = 30
FEATURE               Location/Qualifiers
misc_feature          1..30
                      note = Myc-Tag
source                1..30
                      mol_type = other DNA
                      organism = synthetic construct
SEQUENCE: 24
gaacagaaac ttatctccga ggaagacctg                                    30

SEQ ID NO: 25         moltype = AA  length = 638
FEATURE               Location/Qualifiers
REGION                1..638
                      note = pTRPE-Myc-Neu2-BBz
source                1..638
                      mol_type = protein
                      organism = synthetic construct
SEQUENCE: 25
MALPVTALLL PLALLLHAAR PEQKLISEED LGSMASLPVL QKESVFQSGA HAYRIPALLY    60
LPGQQSLLAF AEQRASKKDE HAELIVLRRG DYDAPTHQVQ WQAQEVVAQA RLDGHRSMNP   120
CPLYDAQTGT LFLFFIAIPG QVTEQQQLQT RANVTRLCQV TSTDHGRTWS SPRDLTDAAI   180
GPAYREWSTF AVGPGHCLQL HDRARSLVVP AYAYRKLHPI QRPIPSAFCF LSHDHGRTWA   240
RGHFVAQDTL ECQVAEVETG EQRVVTLNAR SHLRARVQAQ STNDGLDFQE SQLVKKLVEP   300
PPQGCQGSVI SFPSPRSGPG SPAQWLLYTH PTHSWQRADL GAYLNPRPPA PEAWSEPVLL   360
AKGSCAYSDL QSMGTGPDGS PLFGCLYEAN DYEEIVFLMF TLKQAFPAEY LPQSGTTTPA   420
PRPPTPAPTI ASQPLSLRPE ACRPAAGGAV HTRGLDFACD IYIWAPLAGT CGVLLLSLVI   480
TLYCKRGRKK LLYIFKQPFM RPVQTTQEED GCSCRFPEEE EGGCELRVKF SRSADAPAYK   540
QGQNQLYNEL NLGRREEYDV LDKRRGRDPE MGGKPRRKNP QEGLYNELQK DKMAEAYSEI   600
GMKGERRRGK GHDGLYQGLS TATKDTYDAL HMQALPPR                          638

SEQ ID NO: 26         moltype = AA  length = 10
FEATURE               Location/Qualifiers
REGION                1..10
                      note = Myc-Tag
source                1..10
                      mol_type = protein
                      organism = synthetic construct
SEQUENCE: 26
EQKLISEEDL                                                          10
```

```
SEQ ID NO: 27          moltype = DNA   length = 1491
FEATURE                Location/Qualifiers
misc_feature           1..1491
                       note = pTRPE-Myc-Neu2-Dz
source                 1..1491
                       mol_type = other DNA
                       organism = synthetic construct
SEQUENCE: 27
atggccttac cagtgaccgc cttgctcctg ccgctggcct tgctgctcca cgccgccagg   60
ccggaacaga aacttatctc cgaggaagac ctgggatcca tggcttcctt gccggtgctg  120
caaaaagaga gcgtattcca gtcaggcgcc catgcgtata gaatcccggc acttctctat  180
ttgccgggcc aacaaagtct cttggcgttc gcggaacagc gggcgtccaa aaaagacgaa  240
cacgccgagt tgattgtgct ccgccgcggg gattatgatg ccccaacgca tcaggttcag  300
tggcaggcac aagaggtagt cgctcaggcg cgactggatg gacatcggtc aatgaaccca  360
tgtccactgt acgatgctca gacaggtacg ttgtttctgt tcttcatcgc tatccctggg  420
caagtaacag aacaacaaca actgcaaacc agagccaatg taacaagact ctgccaggta  480
actagcactg accacggacg aacgtggtct tccctagat atcttactga cgccgcaatc  540
gggcctgcat atcgcgaatg gagcactttc gcagtagcgc ctggtcattg cctgcaactc  600
catgatcgcg cccgatcact tgtggtgcca cgctacgcat accggaagct ccatccaata  660
caacgcccca tcccgtccgc tttttgtttc ctctcccatg accacgggcg gacttgggcg  720
cggggtcatt tcgtcgcaca ggatacgttg gagtgtcagg tagcggaagt agaaaccggg  780
gagcagagag tggtcactct caacgcgcgc agtcatcttc gcgcccgcgt acaggcgcag  840
agcactaatg acgggcttga ttttcaagaa agtcaactcg tcaaaaagtt ggttgaaccg  900
cccccgcagg gctgtcaagg ttcagttata agttttccaa gtccacgctc cggtccagga  960
tcaccagcac agtggcttct ctacacccat cccacccaca gctggcagcg ggcagatctt 1020
ggtgcttact tgaatcccag gccaccggcc ccgaagcct cccgtcgcaa ctgtactgctt 1080
gcaaagggga gctgtgcgta ctctgatctc cagtcaatgg gtactggacc agatgggagt 1140
ccattgtttg gttgtctcta cgaggcgaac gattatgagg aaatcgtttt tcttatgttt 1200
actttgaaac aggcgttccc agccgaatat ttgcctcagt ccggaaccac gacgccagcg 1260
ccgcgaccac caacaccggc gcccaccatc gcgtcgcaac ccctgtccct gcgcccagag 1320
gcgtgccggc cagcggcggg gggcgcagtg cacacgaggg ggctggactt cgcctgtgat 1380
atctacatct gggcgccctt ggccgggact tgtgggttcc ttctcctgtc actggttatc 1440
acccttttact gcagagtgaa gttcagcagg agcgcagacg cccccgcgta a          1491

SEQ ID NO: 28          moltype = AA   length = 496
FEATURE                Location/Qualifiers
REGION                 1..496
                       note = pTRPE-Myc-Neu2-Dz
source                 1..496
                       mol_type = protein
                       organism = synthetic construct
SEQUENCE: 28
MALPVTALLL PLALLLHAAR PEQKLISEED LGSMASLPVL QKESVFQSGA HAYRIPALLY   60
LPGQQSLLAF AEQRASKKDE HAELIVLRRG DYDAPTHQVQ WQAQEVVAQA RLDGHRSMNP  120
CPLYDAQTGT LFLFFIAIPG QVTEQQQLQT RANVTRLCQV TSTDHGRTWS SPRDLTDAAI  180
GPAYREWSTF AVGPGHCLQL HDRARSLVVP AYAYRKLHPI QRPIPSAFCF LSHDHGRTWA  240
RGHFVAQDTL ECQVAEVETG EQRVVTLNAR SHLRARVQAQ STNDGLDFQE SQLVKKLVEP  300
PPQGCQGSVI SFPSPRSGPG SPAQWLLYTH PTHSWQRADL GAYLNPRPPA PEAWSEPVLL  360
AKGSCAYSDL QSMGTGPDGS PLFGCLYEAN DYEEIVFLMF TLKQAFPAEY LPQSGTTTPA  420
PRPPTPAPTI ASQPLSLRPE ACRPAAGGAV HTRGLDFACD IYIWAPLAGT CGVLLLSLVI  480
TLYCRVKFSR SADAPA                                                   496

SEQ ID NO: 29          moltype = DNA   length = 1131
FEATURE                Location/Qualifiers
misc_feature           1..1131
                       note = Neu1
source                 1..1131
                       mol_type = other DNA
                       organism = synthetic construct
SEQUENCE: 29
ggatcctcct ggagtaaagc cgaaaatgac tttggattgg tgcagccttt ggtcacaatg   60
gaacaacttc tgtgggtcag cgggcggcaa atcggatcag ttgatacttt cagaatcccc  120
cttattacag ccacgccgcg cggcacactt ttggcctttg ccgaggctag gaagatgtct  180
agttctgacg aaggcgctaa atttattgca ctcaggagat ccatggacca gggttccact  240
tggagcccta cagcttttat agttaatgac ggcgatgttc cagacggcct gaatctggga  300
gccgttgtct cagatgtaga aacaggagta gtgtttcttt tttattcact ctgtgcacac  360
aaggcgggat gccaggtcgc gtctacgatg ctggtatggt caaaggacga tggggtatcc  420
tggtcaacac caagaaatct ttcacttgat ataggcacgg aagtgttcgc tccgggaccc  480
ggctctggaa tacaaaagca aagagaaccg cgaaaagca ggctgatagt ttgtggacat  540
gggaccttgg agcgggatgg tgtattttgc ttgcttagcg atgaccacgg agcatcatgg  600
cgctatggca gtggggtgag cgggattccc tatgggcagc caaaacagga aaatgacttt  660
aaccccgatg agtgccagcc atacgaactt cctgatggtt cagtggtaat aaatgcgagg  720
aatcagaaca actaccattg ccattgtagg attgtcctcc gatcctatga cgcgtgtgac  780
actttgcgac cacgcgatgt aacgttcgat cccgagctgg tagatcctgt agtggcggct  840
ggtgccgtcg ttacaagctc aggtatcgtt tttttttagta acccggctca ccctgaattt  900
agagtcaacc tgaccctgag gtggagcttc tcaaacggta tcatcttggag aaaggagact  960
gtgcaattgt ggcctggccc ctcaggctac agttccctcg ctaccctcga aggatcaatg 1020
gatggagaag agcaagctcc ccaactttac gtgctctacg agaagggccg aaaccattat 1080
accgaaagca ttagcgtcgc gaagatcagc gtctatgaa ccctttccgg a           1131
```

-continued

```
SEQ ID NO: 30            moltype = DNA  length = 1038
FEATURE                  Location/Qualifiers
misc_feature             1..1038
                         note = Neu2 (with signal peptide removed)
source                   1..1038
                         mol_type = other DNA
                         organism = synthetic construct
SEQUENCE: 30
ggatccgaac aaagagcttc aaaaaaagat gagcacgccg agcttatagt gctccggcgg    60
ggggattacg atgcgcccac gcatcaggtg cagtggcagg cacaggaggt cgtagcgcag   120
gctcggcttg acggccatag aagtatgaat ccatgcccgc tttacgacgc acaaactggc   180
actctgtttt tgtttttat agcaatccca gggcaggtca cagagcagca acaactccag    240
acgcgagcta acgttacccg cctctgccaa gtaacttcca cgatcacgg taggacttgg    300
tcatctccac gcgacctcac tgatgcggcc attgggcctg cctaccgcga atggagcaca   360
ttcgctgtcg gaccgggtca ctgtttgcaa ctccacgaca gagcaaggtc cttggtggtg   420
ccagcctatg cctacaggaa gctgcatccc attcaaagac ccatcccttc cgcttttgc    480
ttccttagtc acgatcacgg caggacttgg gctagaggc attttgtagc gcaggacact   540
ttggaatgcc aagtggcaga ggtggaaacc ggcgaacaac gagtagtaac cctgaacgcc   600
agaagtcacc ttcgcgctcg cgtccaggcc caaagtacaa acgatggact tgacttccag   660
gaaagtcagc tcgttaagaa gctggtggaa ccgccacccc aagggtgtca gggcagtgtt   720
ataagttttc catctccccg cagtggccct ggtagcccgg cgcagtggtt gctgtacaca   780
cacccaaccc actcttggca acgggctgac cttggtgctt atctcaatcc tcgaccgcct   840
gcacccgagg catggtcaga acccgttttg ctggctaaag ggtcctgcgc gtacagcgac   900
ctgcagtcta tggggaccgg tcctgacgga agtccactgt ttgggtgcct ctatgaggca   960
aacgattatg aagaaattgt gtttctcatg ttcaccctta aacaggcatt tcccgccgaa  1020
tatctcccgc agtccgga                                                1038

SEQ ID NO: 31            moltype = DNA  length = 1302
FEATURE                  Location/Qualifiers
misc_feature             1..1302
                         note = Neu3
source                   1..1302
                         mol_type = other DNA
                         organism = synthetic construct
SEQUENCE: 31
ggatccgagg tgatggaaga agtaactact tgctcattta attccctct cttcagacag     60
gaagacgatc gaggcattac ttaccggatt cccgcccttt tgtatatacc acccacacat   120
acgtttcttg catttgcaga aaagcgctca acgcgcaggg atgaggatgc gcttcacctg   180
gtgctccggc gagggctccg aatcggtcaa cttgtccaat ggggccctct gaaaccctc    240
atggaggcta ctttgccagg tcacaggacc atgaatccgt gcccagtctg ggaacagaag   300
tcaggatgcg tgttttgtt tttcatctgc gttcgaggtc atgtgacgga gcgccagcag   360
attgtttcag gtcggaacgc tgcacgcttg tgcttcatat attcacaaga tgccggttgt   420
tcatggtctg aggtcagaga tctgaccgaa gaggtcattg gcagtgagtt gaagcattgg   480
gccacattcg ccgtaggacc cggacacgga atacagcttc agtctggtag gctcgtcatc   540
cctgcttata cctactatat tccatcatgg ttcttttgct tccaactgcc atgcaagacc   600
agacctcact ctttgatgat ttactcagac gatctgtggc tcacatggca tcacggtcga   660
ttgattcggc ctatggtcac ggtagagtgc gaggtagcgg aggtgacggg acagagctggc   720
caccctgtgt tgtattgctc agcgcgcacc cctaaccggt gcaggcgga agcactgtcc    780
acagatcatg gagaaggttt ccaaaggctc gctctttcac gccaactctg cgaaccacct   840
catggttgcc agggtagtgt cgtcagcttc cgaccattgg agataccgca tcggtgccaa   900
gatagctcat ccaaagacgc accgacgatc cagcagagta gtccaggatc ttccttgcgc   960
ttggaagaag aagctggtac cccatcagaa tcatggcttc tttactctca cccaacgtcc  1020
aggaagcaaa gagtagattt ggggatctac ctgaaccaaa cccccctcga agcggcgtgt  1080
tggagtaggc cctggattct ccattgtggc ccctgtgggt actctgacct tgcagcgttg  1140
gaggaagagg gattgttcgg ttgtcttttt gaatgcggga cgaagcagga gtgtgaacag  1200
attgcgttca gactcttcac tcatcgcgaa attctgagtc accttcaagg ggattgcacg  1260
tcaccgggcc gaaacccatc ccaattcaag agcaattccg ga                     1302

SEQ ID NO: 32            moltype = DNA  length = 1341
FEATURE                  Location/Qualifiers
misc_feature             1..1341
                         note = Neu4
source                   1..1341
                         mol_type = other DNA
                         organism = synthetic construct
SEQUENCE: 32
ggatcccagc gattgtcacc ggatgactcc catgcgcatc ggttggtttt gcgcagaggc     60
accctcgcgg gcgggagtgt gcgctgggc gctttgcatg tgttgggtac agcagccctc    120
gccgagcata gatcaatgaa cccttgtccc gtgcatgacg cggggacagg aactgtgttt   180
ttgttcttta ttgcggtact gggtcatacg cccgaagctc ttcaaattgc aacgggacga   240
aacgcggcca gactgtgttg tgttgcttcc agggatgcag gacttagctg gggctccgcg   300
cgggatctca cggaagaggc cattggcggc gcagttcagg actgggcaac ctttgctgtg   360
ggaccaggac atggagtgca gcttccgtca ggtcggttgt ggtcccggc ttacacatat   420
cgggtcgatc ggcgcgaatg tttcggaaag atatgccgaa cctctccgca cagttttgca   480
ttttactctg acgaccacgg ccggacgtgg aggtgcggag ggttggtgcc caatcttcgc   540
tccggtgaat gtcaattggc agctgtggac ggggacagg caggctcctt tctgtactgt   600
aatgctcgca gtccacttgg ttcccgcgtc caagctctga gtacagatga agggacttct   660
tttttgcctg ctgaacgagt tgcgtccctc cctgaaacgg cctggggttg ccaaggcagt   720
```

```
atagtgggtt ttccagctcc cgcacccaac cgccccaggg atgatagttg gtccgtgggt   780
cctggcagcc ctctgcagcc tcccttttg ggaccagggg tacatgagcc gccagaagag    840
gcggccgttg atcctagagg aggccaggtg ccaggtgggc cttttagcag actccagcct    900
agaggcgatg gaccgagaca gccgggggcct agaccagggg taagtggcga tgtgggtagt   960
tggacacttg cgctgccaat gcctttcgct gctcctcccc agtccccaac ttggctgctc   1020
tattctcacc cagtgggtag gcgcgctagg ctgcacatgg ggatacgcct ctcacagtcc   1080
ccgcttgatc ctagatcttg gacagaacct tgggtcatat atgaaggccc gagcggttac   1140
agcgacctgg cgagcatcgg tccagcaccg gagggtgggt tggtcttcgc gtgcttgtac   1200
gaaagcggcg cccgcactag ctacgatgag ataagctttt gcaccttctc attgagggaa   1260
gttcttgaaa atgtaccggc atcccccaaa cccccaaatc tcgggacaa gcccagagga    1320
tgctgttggc cctcctccgg a                                            1341

SEQ ID NO: 33            moltype = AA  length = 358
FEATURE                  Location/Qualifiers
REGION                   1..358
                         note = Neu1
source                   1..358
                         mol_type = protein
                         organism = synthetic construct
SEQUENCE: 33
MEQLLWVSGR QIGSVDTFRI PLITATPRGT LLAFAEARKM SSSDEGAKFI ALRRSMDQGS    60
TWSPTAFIVN DGDVPDGLNL GAVVSDVETG VVFLFYSLCA HKAGCQVAST MLVWSKDDGV   120
SWSTPRNLSL DIGTEVFAPG PGSGIQKQRE PRKGRLIVCG HGTLERDGVF CLLSDDHGAS   180
WRYGSGVSGI PYGQPKQEND FNPDECQPYE LPDGSVVINA RNQNNYHCHC RIVLRSYDAC   240
DTLRPRDVTF DPELVDPVVA AGAVVTSSGI VFFSNPAHPE FRVNLTLRWS FSNGTSWRKE   300
TVQLWPGPSG YSSLATLEGS MDGEEQAPQL YVLYEKGRNH YTESISVAKI SVYGTLSG     358

SEQ ID NO: 34            moltype = AA  length = 298
FEATURE                  Location/Qualifiers
REGION                   1..298
                         note = Neu2 (with signal peptide removed)
source                   1..298
                         mol_type = protein
                         organism = synthetic construct
SEQUENCE: 34
MNPCPLYDAQ TGTLFLFFIA IPGQVTEQQQ LQTRANVTRL CQVTSTDHGR TWSSPRDLTD    60
AAIGPAYREW STFAVGPGHC LQLHDRARSL VVPAYAYRKL HPIQRPIPSA FCFLSHDHGR   120
TWARGHFVAQ DTLECQVAEV ETGEQRVVTL NARSHLRARV QAQSTNDGLD FQESQLVKKL   180
VEPPPQGCQG SVISFPSPRS GPGSPAQWLL YTHPTHSWQR ADLGAYLNPR PPAPEAWSEP   240
VLLAKGSCAY SDLQSMGTGP DGSPLFGCLY EANDYEEIVF LMFTLKQAFP AEYLPQSG     298

SEQ ID NO: 35            moltype = AA  length = 430
FEATURE                  Location/Qualifiers
REGION                   1..430
                         note = Neu3
source                   1..430
                         mol_type = protein
                         organism = synthetic construct
SEQUENCE: 35
MEEVTTCSFN SPLFRQEDDR GITYRIPALL YIPPTHTFLA FAEKRSTRRD EDALHLVLRR    60
GLRIGQLVQW GPLKPLMEAT LPGHRTMNPC PVWEQKSGCV FLFFICVRGH VTERQQIVSG   120
RNAARLCFIY SQDAGCSWSE VRDLTEEVIG SELKHWATFA VGPGHGIQLQ SGRLVIPAYT   180
YYIPSWFFCF QLPCKTRPHS LMIYSDDLGV TWHHGRLIRP MVTVECEVAE VTGRAGHPVL   240
YCSARTPNRC RAEALSTDHG EGFQRLALSR QLCEPPHGCQ GSVVSFRPLE IPHRCQDSSS   300
KDAPTIQQSS PGSSLRLEEE AGTPSESWLL YSHPTSRKQR VDLGIYLNQT PLEAACWSRP   360
WILHCGPCGY SDLAALEEEG LFGCLFECGT KQECEQIAFR LFTHREILSH LQGDCTSPGR   420
NPSQFKSNSG                                                          430

SEQ ID NO: 36            moltype = AA  length = 402
FEATURE                  Location/Qualifiers
REGION                   1..402
                         note = Neu4
source                   1..402
                         mol_type = protein
                         organism = synthetic construct
SEQUENCE: 36
MNPCPVHDAG TGTVFLFFIA VLGHTPEAVQ IATGRNAARL CCVASRDAGL SWGSARDLTE    60
EAIGGAVQDW ATFAVGPGHG VQLPSGRLLV PAYTYRVDRR ECFGKICRTS PHSFAFYSDD   120
HGRTWRCGGL VPNLRSGECQ LAAVDGGQAG SFLYCNARSP LGSRVQALST DEGTSFLPAE   180
RVASLPETAW GCQGSIVGFP APAPNRPRDD SWSVGPGSPL QPPLLGPGVH EPPEEAAVDP   240
RGGQVPGGPF SRLQPRGDGP RQPGPRPGVS GDVGSWTLAL PMPFAAPPQS PTWLLYSHPV   300
GRRARLHMGI RLSQSPLDPR SWTEPWVIYE GPSGYSDLAS IGPAPEGGLV FACLYESGAR   360
TSYDEISFCT FSLREVLENV PASPKPPNLG DKPRGCCWPS SG                     402

SEQ ID NO: 37            moltype = AA  length = 605
FEATURE                  Location/Qualifiers
REGION                   1..605
                         note = Neu2- BBz (no leader)
```

-continued

```
source                    1..605
                          mol_type = protein
                          organism = synthetic construct
SEQUENCE: 37
MASLPVLQKE SVFQSGAHAY RIPALLYLPG QQSLLAFAEQ RASKKDEHAE LIVLRRGDYD    60
APTHQVQWQA QEVVAQARLD GHRSMNPCPL YDAQTGTLFL FFIAIPGQVT EQQQLQTRAN   120
VTRLCQVTST DHGRTWSSPR DLTDAAIGPA YREWSTFAVG PGHCLQLHDR ARSLVVPAYA   180
YRKLHPIQRP IPSAFCFLSH DHGRTWARGH FVAQDTLECQ VAEVETGEQR VVTLNARSHL   240
RARVQAQSTN DGLDFQESQL VKKLVEPPPQ GCQGSVISFP SPRSGPGSPA QWLLYTHPTH   300
SWQRADLGAY LNPRPPAPEA WSEPVLLAKG SCAYSDLQSM GTGPDGSPLF GCLYEANDYE   360
EIVFLMFTLK QAFPAEYLPQ SGTTTPAPRP PTPAPTIASQ PLSLRPEACR PAAGGAVHTR   420
GLDFACDIYI WAPLAGTCGV LLLSLVITLY CKRGRKKLLY IFKQPFMRPV QTTQEEDGCS   480
CRFPEEEGG  CELRVKFSRS ADAPAYKQGQ NQLYNELNLG RREEYDVLDK RRGRDPEMGG   540
KPRRKNPQEG LYNELQKDKM AEAYSEIGMK GERRRGKGHD GLYQGLSTAT KDTYDALHMQ   600
ALPPR                                                              605

SEQ ID NO: 38             moltype = AA   length = 474
FEATURE                   Location/Qualifiers
REGION                    1..474
                          note = Neu2-hinge-Tm
source                    1..474
                          mol_type = protein
                          organism = synthetic construct
SEQUENCE: 38
MALPVTALLL PLALLLHAAR PGSMASLPVL QKESVFQSGA HAYRIPALLY LPGQQSLLAF    60
AEQRASKKDE HAELIVLRRG DYDAPTHQVQ WQAQEVVAQA RLDGHRSMNP CPLYDAQTGT   120
LFLFFIAIPG QVTEQQQLQT RANVTRLCQV TSTDHGRTWS SPRDLTDAAI GPAYREWSTF   180
AVGPGHCLQL HDRARSLVVP AYAYRKLHPI QRPIPSAFCF LSHDHGRTWA RGHFVAQDTL   240
ECQVAEVETG EQRVVTLNAR SHLRARVQAQ STNDGLDFQE SQLVKKLVEP PPQGCQGSVI   300
SFPSPRSGPG SPAQWLLYTH PTHSWQRADL GAYLNPRPPA PEAWSEPVLL AKGSCAYSDL   360
QSMGTGPDGS PLFGCLYEAN DYEEIVFLMF TLKQAFPAEY LPQSGTTTPA PRPPTPAPTI   420
ASQPLSLRPE ACRPAAGGAV HTRGLDFACD IYIWAPLAGT CGVLLLSLVI TLYC         474

SEQ ID NO: 39             moltype = DNA   length = 1815
FEATURE                   Location/Qualifiers
misc_feature              1..1815
                          note = Neu2- BBz (no leader)
source                    1..1815
                          mol_type = other DNA
                          organism = synthetic construct
SEQUENCE: 39
atggcttcct tgccggtgct gcaaaaagag agcgtattcc agtcaggcgc ccatgcgtat    60
agaatcccgg cacttctcta tttgccgggc caacaaagtc tcttggcgtt cgcggaacag   120
cgggcgtcca aaaaagacga acacgccgag ttgattgtgc tccgccgcgg ggattatgat   180
gccccaacgc atcaggttca gtggcaggca caagaggtag tcgctcaggc gcgactggat   240
ggacatcggt caatgaaccc atgtccactg tacgatgctc agacaggtac gttgtttctg   300
ttcttcatcg ctatccctgg gcaagtaaca gaacaacaac aactgcaaac cagagccaat   360
gtaacaagac tctgccaggt aactagcact gaccacggac gaacgtggtc ttcccctaga   420
gatcttactg acgccgcaat cgggcctgca tatcgcgaat ggagcacttt cgcagtaggc   480
cctggtcatt gcctgcaact ccatgatcgc gcccgatcac ttgtggtgcc agcgtacgca   540
taccggaagc tccatccaat acaacgcccc atcccgtccg cttttttgttt cctctcccat   600
gaccacgggc ggacttgggc gcggggtcat ttcgtcgcac aggatacgtt ggagtgtcag   660
gtagcggaag tagaaaccgg ggagcagaga gtggtcactc tcaacgcgcg cagtcatctt   720
cgcgcccgcg tacaggcgca gagcactaat gacgggcttg attttcaaga aagtcaactc   780
gtcaaaaagt tggttgaacc gccccgcag  ggctgtcaag gttcagttat aagttttcca   840
agtccacgct ccggtccagg atcaccagca cagtggcttc tctacaccca tcccacccac   900
agctggcagc gggcagatct tggtgcttac ttgaatccca ggccaccggc ccccgaagcc   960
tggagcgagc ctgtactgct tgcaaagggg agctgtgcgt actctgatct ccagtcaatg  1020
ggtactggac cagatgggag tccattgttt ggttgtctct acgaggcgaa cgattatgag  1080
gaaatcgttt tcttatgtt tactttgaaa caggcgttcc cagccgaata tttgcctcag  1140
tccggaacca cgacgccagc gccgcgacca ccaacaccgg cgcccaccat cgcgtcgcag  1200
cccctgtccc tgcgcccaga ggcgtgccgg ccagcggcag ggggcgcagt gcacacgagg  1260
gggctggact cgcctgtga  tatctacatc tgggcgccct tggccgggac ttgtgggggtc  1320
cttctcctgt cactggttat cacccttac  tgcaaacggg gcagaaagaa actcctgtat  1380
atattcaaac aaccatttat gagaccagta caaactactc aagaggaaga tggctgtagc  1440
tgccgatttc cagaagaaga agaaggagga tgtgaactga gagtgaagtt cagcaggagc  1500
gcagacgccc ccgcgtacaa gcagggccag aaccagctct ataacgagct caatctagga  1560
cgaagagagg agtacgatgt tttggacaag agacgtggcc gggaccctga gatggggggga  1620
aagccgagaa ggaagaaccc tcaggaaggc ctgtacaatg aactgcagaa agataagatg  1680
gcggaggcct acagtgagat tgggatgaaa ggcgagcgcc ggaggggcaa ggggcacgat  1740
ggcctttacc agggtctcag tacagccacc aaggacacct acgacgccct tcacatgcag  1800
gccctgcccc ctcgc                                                   1815

SEQ ID NO: 40             moltype = DNA   length = 1422
FEATURE                   Location/Qualifiers
misc_feature              1..1422
                          note = Neu2-hinge-Tm
```

-continued

```
source                  1..1422
                        mol_type = other DNA
                        organism = synthetic construct
SEQUENCE: 40
atggccttac cagtgaccgc cttgctcctg ccgctggcct tgctgctcca cgccgccagg   60
ccgggatcca tggcttcctt gccggtgctg caaaaagaga gcgtattcca gtcaggcgcc   120
catgcgtata gaatcccggc acttctctat ttgccgggcc aacaaagtct cttggcgttc   180
gcggaacagc gggcgtccaa aaaagacgaa cacgccgagt tgattgtgct ccgccgcggg   240
gattatgatg ccccaacgca tcaggttcag tggcaggcac aagaggtagt cgctcaggcg   300
cgactggatg gacatcggtc aatgaaccca tgtccactgt acgatgctca gacaggtacg   360
ttgtttctgt tcttcatcgc tatccctggg caagtaacag aacaacaaca actgcaaacc   420
agagccaatg taacaagact ctgccaggta actagcactg accacggacg aacgtggtct   480
tcccctagag atcttactga cgccgcaatc gggcctgcat atcgcgaatg gagcactttc   540
gcagtaggcc ctggtcattg cctgcaactc catgatcgcg cccgatcact tgtggtgcca   600
gcgtacgcat accggaagct ccatccaata caacgcccca tcccgtccgc tttttgtttc   660
ctctcccatg accacgggcg gacttgggcg cggggtcatt tcgtcgcaca ggatacgttg   720
gagtgtcagg tagcggaagt agaaaccggg gagcagagag tggtcactct caacgcgcgc   780
agtcatcttc gcgcccgcgt acaggcgcag agcactaatg acgggcttga ttttcaagaa   840
agtcaactcg tcaaaaagtt ggttgaaccc ccccgcagg gctgtcaagg ttcagttata   900
agttttccaa gtccacgctc cggtccagga tcaccagcac agtggcttct ctacacccat   960
cccacccaca gctggcagcg ggcagatctt ggtgcttact tgaatcccag gccaccggcc   1020
cccgaagcct ggagcgagcc tgtactgctt gcaaaggcga gctgtgcgta ctctgatctc   1080
cagtcaatgg gtactggacc agatgggagt ccattgtttg gttgtctcta cgaggcgaac   1140
gattatgagg aaatcgtttt tcttatgttt actttgaaac aggcgttccc agccgaatat   1200
ttgcctcagt ccgggaaccac gacgccagcg ccgcgaccac caacaccggc gcccaccatc   1260
gcgtcgcagc ccctgtccct gcgcccagag gcgtgccggg gggcgcagtg   1320
cacacgaggg ggctggactt cgcctgtgat atctacatct gggcgccctt ggccgggact   1380
tgtggggtcc ttctcctgtc actggttatc acccttact gc   1422
```

SEQ ID NO: 41          moltype = AA   length = 5
FEATURE                Location/Qualifiers
REGION                 1..5
                       note = linker
source                 1..5
                       mol_type = protein
                       organism = synthetic construct
SEQUENCE: 41
GSGSG                                                              5

SEQ ID NO: 42          moltype = AA   length = 5
FEATURE                Location/Qualifiers
REGION                 1..5
                       note = linker
source                 1..5
                       mol_type = protein
                       organism = synthetic construct
SEQUENCE: 42
GSGGG                                                              5

SEQ ID NO: 43          moltype = AA   length = 5
FEATURE                Location/Qualifiers
REGION                 1..5
                       note = linker
source                 1..5
                       mol_type = protein
                       organism = synthetic construct
SEQUENCE: 43
GGGSG                                                              5

SEQ ID NO: 44          moltype = AA   length = 5
FEATURE                Location/Qualifiers
REGION                 1..5
                       note = linker
source                 1..5
                       mol_type = protein
                       organism = synthetic construct
SEQUENCE: 44
GSSSG                                                              5

SEQ ID NO: 45          moltype = AA   length = 5
FEATURE                Location/Qualifiers
REGION                 1..5
                       note = linker
source                 1..5
                       mol_type = protein
                       organism = synthetic construct
SEQUENCE: 45
GGGGS                                                              5

-continued

```
SEQ ID NO: 46          moltype = AA  length = 15
FEATURE                Location/Qualifiers
REGION                 1..15
                       note = linker
source                 1..15
                       mol_type = protein
                       organism = synthetic construct
SEQUENCE: 46
GGGGSGGGGS GGGGS                                                    15

SEQ ID NO: 47          moltype = AA  length = 45
FEATURE                Location/Qualifiers
REGION                 1..45
                       note = linker
source                 1..45
                       mol_type = protein
                       organism = synthetic construct
SEQUENCE: 47
GGTGGCGGTG GCTCGGGCGG TGGTGGGTCG GGTGGCGGCG GATCT                   45

SEQ ID NO: 48          moltype = AA  length = 5
FEATURE                Location/Qualifiers
REGION                 1..5
                       note = linker
REPEAT                 1..5
                       note = repeat n times. where n represents an integer of at
                        least 1
source                 1..5
                       mol_type = protein
                       organism = synthetic construct
SEQUENCE: 48
GGGGS                                                                5

SEQ ID NO: 49          moltype = AA  length = 5
FEATURE                Location/Qualifiers
REGION                 1..5
                       note = hinge
source                 1..5
                       mol_type = protein
                       organism = synthetic construct
SEQUENCE: 49
DKTHT                                                                5

SEQ ID NO: 50          moltype = AA  length = 4
FEATURE                Location/Qualifiers
REGION                 1..4
                       note = hinge
source                 1..4
                       mol_type = protein
                       organism = synthetic construct
SEQUENCE: 50
CPPC                                                                 4

SEQ ID NO: 51          moltype = AA  length = 15
FEATURE                Location/Qualifiers
REGION                 1..15
                       note = hinge
source                 1..15
                       mol_type = protein
                       organism = synthetic construct
SEQUENCE: 51
CPEPKSCDTP PPCPR                                                    15

SEQ ID NO: 52          moltype = AA  length = 12
FEATURE                Location/Qualifiers
REGION                 1..12
                       note = hinge
source                 1..12
                       mol_type = protein
                       organism = synthetic construct
SEQUENCE: 52
ELKTPLGDTT HT                                                       12

SEQ ID NO: 53          moltype = AA  length = 10
FEATURE                Location/Qualifiers
REGION                 1..10
                       note = hinge
```

-continued

```
source                    1..10
                          mol_type = protein
                          organism = synthetic construct
SEQUENCE: 53
KSCDKTHTCP                                                                10

SEQ ID NO: 54             moltype = AA   length = 7
FEATURE                   Location/Qualifiers
REGION                    1..7
                          note = hinge
source                    1..7
                          mol_type = protein
                          organism = synthetic construct
SEQUENCE: 54
KCCVDCP                                                                    7

SEQ ID NO: 55             moltype = AA   length = 7
FEATURE                   Location/Qualifiers
REGION                    1..7
                          note = hinge
source                    1..7
                          mol_type = protein
                          organism = synthetic construct
SEQUENCE: 55
KYGPPCP                                                                    7

SEQ ID NO: 56             moltype = AA   length = 15
FEATURE                   Location/Qualifiers
REGION                    1..15
                          note = hinge
source                    1..15
                          mol_type = protein
                          organism = synthetic construct
SEQUENCE: 56
EPKSCDKTHT CPPCP                                                          15

SEQ ID NO: 57             moltype = AA   length = 12
FEATURE                   Location/Qualifiers
REGION                    1..12
                          note = hinge
source                    1..12
                          mol_type = protein
                          organism = synthetic construct
SEQUENCE: 57
ERKCCVECPP CP                                                             12

SEQ ID NO: 58             moltype = AA   length = 17
FEATURE                   Location/Qualifiers
REGION                    1..17
                          note = hinge
source                    1..17
                          mol_type = protein
                          organism = synthetic construct
SEQUENCE: 58
ELKTPLGDTT HTCPRCP                                                        17

SEQ ID NO: 59             moltype = AA   length = 12
FEATURE                   Location/Qualifiers
REGION                    1..12
                          note = hinge
source                    1..12
                          mol_type = protein
                          organism = synthetic construct
SEQUENCE: 59
SPNMVPHAHH AQ                                                             12

SEQ ID NO: 60             moltype = AA   length = 9
FEATURE                   Location/Qualifiers
REGION                    1..9
                          note = NY-ESO157-165
source                    1..9
                          mol_type = protein
                          organism = synthetic construct
SEQUENCE: 60
SLLMWITQC                                                                  9
```

What is claimed:

1. A modified immune cell or precursor cell thereof, comprising a chimeric cell surface sialidase (neuraminidase) enzyme comprising:

(a) an extracellular portion comprising a sialidase (neuraminidase), wherein the sialidase is selected from the group consisting of Neu1, Neu2, Neu3, and Neu4, (b) a heterologous transmembrane domain capable of tethering the extracellular portion to a cell surface; and (c) an intracellular region comprising a costimulatory signaling domain and an intracellular signaling domain;

wherein the intracellular signaling domain comprises a cytoplasmic signaling domain of a human CD3 zeta chain (CD3z), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, or CD66d; and wherein the costimulatory signaling domain comprises a costimulatory domain of a protein in the TNFR superfamily, CD28, 4-1BB, OX40, PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, or B7-H3.

2. The modified immune cell or precursor cell thereof of claim 1, wherein the sialidase is Neu1.

3. The modified immune cell or precursor cell thereof of claim 1, wherein the sialidase is Neu2.

4. The modified immune cell or precursor cell thereof of claim 1, wherein the heterologous transmembrane domain comprises an artificial hydrophobic sequence or a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), or CD154.

5. The modified immune cell or precursor cell thereof of claim 1, wherein the heterologous transmembrane domain is a transmembrane domain of CD8.

6. The modified immune cell or precursor cell thereof of claim 1, wherein the heterologous transmembrane domain comprises the amino acid sequence set forth in SEQ ID NO: 16.

7. The modified immune cell or precursor cell thereof of claim 1, wherein the intracellular signaling domain comprises an intracellular domain of human CD3z.

8. The modified immune cell or precursor cell thereof of claim 1, wherein the intracellular signaling domain comprises the amino acid sequence set forth in SEQ ID NO: 18.

9. The modified immune cell or precursor cell thereof of claim 1, wherein the costimulatory signaling domain comprises a costimulatory domain of CD28 or CD2.

10. The modified immune cell or precursor cell thereof of claim 1, wherein the costimulatory signaling domain comprises a costimulatory domain of 4-1BB.

11. The modified immune cell or precursor cell thereof of claim 1, wherein the costimulatory signaling domain comprises the amino acid sequence set forth in SEQ ID NO: 17.

12. The modified immune cell or precursor cell thereof of claim 1, further comprising a hinge domain.

13. The modified immune cell or precursor cell thereof of claim 12, wherein the hinge domain is selected from the group consisting of an Fc fragment of an antibody, a hinge region of an antibody, a CH2 region of an antibody, a CH3 region of an antibody, an artificial hinge domain, and a hinge of CD8.

14. The modified immune cell or precursor cell thereof of claim 12, wherein the hinge domain comprises a hinge of CD8.

15. The modified immune cell or precursor cell thereof of claim 12, wherein the hinge domain is encoded by a nucleic acid sequence comprising SEQ ID NO: 6.

16. The modified immune cell or precursor cell thereof of claim 1, wherein the chimeric cell surface sialidase is encoded by the nucleic acid sequence set forth in SEQ ID NO: 1 or 40.

17. The modified immune cell or precursor cell thereof of claim 1, further comprising a chimeric antigen receptor (CAR) or T cell receptor (TCR).

18. The modified immune cell or precursor cell thereof of claim 17, wherein the CAR or the TCR has specificity for a tumor associated antigen (TAA).

19. The modified immune cell or precursor cell thereof of claim 18, wherein the TAA is selected from the group consisting of TnMUC1, CD19, and PSMA.

20. A pharmaceutical composition comprising the modified immune cell or precursor cell of claim 1.

* * * * *